US005601816A

United States Patent [19]

Kit et al.

[11] Patent Number: 5,601,816

[45] **Date of Patent: *Feb. 11, 1997**

[54] INFECTIOUS BOVINE RHINOTRACHEITIS VIRUS INSERTION MUTANTS, VACCINES CONTAINING SAME, AND METHODS FOR THE PRODUCTION OF SAME

[75] Inventors: Malon Kit; Saul Kit, both of Houston, Tex.

[73] Assignees: Novagene, Inc.; Baylor College of Medicine, both of Houston, Tex.

[ * ] Notice: The term of this patent shall not extend beyond the expiration date of Pat. No. 4,703,011.

[21] Appl. No.: 392,406

[22] Filed: Feb. 22, 1995

Related U.S. Application Data

[63] Continuation of Ser. No. 899,013, Jun. 15, 1992, abandoned, which is a continuation of Ser. No. 148,725, Jan. 26, 1988, abandoned.

[51] Int. Cl.$^6$ ........................ A61K 39/265; A61K 35/76; C12N 7/00; C12N 7/01

[52] U.S. Cl. .................... 424/93.2; 424/93.6; 435/172.3; 435/235.1; 435/320.1

[58] Field of Search ................................. 435/69.1, 69.3, 435/172.1, 236, 172.3, 320.1, 235.1; 424/93.1, 93.6, 93.2

[56] References Cited

U.S. PATENT DOCUMENTS

| | | | |
|---|---|---|---|
| 4,569,840 | 2/1986 | Kit | 424/89 |
| 4,703,011 | 10/1987 | Kit | 435/236 |
| 4,753,884 | 6/1988 | Kit | 435/235 |
| 4,824,667 | 4/1989 | Kit et al. | 424/205.1 |
| 5,128,129 | 7/1992 | Kit | 424/89 |

FOREIGN PATENT DOCUMENTS

| | | | |
|---|---|---|---|
| 0176170 | 2/1986 | European Pat. Off. | C12N 15/00 |
| WO8704463 | 7/1987 | WIPO | C12N 15/00 |

OTHER PUBLICATIONS

Shih et al., PNAS, vol. 81, pp. 5867–5870, Sep. 1984.
Liu et al., Gene, vol. 44, pp. 279–285, 1986.
Kit et al, *Vaccines*, 91 (1991).
Kit et al, *J. Vet. Diag. Invest.*, 2:14–23 (1990).
Fenner et al, *Veterinary Virology*, Academic Press, Inc., pp. 353–356 (1987).
Ben–Porat et al, *Virol.*, 154:325–334 (1986).
Zuckerman et al, *Virol.*, 64:802–812 (1990).
Zwaagstra et al, *J. Virol.*, 64:5019–5028 (1990).
Murphy et al, *J. Biol. Chem.*, 259:10208–10211 (1984).
Bhat et al, *Mol. Cell. Biol.*, 3:1996–2005 (1983).
Bhat et al, *J. Virol.*, 56:750–756 (1985).
Bachmann et al, *J. Gen. Virol.*, 67:2587–2594 (1986).
Grosschedl et al, *Cell*, 41:885–897 (1985).
Kit, *Microbiological Sciences*, 2:369–375 (1985).
Kit, in *Immunobiology of Proteins and Peptides V*, Atassi, Ed., (Plenum Publishing Corp., 1989), pp. 219–236.
Kit, in *Technological Advances in Vaccine Development*, pp. 183–195 (1988).

*Primary Examiner*—David Guzo
*Attorney, Agent, or Firm*—Sughrue, Mion, Zinn, Macpeak & Seas

[57] ABSTRACT

The present invention relates to infectious bovine rhinotracheitis viruses which fail to produce any functional thymidine kinase as a result of an insertion in the thymidine kinase gene, vaccines against infectious bovine rhinotracheitis containing the same and methods for production and use of same. The present invention also relates to infectious bovine rhinotracheitis-based viral vectors useful for the coexpression of foreign genes.

46 Claims, 11 Drawing Sheets

PROBE: pSP64/PRVtk

INFECTIOUS BOVINE RHINOTRACHEITIS VIRUS INSERTION MUTANTS, VACCINES CONTAINING SAME, AND METHODS FOR THE PRODUCTION OF SAME

The invention described herein was developed during the tenure of a Research Career Award to Dr. Saul Kit from the United States Public Health Service of the Department of Health and Human Services. The Government has certain rights.

This is a Continuation of application Ser. No. 07/899,013, filed on Jun. 15, 1992, abandoned; which in turn is a Continuation of Ser. No. 07/148,725, filed on Jan. 26, 1988, now abandoned.

FIELD OF THE INVENTION

The present invention relates to infectious bovine rhinotracheitis viruses which fail to produce any functional thymidine kinase as a result of an insertion in the thymidine kinase gene, vaccines against infectious bovine rhinotracheitis containing the same and methods for production and use of same. The present invention also relates to infectious bovine rhinotracheitis based viral vectors useful for the coexpression of foreign genes.

BACKGROUND OF THE INVENTION

I. Infectious Bovine Rhinotracheitis Disease

The alpha herpesvirus, bovine herpesvirus type 1 (hereinafter "BHV-1"), more commonly known as infectious bovine rhinotracheitis virus (hereinafter "IBRV") and infectious pustular vulvovaginitis virus (hereinafter "IPV"), is a direct cause of bovine disease and is a major factor in the initiation of bacterial pneumonia (Ludwig, H., In: *The Herpesviruses*., Ed. B. Roizman, 2:135–314 (Plenum Press: New York) (1983); Pastoret, P. P., et al, *Ann. Rech. Vet.*, 13:221–235 (1982); Yates, W. D. G., *Can. J. Comp. Med.*, 46:225–263 (1982); Gibbs, E. P. J. et al, *Vet. Bull.* (London) Part I, 47:317–343 (1977); and Gibbs, E. P. J. et al *Vet. Bull.* (London) Part II, 47:411–425 (1977)). Infectious bovine rhinotracheitis (hereinafter "IBR") has a worldwide distribution and is probably the single most costly disease of cattle in the United States. Respiratory IBR disease in the United States costs about $25 million. Additional losses associated with IBRV infections result from abortion storms, fatalities in newborn calves, losses in milk yield, conjunctivitis, metritis, enteritis and meningitis.

The spread of IBR in naturally and artificially bred cattle poses a serious problem, especially with the continued widespread use of frozen semen. Recurrent shedding of virus from infected bulls also constitutes a significant threat to the artificial insemination industry in the United States and to the worldwide distribution of bovine germ plasm. The incrimination of IBRV as the etiologic agent of oophoritis and salpingitis with resultant infertility and sterility adds to the seriousness of IBRV infections.

The severity of illness resulting from IBRV infections depends on the virus strain and on the age of the animal affected. After recovery from infection, animals may show signs of recurrent disease without being reexposed to the virus. Recurrent disease without reexposure occurs because the virus remains dormant, i.e., latent, in neurons of the sensory ganglia of its host and can be reactivated, even after long periods (Rock, D.L. et al, *J. Gen. Virol.*, 67:2515–2520 (1986); Homan, E. J. et al, *Am. J. Vet. Res.*, 41:1212–1213 (1980); and Rodriguez, L. L. et al, *Am. J. Vet. Res.*, 45:1069–1072 (1984)). Dexamethasone treatment can also provoke recrudescence of virus shedding with or without clinical symptoms of active IBR. This suggests that reactivation and release from neuronal sites and, possibly, persistent infection of other tissues, can occur (Narita, M. et al, *Am. J. Vet. Res.*, 42:1192–1193 (1981); Sheffy, B. E. et al, *J. Am. Vet. Med. Assoc.*, 163:850–851 (1973); Homan, E. J. et al, *Am. J. Vet. Res.*, 43:309–313 (1983); Ackermann, M. et al, *Am. J. Vet. Res.*, 43:36–40 (1982); Ackermann, M. et al, *Veter. Microbiol*, 9:53–63 (1984); and Edwards, S. et al, *Veter. Microbiol*, 8:563–569 (1983)). However, reactivation of IBRV from latency can also occur spontaneously, so that cattle latently infected with field strains of IBRV represent a sporadic source of virus transmission and herd infection.

II. Known IBR Vaccines

Control of IBR is based largely on vaccination. However, vaccination may not prevent second infections by pathogenic field strains, although vaccination does increase the effective dose required to initiate second infections and it reduces the amount and duration of virus shedding. Further, vaccinated animals have less severe clinical signs than unvaccinated animals. As a result of all these factors, spread of pathogenic field strains in the herd may be reduced by vaccination.

Currently, three types of IBR vaccines are being employed: (1) killed virus vaccines; (2) subunit vaccines; and (3) modified-live virus (hereinafter "MLV") vaccines (U.S. Pat. Nos. 3,634,587 3,925,544 and 4,291,019). Killed IBR vaccines have been produced by treating IBRV with chemicals, such as formalin or ethanol, and/or physical agents, such as heat or ultraviolet irradiation. Subunit IBR vaccines have been prepared by solubilizing IBRV-infected cell cultures with nonionic detergents and purifying some of the solubilized virus proteins (Babiuk, L. A. et al, *Virol.*, 159:57–66 (1987)). Early MLV vaccines were designed for parenteral administration and consisted of IBRV attenuated by rapid passage in bovine cell cultures or by adaptation of IBRV to porcine or canine cell cultures, by adaptation to growth in cell culture at a low temperature (30° C.), or by selection of heat-stable virus particles (56° C. for 40 min). Specialized types of MLV vaccines are those administered intranasally. These MLV vaccines have been attenuated by serial passage in rabbit cell cultures or by treatment of IBRV with nitrous acid followed by selection for temperature-sensitive mutants (Todd, J. D. et al, *J. Am. Vet. Med. Assoc.*, 159:1370–1374 (1971); Todd, J. D. et al, *Infect. Immun.*, 5:699–706 (1973); Zygraith, N. et al, *Res. Vet. Sci.*, 16:328–335 (1974); Kucera, C. J. et al, *Am. J. Vet. Res.*, 39:607–610 (1978); and Smith, M. W. et al, *Can. Vet. J.*, 19:63–71 (1978)). Temperature-sensitive virus vaccines are restricted in their replication to the nasal mucosa because the temperature of the nasal mucosa is several degrees lower than that of the body. Temperature-sensitive viruses are unable to replicate at the higher temperatures of the lower respiratory tract. Hence, their growth and spread in the body is self-limiting.

The currently available IBR vaccines discussed above have serious disadvantages and have, therefore, proved unsatisfactory in commercial use. More specifically, although killed IBRV vaccines are considered to be safer than MLV vaccines, i.e., they cannot establish latency and they eliminate the problem of postvaccination shedding, they are expensive to produce, must be administered several times, and disadvantageously require adjuvants. In addition, with their use, there is the possibility of fatal hypersensitivity reactions and nonfatal urticaria. Further, some infectious virus particles may survive the killing process and thus cause disease. Moreover, animals vaccinated with killed IBRV vaccines can be infected at a later time with virulent virus. The virulent virus can establish a latent infection and can be reactivated and shed, thereby spreading infection in the herd (Frerichs, G. N. et al, *Vet. Rec.,* 111:116–122 (1982); Wiseman, A. et al, *Vet. Rec.,* 104:535–536 (1979); and Zuffa, A. et al, *Zentralbl. Veterinaermed. Reihe B.,* 27:725–733 (1980)). Accordingly, although killed IBR vaccines can provide some protection against IBR, they are generally inferior to MLV vaccines in providing long term protection.

Subunit vaccines are often less toxic than killed virus vaccines, and may induce novel immunologic effects which can be of significant value. The technique for subunit vaccine preparation involves removal of capsid proteins, while leaving intact antigenic proteins that elicit protective immunity. This creates a potential for the development of serologic procedures to differentiate vaccinated from naturally infected animals. Further, subunit vaccines, though antigenic, do not contain live virus and, thus, cannot be transmitted to other animals, cause abortion, or establish latency (Lupton, H. W. et al, *Am. J. Vet. Res.,* 41:383–390 (1980); and le Q. Darcel, C. et al, *Can. J. Comp. Med.,* 45:87–91 (1981)). However, subunit vaccines, like killed vaccines, do not generally prevent infection and latency when animals are subsequently exposed to virulent IBRV field strains. Other disadvantages of subunit vaccines are the high cost of purification and the requirement of several injections with adjuvant.

MLV IBR vaccines have the important advantage that they produce rapid protection and activate cell-mediated and humoral components of the immune system. In the case of intranasal (hereinafter "IN") administration, localized immune responses that suppress later replication of virulent IBRV in the respiratory tract contribute significantly to protection. The local immune responses include production of interferon and IgA antibodies in nasal secretions (Kucera, C. J. et al, *Am. J. Vet. Res.,* 39:607–610 (1978)). Extensive utilization of MLV IBR vaccines has reduced the frequency of occurrence of IBR. However, most of the available MLV IBR vaccines are not entirely satisfactory. More specifically, there is concern as to their safety, especially if the vaccine virus itself produces latency and may be shed and transmitted to susceptible cattle.

Maximal utilization of intramuscularly (hereinafter "IM") -administered MLV IBR vaccines has been especially hampered by the hazards of vaccine-induced abortions. That is, abortion rates as high as 60% have been reported after IM administration of some MLV IBR vaccines (Kahrs, R. F., *J. Am. Vet. Med. Assoc.,* 171:1055–1064 (1977); and Kendrick, J. W. et al, *Am. J. Vet. Res.,* 28:1269–1282 (1967)). In addition, with the MLV IBR vaccines currently in use, there is the danger of reversion to virulence.

In a search for safer MLV IBR vaccines, specialized vaccines have been developed (Todd, J.D. et al, *J. Am. Vet. Med. Assoc.,* 159:1370–1374 (1971); Kahrs, R. F. et al, *J. Am. Vet. Med. Assoc.,* 163:427–441 (1973); Smith, M. W. et al, *Can. Vet. J.,* 19:63–71 (1979); Zygraich, N. et al, *Res. Vet. Sci.,* 16:328–335 (1974); and Kucera, C. J. et al, *Am. J. Vet. Rest,* 39:607–610 (1978)). These vaccines have been found to be immunogenic and safe for IN administration to pregnant cattle and can prevent abortions in pregnant cows which have been challenge-exposed to virulent IBRV. However, they have a disadvantage in that they can only be administered by the IN route. This is because, when administered IN, one such IBR vaccine replicates to a limited extent at the lower temperature of the upper respiratory tract. However, when administered IM, the vaccine replicates poorly or not at all at normal body temperatures (Zygraich, N. et al, *Res. Vet. Sci.,* 16:328–335 (1974)). On the other hand, another IBR vaccine is insufficiently attenuated for IM administration to pregnant animals although safe when given IN (Todd, J. D., *J. Am. Vet. Med. Assoc.,* 163:427–441 (1973)). Furthermore, some of the vaccine strains produce mild or moderate respiratory disease even after IN administration, and they do not prevent signs of IBR following field challenge exposure (Kahrs, R. F. et al, *J. Am. Vet. Med. Assoc.,* 163:437–441 (1973)). Vaccination by temperature-sensitive viruses does not prevent the installation of virulent virus in a latent form or the reexcretion of the virulent virus. Moreover, vaccination with temperature-sensitive viruses does not inhibit reexcretion of a wild-type strain latently carried by animals at the time of vaccination (Nettleton, P. F. et al, In: *Latent Herpesvirus Infections in Veterinary Medicine,* Eds. G. Whittmann, R. M. Gaskell and H.-J. Rziha (Martinus Nijhoff Publishers: Boston/The Hague/Dordrecht), pages 191–209 (1984); Straub, O. C., *Comp. Immun. Microbiol. Infect. Dis.,* 2:285–294 (1979); Thiry, E. et al, *Veterin. Microbiol.* 10:371–380 (1985); and Zuffa, A. et al, *Zentrabl. Veterinaermed. Reihe B.,* 29:413–425 (1982)).

Accordingly, neither the IM-administered MLV IBR vaccines, which are unsafe for pregnant cows, nor the MLV IBR vaccines that must be administered IN, discussed above fit comfortably into many of the current management practices. That is, vaccination of large numbers of animals by the IN route is inconvenient and potentially dangerous to animal handlers. In addition, screening to identify pregnant animals prior to immunization is often not desirable or cost effective.

III. Attenuated Properties of Thymidine Kinase-Negative Herpesvirus Mutants

Recently, temperature-resistant, thymidine kinase-negative (hereinafter "$tk^-$") IBR vaccines derived from the thymidine kinase positive (hereinafter "$tk^+$"), i.e., wild-type, Los Angeles strain of IBRV (ATCC No. VR 188) have been developed which overcome many of the problems that have limited the use of currently available vaccines (Kit, S. et al, *Virol.,* 130:381–389 (1983); Kit, S. et al, *Arch. Virol.,* 86:63–83 (1985); Kit, S. et al, *Vaccine,* 4:55–61 (1986); and U.S. Pat. Nos. 4,569,840 and 4,703,011, which articles and patents are incorporated by reference herein in their entirety)). These IBRV vaccines consist of plaque-purified IBRV isolates that replicate equally well at either 39.1° C. or 34.5° C. in rabbit skin, bovine tracheal cells and bovine kidney cells. Hence, they are designed "temperature-resistant". This is in contrast to those IBRV strains that are designated "temperature-sensitive", that is, those used for the IN-administered vaccines which replicate only about $10^{-4}$ to $10^{-7}$ as well at 39.1° C. as at 34.5° C. In addition to the ability to replicate equally well at 39.1° C. or 34.5° C., the $tk^-$ IBR vaccines lack the ability to produce a functional thymidine kinase enzyme (hereinafter "TK") in infected cells. In one vaccine, designated IBRV(B8-D53) (ATCC No. VR 2066) (U.S. Pat. No. 4,569,840), the failure to produce a functional TK results from a mutagen-induced mutation. With a second vaccine, designated IBRV(NG)dltk (ATCC No. VR 2112) (U.S. Pat. No. 4,703,011), the failure to produce a functional TK results from a deletion of about 400 base pairs (hereinafter "bp") from the coding sequences of the IBRV tk gene. In addition to this deletion, there is an insertion into the IBRV tk gene of a 40 bp oligonucleotide, designated NG, with stop codons in all three reading frames. The characteristics, i.e., temperature resistance and $tk^-$, directly contribute to the superiority of these IBRVs as vaccines.

As an alternative to the above-described tk⁻ mutagen-induced mutants and tk⁻ deletion mutants of IBRV, embodiments of the present invention were developed. Specifically, these embodiments relate to IBRV mutants that fail to produce any functional thymidine kinase as a result of an insertion in the coding region of the IBRV tk gene without deleting any nucleotide sequences from the IBRV tk gene. Insertion mutations inactivate the function of the IBRV tk gene by disrupting normal transcription and translation of the IBRV tk gene. Based on the findings that the previously described IBRV $tk^-$ mutagen-induced mutants and $tk^-$ deletion mutants are safe and efficacious vaccines against IBR disease, it is believed that the IBRV $tk^-$ insertion mutants of the present invention will also be useful as vaccines against IBR disease. The development of this embodiment of the present invention is based in part on the description of the location of the IBRV tk gene and the nucleotide sequence thereof, and the enrichment and selection procedures developed for isolating the IBRV $tk^-$ mutants described in U.S. Pat. Nos. 4,569,840 and 4,703,011. That is, prior to U.S. Pat. No. 4,703,011, it had not been possible to develop IBRV mutants that fail to produce any functional thymidine kinase as a result of an insertion in the IBRV tk gene because in the art (1) the location of the IBRV tk gene on the physical map of IBRV DNA was not known; (2) the approximate boundaries of the nucleotide sequences delineating the coding region of the IBRV tk gene were not known; and (3) the restriction nuclease sites within the IBRV tk gene to allow appropriate insertions to be made in a cloned IBRV tk gene were not known. In addition, prior to U.S. Pat. Nos. 4,569,840 and 4,703,011, it was not known in the art what selection drugs were advantageous for enrichment and selection procedures. As a result, prior to U.S. Pat. Nos. 4,569,840 and 4,703,011, there was insufficient information to engineer and isolate an insertion mutant in the IBRV tk gene.

IV. Distinguishing Vaccinated From Infected Animals

The temperature-resistance and $tk^-$ characteristics of the IBRV mutants discussed above greatly improves their safety and usefulness as vaccines. However, the dormancy feature of IBRV still makes it difficult to effect eradication of IBR through the application of quarantine measures which are intended to prevent the spread of IBR by the isolation of IBRV-infected herds and the slaughter of IBRV-infected animals. That is, with existing MLV IBR vaccines, it is impossible to determine, by simple blood tests, whether a specific animal, which does not show symptoms of illness, is a carrier of a dormant IBRV. This is because usage of most current vaccines masks infections. Hence, since animals which appear healthy may actually be carriers and, thus, spreaders of IBRV, it is important to be able, even after vaccination, to identify infected animals and herds so as to be able to apply quarantine measures.

In addition, some countries require that imported livestock, whether for breeding, for stocking of farms, or for market, be tested and shown not to be carriers of IBRV, i.e., the animals cannot be imported unless they are seronegative for IBRV. With current killed and MLV IBR vaccines, a producer who elects to protect his animals from the diseases which accompany the stresses of shipping, or who is forced by the circumstances of IBR infection in an endemic region to vaccinate susceptible animals, finds himself at a severe economic disadvantage. This is because vaccination of the stock with current killed and MLV IBR vaccines results in a positive serological test for IBRV. Revaccination to enhance protection further increases IBRV antibody titers. As a result, the farmer's ability to export valuable livestock and to sell his stock at home is restricted and he is at a disadvantage whether he vaccinates or does not vaccinate. Hence, an IBR vaccine is needed that can be administered safely, can protect animals from disease and dormant infections caused by field strains of IBRV, has a low or nonexistent probability of reversion to virulence, and yet, does not produce a positive serological test for IBRV. Such a vaccine would allow exportation of livestock and vaccination programs to be pursued unhindered by the fear of quarantine. A producer could then minimize losses within his own herd, while animal health authorities could continue with their respective control measures.

To meet the needs discussed above, e.g., the IBRV(NG)dltk vaccine described in U.S. Pat. No. 4,703,011 was further modified to produce vaccines, such as IBRV(NG)dltkdlgIII (ATCC No. VR 2181), described in U.S. patent application Ser. No. 116,197, filed Nov. 3, 1987, which U.S. application is incorporated by reference herein in its entirety. This IBR vaccine not only fails to produce any functional TK as a result of a deletion in the IBRV tk gene but also fails to produce any antigenic IBRV gIII polypeptides as a result of a deletion in the IBRV gIII gene. The IBRV gIII gene has been found to be a useful serological marker for IBRV infections.

V. Viral Based Vectors

During the last few years, recombinant DNA technology has permitted the construction of chimeric viruses which express genetic information from more than one origin.

A variety of unique viral based vectors have been developed such as adenovirus based vectors (Ruether, J. E. et al, *Mol. Cell. Biol.*, 6:123–133 (1986); and Haj-Ahmad, Y. et al, *J. Virol.*, 57:267–274 (1986)) as well as herpes simplex virus based vectors (Smith, M. et al, *Proc. Natl. Acad. Sci. USA*, 81:5867–5870 (1984); and Smiley, J. R. et al, *J. Virol.*, 61:2368–2377 (1987)), *Herpes saimiri* virus based vectors (Desrosiers, R. C. et al, *Mol. Cell. Biol.*, 5:2796–2803 (1985)), baculovirus based vectors (van Wyke Coelingh, K. L. et al, *Virol.*, 160:465–472 (1987); Miyamoto, C. et al, *Mol. Cell. Biol.*, 5:2860–2865 (1985); Smith, G. E. et al, *Proc. Natl. Acad. Sci. USA*, 82:8404–8408 (1985); Smith, G. E. et al, *Mol. Cell. Biol.*, 3:2156–2165 (1983); Matsuura, Y. et al, *J. Gen. Virol.*, 68:1233–1250 (1987); and Kang, C. Y. et al, *J. Gen. Virol.*, 68:2607–2613 (1987)), and nuclear polyhedrosis virus based vectors (Hu, S. -L. et al, *J. Virol.*, 61:3617–3620 (1987); and Marumoto, Y. et al, *J. Gen. Virol.*, 68:2599–2606 (1987)).

The use of viral based vectors as vaccines is advantageous over subunit vaccines because replication of the viral based vectors within the host amplifies the amount of foreign antigen being expressed thereby, often increasing both cell-mediated and humoral immunogenic responses to the foreign antigen. In addition, the expression of foreign antigens within infected cells of the immunized host provides for post-translational modifications of the foreign antigen and thus antigen presentation more closely resembling those occurring during natural infection with the pathogen from which the foreign antigen is derived. Further, the use of safe, live-attenuated virus as vectors allows for the immunization against the pathogen from which the foreign antigen is derived.

The most extensively developed and exploited viral based vectors are the vaccinia virus based vectors (Mackett, M. et al, *Proc. Natl. Acad. Sci. USA*, 79:7415–7419 (1982); Panicali, D. et al, *Proc. Natl. Acad. Sci. USA*, 79:4927–4931 (1982); and Fuerst, T. R. et al, *Mol. Cell. Biol.*, 7:2538–2544 (1987)). Vaccinia virus based vectors which have been described include those which are useful as vaccines for hepatitis B (Smith, G. L. et al, *Nature*, 302:490–492 (1983);

and Cheng, K.-C. et al, *J. Virol.,* 61:1286–1290 (1987)); rabies (Kieny, M. P. et al, *Nature,* 312:163–166 (1984); and Wiktor, T. F. et al, *Proc. Natl. Acad. Sci. USA,* 81:7194–7198 (1984)); malaria (Smith, G. L. et al, *Science,* 224:397–399 (1984)); human respiratory syncytial virus (King, A. M. Q. et al, *J. Virol.* 61:2885–2890 (1987); human parainfluenza virus type 3 (Spriggs, M. K. et al, *J. Virol.,* 61:3416–3423 (1987)); rotavirus SA11 (Andrew, M. E. et al, *J. Virol.,* 61:1054–1060 (1987)); influenza (Smith, G. L. et al, *Proc. Natl. Acad. Sci. USA,* 80:7155–7159 (1983); Smith, G. L. et al, Virol., 160:336–345 (1987)); herpes simplex virus (Paoletti, E. et al, *Proc. Natl. Acad. Sci. USA,* 81:193–197 (1984); Gillespie, J. M. et al, *J. Clin. Microbiol.,* 23:283–288 (1986); and Sullivan, V. et al, *J. Gen. Virol.,* 68:2587–2598 (1987)); vescicular stomatitis virus (Mackett, M. et al, *Science,* 227:433–435 (1985)); human immunodeficiency virus envelope proteins (Chakrabarti, S. et al, *Nature,* 320:535–537 (1986); Hu, S. -L. et al, *Nature,* 320:537–540 (1986); and Hu, S. -L. et al, *Nature,* 328:721–723 (1987)); and Friend murine leukemia virus envelope proteins (Earl, P. L. et al, *Science,* 234:728–731 (1986)). A vaccinia based viral vector which expresses the coding gene sequences of the PRV g92 gene has also been described (Robbins, A. K. et al, European Pat. Publication No. 0,162,738). In addition, vaccinia-based viral vectors which express host genes, such as murine interleukin-2 (Ramshaw, I. A. et al, *Nature,* 329: 545–546 (1987)) and murine Class I major histocompatibility complex antigen H-2K$^d$, have been reported (Coupar, B. E. H. et al, *Proc. Natl. Acad. Sci. USA,* 83:7879–7882 (1986)).

Viral based vectors offer several significant advantages. First, immunization against more than one disease is possible with a single virus strain. This creates economy of production. Second, for many vaccines, two or more different modified-live viruses cannot be employed in combination in a single formulation because the replication of the viruses in the host causes mutual interference, and thereby impairs immunization. This situation is circumvented with viral based vectors because there is only a single replicating genome. Third, vaccines against causative agents of infectious disease, such as viruses and bacteria, for which vaccines have not previously been available or feasible, may for the first time be developed using viral based vectors which express the antigens of the causative agents of infectious disease. This is because the only component of the causative agents of infectious disease which is carried by the viral based vector is the gene coding for the antigen of the causative agent of disease which is responsible for eliciting immunity. Other components of the causative agents of infectious disease that are responsible for the pathobiology of the disease are eliminated from the viral based vector.

Although there is evidence that genetically engineered vaccinia viruses have reduced pathogenicity, there are several major obstacles to their general use as vaccines. First, severe complications can occur after vaccination, especially in immunodeficient individuals. Second, they are highly infectious for many animal species and humans. The insertion of genes from heterologous virus species into vaccinia-based viral vectors could alter the recombinant vaccinia virus host range or tissue tropism. Therefore, as agents, vaccinia virus based vectors pose potential health hazards. Third, there is no purpose served in vaccinating animals against smallpox, i.e., the disease that vaccinia protects against. Finally, potential recombination events between vaccinia and indigenous animal pox viruses might regenerate virulence of the vaccinia virus which will cause smallpox disease in humans.

IBRV-based viral vectors have distinct advantages over vaccinia-based viral vectors for the vaccination of cattle because they (1) protect cattle against the important bovine diseases of IBR and IPV; and (2) are host-limiting, i.e., they do not infect humans.

In embodiments of the present invention, IBRV has been utilized as the basis for viral based vectors. IBRV is a typical alpha herpesvirus with a genome consisting of linear double-stranded DNA molecules approximately 135–140 kilobases (hereinafter "kb") in size. Like vaccinia and like other herpesviruses, IBRV can tolerate nucleotide sequence deletions of 4 kb or more, and can tolerate foreign DNA insertions of 5–10 kb or more.

Prior to U.S. Pat. No. 4,703,011 and U.S. patent application Ser. No. 116,197, filed Nov. 3, 1987, now U.S. Pat. No. 4,992,051 it was not possible to develop IBRV-based viral vectors because there was no knowledge of the location of suitable, insertion sites, i.e., non-essential IBRV genes, which could be employed for the insertion of foreign genes. U.S. Pat. No. 4,703,011 and U.S. patent application Ser. No. 116,197, filed Nov. 3, 1987, however, identified the location of the IBRV tk and IBRV gIII genes on the physical map of IBRV DNA and demonstrated that they were not essential for virus replication in cultured cells. Hence, suitable insertion sites for foreign genes became known for the first time. Furthermore, U.S. Pat. No. 4,703,011 and U.S. patent application Ser. No. 116,197, filed Nov. 3, 1987, now U.S. Pat. No. 4,992,051 described for the first time the nucleotide sequences of the coding regions, the promoter regions, the translation start and stop signals, and the polyadenylation signals of the IBRV tk and IBRV gIII genes.

In the present invention, the isolation of IBRV DNA fragments containing IBRV gene promoters and the ligation of IBRV promoters to the coding nucleotide sequences of foreign genes has been described for the first time. Further, it has been determined for the first time in the present invention that in IBRV-based viral vectors, the foreign gene can be expressed by a foreign gene promoter and does not require an IBRV promoter for expression. Thus, for the first time in the present invention, it has been possible to develop IBRV-based viral vectors.

SUMMARY OF THE INVENTION

An object of the present invention is to provide an IBR vaccine effective in controlling the spread of IBR disease in its various manifestations.

Another object of the present invention is to provide an IBR vaccine wherein the vaccine can be safely and efficaciously administered intramuscularly, intranasally or intravaginally.

Still another object of the present invention is to provide an IBR vaccine wherein the vaccine can be administered safely to calves and to pregnant cows in all stages of pregnancy.

Another object of the present invention is to provide an IBR vaccine wherein the animal vaccinated with such is less likely to become a carrier of either another IBRV vaccine strain or any IBRV field strain.

Still another object of the present invention is to provide an IBRV-based viral vector which is distinguishable from any IBRV field strain and from other IBRV vaccine strains.

A further object of the present invention is to provide an IBRV-based viral vector wherein animals vaccinated with such can be distinguished from animals infected with any IBRV field strain or vaccinated with other IBRV strains.

A still further object of the present invention is to provide an IBRV-based viral vector which fails to produce any antigenic IBRV gIII polypeptides as a result of a deletion and/or insertion mutation in the IBRV gIII gene.

An even further object of the present invention is to provide an IBRV-based viral vector which fails to produce any functional IBRV TK activity as a result of a deletion and/or insertion mutation in the IBRV tk gene.

Yet an even further object of the present invention is to provide an IBRV-based viral vector in which a foreign gene is inserted at the site of a non-essential one IBRV and in which the foreign gene is expressed.

Another object of the present invention is to provide an IBRV-based viral vector virus which cannot revert to $tk^+$, is easily distinguished from a $tk^+$ virus, cannot revert to $gIII^+$ and easily distinguished from a $gIII^+$ virus.

Still another object of the present invention is to provide an IBRV-based viral vector which can replicate efficiently at temperatures ranging from 34.5° C. to 40° C., i.e., inclusive of temperature-resistant viruses.

An additional object of the present invention is to provide methods for the production of IBRV-based viral vectors which contain deletion and/or insertion mutations in the IBRV tk, IBRV gIII genes and in other IBRV genes.

Another object of the present invention is to provide an IBRV-based viral vector wherein foreign DNA may be inserted in either the IBRV tk, IBRV gIII genes or in other IBRV genes.

Still another object of the present invention is to provide an IBRV-based viral vector that expresses a major pseudorabies virus glycoprotein antigen so that cattle vaccinated with the same may obtain protection from fatal infections by pseudorabies virus.

A still further object of the present invention is to provide methods for the production of an IBRV-based virus vector in which the expression of the foreign gene is driven by a foreign gene promoter or an IBRV gene promoter.

Other objects of the present invention will be apparent from the detailed description of the invention hereinafter.

In one embodiment of the present invention, the above-described objects have been met by an IBRV which fails to produce any functional thymidine kinase as a result of insertion in the IBRV tk gene and a vaccine for IBR disease comprising: (1) a pharmaceutically acceptable amount of said virus; and (2) a pharmaceutically acceptable carrier or diluent.

In another embodiment of the present invention, the above-described objects have been met by a process for producing an IBRV which fails to produce any functional thymidine kinase as a result of an insertion in the IBRV tk gene comprising:

(1) constructing a hybrid plasmid comprising a cloning vector and a DNA fragment of IBRV containing substantially all of the IBRV tk gene and flanking sequences thereof;

(2) inserting a foreign DNA sequence within the coding region of the IBRV tk gene of the hybrid plasmid of step (1);

(3) co-transfecting, in $tk^+$ IBRV host cells, the hybrid plasmid of step (2) and infectious DNA from a $tk^+$ IBRV; and (4) selecting or screening, in $tk^-$ IBRV host cells, for $tk^-$ IBRV from the virus produced in step (3) so as to produce an IBRV mutant which fails to produce any functional thymidine kinase as a result of an insertion in the IBRV tk gene.

In yet another embodiment of the present invention, the above-described objects have been met by the above-described process additionally comprising step (5):

(5) propagating the resulting IBRV of step (4) at a non-permissive temperature for a temperature-sensitive virus so as to select for and produce temperature-resistant IBRV mutants which fail to produce any functional thymidine kinase as a result of an insertion in the IBRV tk gene.

In still another embodiment of the present invention, the above-described objects have been met by an IBRV-based viral vector comprising an IBRV having inserted therein a foreign gene adjacent to an IBRV gene promoter such that the expression of said foreign gene is controlled by the IBRV gene promoter or comprising an IBRV having inserted therein a foreign gene adjacent to a foreign gene promoter such that the expression of said foreign gene is controlled by the foreign gene promoter.

In a preferred embodiment, the IBRV-based viral vector is an IBRV $tk^-$ deletion mutant and/or an IBRV gIII deletion mutant and the coding sequence of the foreign gene plus its 3' downstream sequences are inserted adjacent to an IBRV gene promoter such that the expression of said foreign gene is controlled by the IBRV gene promoter and the resulting IBRV mutant expresses the foreign gene.

In another embodiment, the above described objects have been met by a process for producing an IBRV-based viral vector comprising:

(1) constructing a hybrid plasmid comprising a cloning vector and a DNA fragment of IBRV containing substantially all of a non-essential IBRV DNA sequence and flanking sequences thereof;

(2) inserting a foreign gene within the non-essential IBRV DNA sequence of the hybrid plasmid of step (1) such that the expression of said foreign gene is controlled by either an IBRV gene promoter or by a foreign gene promoter and such that the resulting IBRV mutant of step (4) expresses said foreign gene;

(3) co-transfecting, in IBRV host cells, the hybrid plasmid of step (2) and infectious DNA from an IBRV such that homologous recombination between the infectious DNA and the hybrid plasmid of step (2) occurs through common IBRV DNA sequences flanking the insertion in the hybrid plasmid of step (2); and (4) selecting or screening for an IBRV mutant which expresses the gene product of said foreign gene, so as to produce an IBRV-based vital vector which expresses said foreign gene.

In a preferred embodiment, there is an additional step which is carried out just prior to or after step (4) comprising selecting or screening for an IBRV mutant which fails to produce the gene product of said non-essential IBRV DNA sequence such that the resulting IBRV-based viral vector of step (4) also fails to produce the gene product of the non-essential IBRV DNA sequence.

BRIEF DESCRIPTION OF THE DRAWINGS

FIG. 6 shows the restriction endonuclease maps of the KpnI to HindIII fragments from pLAHK and pLAHKdlApaI pLAHK contains the IBRV gIII gene. pLAHKdlApaI is obtained by deletion of ApaI fragments for pLAHK. The coding region of the IBRV gIII gene is removed from the IBRV gIII gene by the ApaI deletion (U.S. patent application Ser. No. 116,197, filed Nov. 3, 1987). These restriction endonuclease maps show the IBRV gIII promoter region, the translational start (ATG) and stop (TAG) signals, and the polyadenylation (AATAAA) signal. Also shown in FIG. 6 is the restriction endonuclease maps of the BamHI to PvuII fragment from pSP64/PRVtk which contains the coding region of the PRV tk gene. pSP64/PRVtk was constructed by cloning the 2.2 kb BamHI to PvuII fragment of pBB-11 (U.S. Pat. No. 4,514, 497) at the unique BamHI And SmaI sites of pSP64 (Promega Biotech 1985/1986 catalogue; U.S. Pat. No. 4,703,011). The coding region of the PRV tk gene and the PRV sequence 3' to the PRV tk gene were inserted adjacent to the IBRV gIII promoter in pLAHKdlApaI to produce pLAHKdlApaI/PRVtk by: (1) cleaving pLAHKdlApaI with BamHI so as to separate the IBRV gIII promoter from the IBRV gIII coding sequences; (2) cleaving pSP64/PRVtk with BamHI and KpnI; (3) ligating the BamHI termini of the cleaved plasmids so as to place the PRV tk gene coding region adjacent to the IBRV gIII promoter; (4) treating the overhanging KpnI and BamHI termini of the resulting reaction mixture with Mung bean nuclease to produce blunt ends; and (5) ligating the blunt ends to produce pLAHKdlApaI/PRVtk. Homologous recombination between pLAHKdlApaI/PRVtk and infectious DNA from IBRV(NG)dltkdlgIII (U.S. Pat. No. 4,711,850 and U.S. patent application Ser. No. 116,197, filed Nov. 3, 1987) gave rise to IBRV(NG)dltkdlgIII(PRVtk) which expresses the PRV tk gene from the IBRV gIII promoter.

FIG. 10 shows that the recombinant IBRV viruses produced $^3H$-mannose-labeled proteins of about 92,000 to 97,000 daltons and about 72,000 daltons (PRV g92 and a partially glycosylated precursor) which reacted with the PRV-specific antisera, but the $^3H$-mannose-labeled extracts from parental $tk^+$ IBRV(Los Angeles) did not react with the anti-PRV sera 18705. The mobilities of molecular weight markers are shown at the right of the figure.

FIG. 11 shows that the recombinant IBRV viruses and PRV(BUK-d13) produced $^3H$-mannose-labeled proteins of about 92,000 to 97,000 daltons (PRV g92) (lanes 2–4), which reacted with the anti-PRV g92 monoclonal antibodies, but that extracts from $^3H$-mannose-labeled, mock-infected cells (lane 1) did not react with the anti-PRV g92 monoclonal antibodies. The mobilities of molecular weight markers are shown at the right of the figure.

DETAILED DESCRIPTION OF THE INVENTION

Figure 1:
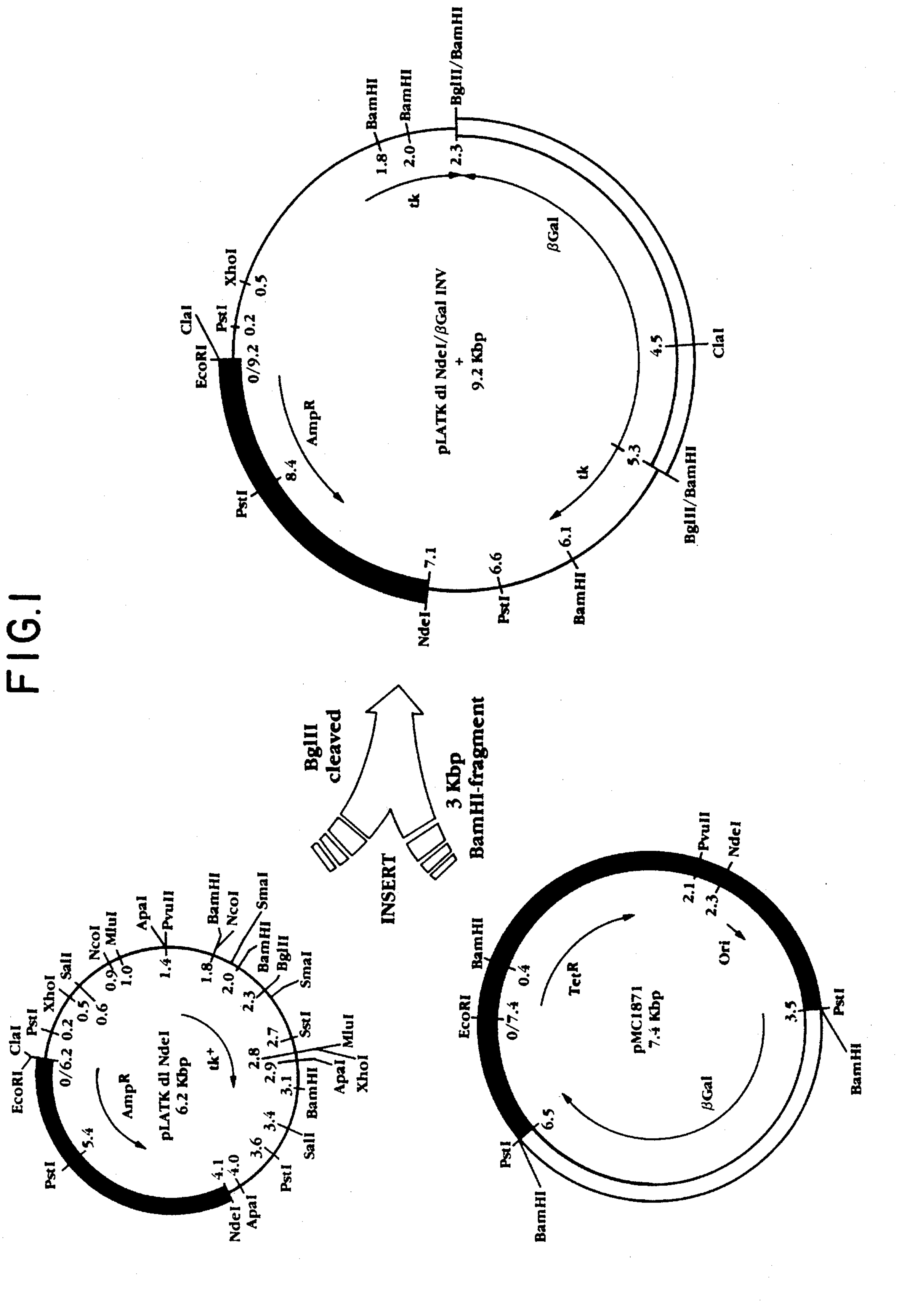
FIG. 1 schematically illustrates, by example, restriction endonuclease maps of the plasmids used to construct pLAT-KdlNdeI/βGalINV, which contains the *E. coli* lacZ gene inserted into the IBRV tk gene in the opposite orientation from the promoter sequence of the IBRV tk gene. pLAT-KdlNdeI was constructed by deleting a 1.2 kb NdeI nucleotide sequence from pLATK. pLATK was constructed by ligating a 5.1 kb StuI/ClaI fragment of IBRV DNA, which contains the IBRV tk gene, to the 2.3 kb PvuII/ClaI fragment of pBR322 (U.S. Pat. No. 4,703,011). pMC1871 is a derivative of pBR322 containing the *E. coli* lacZ gene inserted as a 3.0 kb PstI fragment at the PstI site of pBR322 (Casadaban, M. J., *Methods in Enzymology,* 11:293 (1983)). pLATKdlNdeI/βGalINV was constructed by cleaving pLATKdlNdeI with BglII, cleaving pMC1871 with BamHI, and then inserting the 3.0 kb BamHI fragment from pMC1871, which contains the *E. coli* lacZ gene, at the unique BglII cleavage site of pLATKdlNdeI. The black bars represent pBR322 sequences, the white bars represent *E. coli* lacZ gene sequences, and the solid lines represent IBRV DNA sequences.

As discussed above, in one embodiment of the present invention, the above-described objects have been met by an IBRV which fails to produce any functional thymidine kinase as a result of an insertion in the IBRV tk gene and a vaccine for IBR disease comprising: (1) a pharmaceutically acceptable amount of said virus; and (2) a pharmaceutically acceptable carrier or diluent.

In another embodiment of the present invention, the above-described objects have been met by a process for producing an IBRV which fails to produce any functional thymidine kinase as a result of an insertion in the IBRV tk gene comprising:

(1) constructing a hybrid plasmid comprising a cloning vector and a DNA fragment of IBRV containing substantially all of the IBRV tk gene and flanking sequences thereof;

(2) inserting a foreign DNA sequence within the coding region of the IBRV tk gene of the hybrid plasmid of step (1);

(3) co-transfecting, in $tk^+$ IBRV host cells, the hybrid plasmid of step (2) and infectious DNA from a $tk^+$ IBRV; and (4) selecting or screening, in $tk^-$ IBRV host cells, for $tk^-$ IBRV from the virus produced in step (3) so as to produce an IBRV mutant which fails to produce any functional thymidine kinase as a result of an insertion in the IBRV tk gene.

In yet another embodiment of the present invention, the above-described objects have been met by the above-described process additionally comprising step (5):

(5) propagating the resulting IBRV of step (4) at a non-permissive temperature for a temperature-sensitive virus so as to select for and produce temperature-resistant IBRV mutants which fail to produce any functional thymidine kinase as a result of an insertion in the IBRV tk gene.

In still another embodiment of the present invention, the above-described objects have been met by an IBRV-based viral vector comprising an IBRV having inserted therein a foreign gene adjacent to an IBRV gene promoter such that the expression of said foreign gene is controlled by the IBRV gene promoter or comprising an IBRV having inserted therein a foreign gene adjacent to a foreign gene promoter such that the expression of said foreign gene is controlled by the foreign gene promoter.

In a preferred embodiment, the IBRV-based viral vector is an IBRV $tk^-$ deletion mutant and/or an IBRV gIII deletion mutant and the coding sequence of the foreign gene plus its 3' downstream sequences are inserted adjacent to an IBRV gene promoter such that the expression of said foreign gene is controlled by the IBRV gene promoter and the resulting IBRV mutant expresses the foreign gene.

In another embodiment, the above described objects have been met by a process for producing an IBRV-based viral vector comprising:

(1) constructing a hybrid plasmid comprising a cloning vector and a DNA fragment of IBRV containing substantially all of non-essential IBRV DNA sequence and flanking sequences thereof;

(2) inserting a foreign gene within the non-essential IBRV DNA sequence of the hybrid plasmid of step (1) such that the expression of said foreign gene is controlled by either an IBRV gene promoter or by a foreign gene promoter and such that the resulting IBRV mutant of step (4) expresses said foreign gene;

(3) co-transfecting, in IBRV host cells, the hybrid plasmid of step (2) and infectious DNA from an IBRV such that homologous recombination between the infectious DNA and the hybrid plasmid of step (2) occurs through common IBRV DNA sequences flanking the insertion in the hybrid plasmid of step (2); and (4) selecting or screening for an IBRV mutant which expresses the gene product of said foreign gene, so as to produce an IBRV-based viral vector which expresses said foreign gene.

In a preferred embodiment, there is an additional step which is carried out just prior to or after step (4) comprising selecting or screening for an IBRV mutant which fails to produce the gene product of said non-essential IBRV DNA sequence such that the resulting IBRV-based viral vector of step (4) also fails to produce the gene product of the non-essential IBRV DNA sequence.

As used herein, a "foreign DNA sequence" means (1) any DNA sequence which does not encode a gene, i.e., a noncoding DNA sequence, regardless of origin, such as a viral, eucaryotic, or procaryotic noncoding sequence and inclusive of oligonucleotide linkers; (2) any DNA sequence which encodes a foreign gene, i.e., a coding DNA sequence; or (3) any coding IBRV DNA sequence which has been translocated from its normal location on the IBRV genome to another location on the IBRV genome, such as the IBRV gI gene translocated into the IBRV gIII gene or IBRV tk gene. As used herein, a "foreign gene" means (2) and (3) above from the definition of a "foreign DNA sequence". The preferred "foreign gene" is (2) above for the definition of a "foreign DNA sequence".

The foreign gene which can be employed in the present invention is not critical thereto and can be the *E. coli* lacZ gene and the transposon Tn5 gene ($neo^R$) in addition to complete or partial genes for antigens or antigenic portions thereof, of causative agents of infectious diseases.

For example, the foreign genes which can be employed are those which code for surface proteins, i.e., antigens which elicit neutralizing antibodies against enveloped viruses which are significant pathogens for cattle, such as the vesicular stomatitis virus G gene (Mackett, M. et al, *Science,* 227:433–435 (1985)); the rabies virus G gene (Viktor, T. J. et al, *Proc. Natl. Acad. Sci. USA,* 81:7194–7198 (1984)); the hemagglutinin (HA) and fusion (F) genes of rinderpest virus (Walsh, J., *Science,* 237:1289–1291 (1987)); the hemagglutinin and neuraminidase genes of bovine type 3 parainfluenza virus (Coelingh, K. L. et al, *J. Virol.,* 60:90–96 (1986)); the envelope gene of bovine leukemia virus (Rice, N. R., *Virol.,* 138:82–93 (1984)); and the glycoprotein genes of pseudorabies virus (Kit, S. et al, *Am. J. Vet. Res.,* 48:780–793 (1987)).

In addition, foreign genes which can be employed are those which code for surface proteins, i.e., antigens, which elicit neutralizing antibodies and immunity against nonenveloped viruses which are significant pathogens of cattle, such as foot and mouth disease virus capsid protein VPI gene (Weddell, G. N. et al, *Proc. Natl. Acad. Sci. USA,* 82:2618–2622 (1985)); and bovine parvovirus capsid protein C gene (Smith, S. et al, *Biotech,* 3:715–720 (1985); Durham, P. J. K. et al, *Vet. Microbiol.,* 10:165–177 (1984/1985)).

Examples of other virus diseases of cattle in which viral genes for critical protective antigens may be employed as the foreign genes which are incorporated into the genome of IBRV to produce IBRV-based viral vectors according to the present invention are bovine diarrhea virus (a togavirus), bovine ephemeral fever virus (a rhabdovirus) and the bovine corona- and rotaviruses that cause diarrhea (Fenner, F. et al, In: *Vet. Virol.* (Academic Press, Inc., New York (1987)); Kahrs, R. F. et al, *J. Am. Vet. Med. Assoc.,* 163:437–441 (1973 ); Fulton, R. W. et al, *Am. J. Vet. Res.,* 43:1454–1457 (1982); Brako, E. et al, *Am. J. Vet. Res.,* 45:813–816 (1984); Rottier, P. J. M. et al, *J. Virol.,* 61:2042–2045 (1987); Ohmann, H. B. et al, *J. Gen. Virol,* 68:1971–1982 (1987); Renard, A. et al, DNA, 4:429–438 (1985); Harkness, J. W., *Ann. Rech. Vet.,* 18:167–174 (1987); Beck, E. et al, *J. Virol.,* 61:1621–1629 (1987); Tsukiyama, K. et al, *Virol.,* 160:48–54 (1987); Willems, L. et al, *Virol.,* 160:55–59 (1987)).

Other examples of foreign genes include genes of *Babesia bovis* and *Babesia bigemina*, hemoprotozoa which infect livestock in many tropical countries; *Anaplasma marginale*, another hemoprotozoan; *Brucella bovis*, a bacterium of significant zoonotic importance in many areas of the world; the Pasteurella spp bacteria associated with shipping fever; and *E. coli*, the bacteria of scours.

As discussed above, noncoding foreign DNA sequences include oligonucleotide linkers. The size of the oligonucleotide linkers is not critical to the present invention. Generally, the size of the oligonucleotide linkers is 8 to 10 nucleotides in length, but can be longer, e.g., about 50 nucleotides, or shorter, e.g., 4, 5 or 7 nucleotides. The preferred length of the oligonucleotide linker is about 8 to 10 nucleotides in length. The DNA sequence of the oligonucleotide linker is also not critical to the present invention.

Similarly, the size and sequences of other foreign DNA sequences employed in the present invention is not critical. Generally, the size of foreign DNA sequences, other than oligonucleotide linkers, is about 0.5 to 5 kb in length. For example, the ($neo^R$) gene is about 1.0 kb in length and the *E. coli* lacZ gene is about 3.0 kb in length.

As used herein, a "non-essential IBRV DNA sequence" means a region of the IBRV genome which is not required for viral replication, i.e., a non-essential IBRV gene or a noncoding region of the IBRV genome. The preferred non-essential IBRV DNA sequence is a non-essential IBRV gene.

The non-essential IBRV DNA sequences employed in the present invention is not critical thereto. Examples of such non-essential IBRV DNA sequences include the following non-essential IBRV genes: the IBRV tk gene and the IBRV gIII gene.

Foreign DNA sequences inserted into the IBRV tk gene, IBRV gIII gene and other non-essential IBRV DNA sequences will only be expressed as a functional protein if the appropriate gene expression control signals are present. These signals consist of two types: those that control levels of mRNA and those that control efficiency of mRNA translation into protein.

The levels of mRNA are determined by transcription rates, mRNA processing efficiency, and mRNA degradation rates. Relatively little is currently understood about the molecular control of the latter two parameters; however, the control signals which regulate transcription are better defined. Transcription, which is the process whereby mRNA is synthesized off a DNA template, occurs through interaction of RNA polymerase, and accessory protein factors with particular DNA sequences of the template. The sets of DNA sequences which bind RNA polymerase and control the site and onset of initiation of mRNA are collectively referred to as the promoter region.

The foreign gene promoter employed in the present invention may be the native promoter of the foreign gene or another foreign gene promoter and is preferably an animal cellular or viral gene promoter. The animal cellular and viral gene promoters are ones which are trans-activated by the immediate-early IBRV genes so as to drive the expression of foreign genes inserted in IBRV-based viral vectors.

The specific animal cellular gene promoter is not critical to the present invention. The animal cellular gene promoter can be derived from, for example, the human or rabbit hemoglobin genes or the human heat-shock protein (Feldman, L. T. et al, *Proc. Natl. Acad. Sci. USA,* 79:4952–4956 (1982)).

The specific viral gene promoter is also not critical to the present invention. The viral gene promoter can be derived from, for example, herpesviruses or adenoviruses (Ahlers, S. E. et al, *J. Virol.,* 61:1103–1107 (1987); Campbell, M. E. M. et al, *Virol.,* 157:307–316 (1987); Everett, R. D. et al, *Nucl. Acids Res.,* 12:5969–5978 (1984); Feldman, L. T. et al, *Proc. Natl. Acad. Sci. USA,* 79.:4952–4956 (1982); and U.S. patent application Ser. No. 857,703, filed Apr. 29, 1986 now U.S. Pat. No. 4,999,296). The preferred viral gene promoter is a herpesvirus gene promoter such as that of herpes simplex virus, pseudorabies virus, varicella-zoster virus, cytomegalovirus, Epstein-Barr virus and equine herpesvirus type 1.

The specific IBRV gene promoter employed in the preferred embodiments of the present invention to drive the expression of foreign genes is not critical thereto and can include, for example, the promoter for an "immediate early" IBRV gene or the IBRV tk "early" gene promoter, or the IBRV gIII "late" gene promoter. The IBRV "immediate early" and "early" promoters and the "late" IBRV gIII gene promoter can be derived from the hereinafter described $tk^+$ IBRV strains as well as $tk^-$ IBRV strains. The IBRV tk gene promoter is located in the 400 bp PvuII to NcoI fragment upstream from the translational start site of the IBRV tk gene (see FIG. 4, pLATKdlNdeI, map units of 1.4 to 1.8; U.S. Pat. No. 4,703,011). The IBRV gIII gene promoter is located in the 650 bp BglII to NcoI fragment upstream from the ATG translational start signal of the IBRV gIII gene (see FIG. 5; U.S. Pat. No. 4,703,011).

The efficiency of translation of the mRNA is determined by the sequence and length of the leader mRNA fragment which precedes the start codon of the coding sequence, and by the presence of a short consensus sequence flanking the start codon called "Kozak's" sequence. There is great variation in the DNA sequences of promoters for different genes from a variety of species. Even within the herpesvirus genome, there are few if any recognizable common features within the DNA sequences of different viral gene promoters. Detailed functional studies of several eucaryotic promoters have demonstrated the common occurrence of canonical consensus sequences, the TATA site which determines the point of initiation of the mRNA, and the CAAT box, which effects transcription efficiency. In addition, there are upstream distal signals which further modulate transcription efficiencies. The IBRV tk and gIII gene promoters have the canonical consensus CAAT signal described above and AT-rich sequences which appear to serve as putative TATA signals.

Foreign DNA sequences coding open reading frames that are inserted into the IBRV tk and gIII genes may be expressed as fusion proteins off of the IBRV gene promoters if the inserted coding sequences are in phase with the IBRV gene coding sequences, and if no stop codons are interposed. However, IBRV-based viral vectors of this type are not preferred because fusion proteins are sometimes less immunogenic than native forms.

The method of inserting the foreign DNA sequence into the cloning vector will depend upon the type of foreign DNA sequence used. Palindromic double-stranded linkers containing one or more restriction nuclease sites in the oligonucleotide sequence (New England Biolabs) may be inserted by well known procedures (Maniatis, T. et al, *Mol. Cloning,* Cold Spring Harbor Laboratory (1982)). Foreign DNA sequences may also be inserted in plasmid DNA by tailing ends with complementary homopolymers using terminal transferase (Maniatis, T. et al, *Mol. Cloning*, Cold Spring Harbor Laboratory (1982)). By the judicious choice of foreign DNA sequence length, frame shift mutations may be produced in the non-essential IBRV gene, augmenting the effect of deletions within the non-essential IBRV gene.

The particular cloning vector employed in the present invention to construct the hybrid plasmid comprising a DNA fragment of IBRV containing substantially all of the IBRV non-essential DNA sequence, e.g., the IBRV tk gene, and flanking sequences thereof of step (1) is not critical to the present invention as long as the cloning vector contains a gene coding for a selective trait, e.g., drug resistance. Examples of such cloning vectors include pBR322 and pBR322-based vectors (Sekiguchi, T. et al, *Gene,* 21:267–272 (1983)), pMB9, pBR325, pKH47, pUC18 and pUC19 (Bethesda Research Laboratories), pBR328 and pHC79 (Boehringer Manneheim Biochemicals), phage Charon 28 (Bethesda Research Laboratories), pKBll and pKSV-10 (P-L Biochemicals), pPROK-1, pYEJOO1, pKC30, pKT280, pEUK-C1, pEUK-C2, pMAM, pMAM-neo, pCHl110, pdBPV-MMTneo and pWE15 (Clontech Laboratories, Inc.), pMAR420 (Otsuka, H. et al, *Virol.,* 113:196–213 (1981)) and oligo(dG)-tailed pBR322 (New England Nuclear). pBR322 is one of the preferred cloning vectors in the present invention because the 11.1 kb HindIII-I fragment of IBRV contains the IBRV gIII gene and can be cloned in the single HindIII site of pBR322. Similarly, the 2.5 kb EcoRI to BamHI fragment contains the IBRV gIII gene and can be cloned at the unique BamHI and EcoRI sites of pBR322. pBR322 is also one of the preferred cloning vectors in the present invention because the 21.5 kb HindIII-A fragment contains the IBRV tk gene and can be cloned in the single HindIII site of pBR322 (see FIG. 2).

The specific host employed for growing the hybrid plasmids of the present invention is not critical to the present invention. Examples of such hosts include *E. coli* K12 RR1 (Bolivar, F. et al, *Gene,* 2:95–113 (1977)); *E. coli* K12 HB101 (ATCC No. 33694); *E. coli* MM21 (ATCC No. 336780); and *E. coli* DH1 (ATCC No. 33849). *E. coli* K12 RR1 is the preferred host and has an F hsd R hsd M genotype.

Similarly, alternative vector/cloning systems can be employed such as plasmid vectors which grow in *E. coli* or *Saccharomyces cerevisiae*, or both, or plasmid vectors which grow in *B. subtilus*, or even vectors such as bovine papilloma virus (ATCC No. 371112) which grow in animal cells such as mouse (ATCC No. CRL 1616) (Elder, J. T. et al, *Ann. Rev. Gen.,* 15:295–340 (1981); Ure, R. et al, *Meth. in Enzymol.,* "Recombinant DNA", Volume 101, Part C (Academic Press, New York) (1983)).

As used herein, "flanking sequences" means the sequences upstream, downstream or, both upstream and downstream, from the non-essential IBRV DNA sequence, e.g., the IBRV tk gene coding sequences. The upstream sequences for the non-essential IBRV gene contain the transcriptional control signals, i.e., promoters and enhancers, whereas the downstream sequences contain the transcription termination and polyadenylation signal of, for example, the IBRV tk gene.

The precise non-essential IBRV DNA sequence, e.g., the IBRV tk gene sequences which must be present in the hybrid plasmids of the present invention will depend upon the sequences chosen to be inserted and the restriction nucleases to be employed in the engineering of the insertion mutant.

The specific IBRV DNA sequences adjacent to the insertion in the hybrid plasmids required in steps (1) and (3) of the present invention will depend upon the specifics of the insertion in the hybrid plasmid. In general, the size of the IBRV DNA sequences adjacent to both the 3' and 5' sides of the insertion is at least 400 bp. For example, in pLATKdlN-deI/βGalINV (see FIG. 1) described in detail below, the 3' and 5' sequences on both sides of the βGal insertion are 1.8 kb and 2.3 kb in length, respectively. In the case of pSP65/IBRVtk/PRVg92 (see FIG. 3) described in detail below, the 3' and 5' sequences on both sides of the PRV g92 gene insertion are about 0.7 kb and 0.6 kb in length, respectively.

The specific $tk^+$ IBRV strain employed as a starting material in the present invention for the $tk^-$ IBRV insertion mutant embodiment of the present invention is not critical. Similarly, the specific $tk^+$ IBRV strain employed as a starting material for the IBRV-based viral vectors is not critical to the present invention.

Examples of such $tk^+$ IBRV strains include the following strains: Los Angeles strain (ATCC No. VR 188), Cooper strain (ATCC No. VR 864), IPV strain K22 (Kendrick, J. W. et al, *Cornell Vet.*, 48:458–495 (1958)), strains M03, M06, BFN-IH, BFN-IIN, BFN-IID, Gi 1 to 5, Bi, B4, BRV, LAE, V3 415, V3 416, V3 18, V3 93 (Gregersen, J. -P. et al, *Arch. Virol.*, 84:91–103 (1985)), BFA Wabu strain (Ackermann, M. et al, *Vet. Microbiol.*, 9:53–63 (1984)), strain P8-2 (Weinmaster, G. A. et al, *Virol.*, 118:191–201 (1982)), strains P10 and P34 (Engels, M. et al, *Arch. Virol.*, 67:169–174 (1981)), Alberta (Canada) isolates No. 1 to No. 122 (Misra, V. et al, *Arch. Virol.*, 76:341–354 (1983)), or IBRV(RTK-1B) (U.S. Pat. No. 4,703,011), all of which produce IBRV gIII. If the insertion is to be made in a non-essential IBRV DNA sequence other than the IBRV tk gene, it is preferable that the IBRV strain employed for recombination be a vaccine strain such that the resulting insertion mutant will possess the attenuated properties of the vaccine strain. The IBRV-(Los Angeles) strain is the preferred $tk^+$ IBRV strain from which the IBRV DNA fragment containing the IBRV $tk^-$ gene of step (1) is provided while the IBRV(RTK-1B) strain is the preferred $tk^+$ IBRV strain from which the infectious IBRV DNA of step (3) is derived for the $tk^+$ IBRV insertion mutant embodiment of the present invention. IBRV(RTK-1B) is the preferred $tk^+$ IBRV strain because it was derived from the attenuated IBRV(B8-D53) strain and has been further attenuated by the introduction of mutagen induced mutations such that the resulting IBRV mutant of step (4) possesses the resulting mutations found in IBRV(RTK-1B).

$tk^-$ IBRV strains can also be employed as a starting material for the IBRV-based viral vectors.

Examples of such $tk^-$ IBRV strains include the temperature-resistant IBRV(B8-D53) (ATCC No. VR 2066) and IBRV(NG)dltk (ATCC No. VR 2112) strains, which produce IBRV gIII, and the temperature resistant IBRV(NG)dltkdlgIII (ATCC No. VR 2181) strain which also fails to produce any antigenic IBRV gIII polypeptides. IBRV(NG)dltkdlgIII is the preferred $tk^-$ IBRV strain employed as a starting material for the IBRV-based viral vectors of the present invention because it contains a deletion in the IBRV tk gene such that it fails to provide any functional thymidine kinase, it contains a deletion in the IBRV gIII gene such that it fails to produce any antigenic IBRV gIII polypeptides and it is temperature resistant.

The specific IBRV host cells employed in the present invention are not critical so long as they allow for permissive growth of IBRV. Further, the IBRV host cells can be $tk^-$ IBRV host cells or $tk^+$IBRV host cells.

Examples of such $tk^+$ IBRV host cells include Rab-9 cells (ATCC No. CRL 1414); primary rabbit kidney cells; secondary rabbit kidney cells; rabbit cornea (SIRC) cells (ATCC No. CCL 60); rabbit kidney (LLC-RK1) cells (ATCC No. CCL 106); embryo bovine trachea (EBTR) cells (ATCC No. CCL 44); bovine turbinate (BT) cells (ATCC No. CRL 1390); Madin-Darby bovine kidney (MDBK) cells (ATCC No. CCL 22); and Georgia bovine kidney (hereinafter "BK") cells (Engels, et al, *Virus Res.*, 6:57–73 (1986/1987)). (The American Type Culture Collection Catalog indicates that some types of lamb, goat, cat and horse cells may also be permissive for IBRV(Los Angeles) (ATCC No. VR 188)). Rab-9 are the preferred $tk^+$IBRV host cells employed in the present invention. However, it should be noted that for the production of virus used for vaccination of animals in the field, a United States Department of Agriculture certified cell line permissive for IBRV, preferably of the same species as the animal to be vaccinated, and free of other infectious agents, should be used. For example, a suitable bovine cell line would be a certified diploid non-tumorigenic bovine turbinate, tracheal, or kidney cell line free of mycoplasma, and bovine diarrhea virus and other viruses.

An example of $tk^-$ IBRV host cells which can be employed and allow permissive growth of IBRV is the rabbit Rab(BU) cell line, which was derived from Rab-9 cells (Kit, S. et al, *Virol.*, 130:381–389 (1983)). Other $tk^-$ IBRV host cells of rabbit or bovine origin which can be employed in the present invention can be obtained by following, for example, the procedure previously used to isolate $tk^-$ mouse, human and rabbit cell lines (Kit, S. et al, *Exptl. Cell Res.* 31:297–312 (1963); Kit, S. et al, *Int. J. Cancer,* 1:19–30 (1966); Kit, S. et al, *Virol.*, 130:381–389 (1983)). An example of a $tk^-$ bovine cell line is the MDBK(BUlO100) cell line which was derived from Madin-Darby bovine kidney cells (Bello, J. et al, *J. Virol.*, 61:4023–4025(1987)). Rab(BU) cells are the preferred $tk^-$ IBRV host cells employed in the present invention not only because they permit the replication to high titers of both $tk^+$ and $tk^-$ IBRV strains, but also because they do not detectably revert to $tk^+$ in HATG media and they can be used for the plaque titration of IBRV at both permissive (about 34.5° C.) and nonpermissive (about 39.1° C.) temperatures. It is important that the $tk^-$ IBRV host cells do not detectably revert to $tk^+$ in growth media supplemented with $10^{-4}$M hypoxanthine, $10^{-6}$M aminopterin, $4\times10^{-5}$M thymidine and $10^{-5}$M glycine (hereinafter "HATG") (Dubbs, D. R. et al, *Virol.*, 126:408–411 (1983)), because reversion to $tk^+$ would interfere with autoradiographic and thymidine plaque autoradiographic assays employed to distinguish the phenotypes of $tk^+$ and $tk^-$ IBRVs and mixtures thereof.

As used herein, "selection means" refers to the enrichment of the fraction of a desired recombinant virus in the total virus population. Further, as used herein, "screening means" refers to the identification of the desired recombinant within the total virus population.

Selection means are preferred when used alone, or prior to screening means, when used in combination therewith. This is because the resulting enrichment for the desired recombination viruses due to the use of selection means reduces the amount of screening required to obtain the recombinant viruses.

In addition, whether "selection means" or "screening means" is employed will depend upon the foreign gene used as the insertion. For example, if the foreign gene to be inserted is, e.g., the *E. coli* lacZ gene or an antigen gene, such as the PRV g92 gene, "screening means" will be employed. On the other hand, if the foreign gene is a dominant marker, for example, a tk gene (e.g., a PRV tk gene or other viral, eucaryotic or procaryotic tk gene) or the ($neo^R$) gene, "selection means" will be employed.

The specific selection means for selecting for the presence or absence of a functional TK, i.e., $tk^+$ or $tk^-$ IBRV, is not critical to the present invention. Examples of the selection means for a $tk^+$ IBRV include: HATG media and growth media supplemented with $6\times10^{-7}$M methotrexate; $1.6\times10^{-5}$M thymidine, $5\times10^{-5}$M adenosine, $5\times10^{-5}$M guanosine and $10^{-4}$M glycine (hereinafter "MTAGG") (Munyon, W. et al, *J. Virol.,* 7:813–820 (1971)). Examples of the selection means for a $tk^-$ IBRV include: growth media containing 25 μg/ml of 5-bromodeoxyuridine (hereinafter "BrdUrd"), growth media containing 100 μg/ml of 5-iododeoxyuridine (hereinafter ("IdUrd"), or growth media containing 100 μg/ml of arabinosylthymine. Many modifications of the nucleoside analog selection techniques for $tk^-$ IBRV can also be used. For example, the IBRV-infected cells can be grown in media with about 2.5 to 25 μg/ml of BrdUrd. Since BrdUrd is incorporated into DNA of $tk^+$ IBRV and BrdUrd-containing DNA is highly photosensitive, the virus harvests can be treated with about 0.5 μM Hoechst 33258 to further photosensitize the DNA. The DNA is then exposed to "cool white" fluorescent light (General Electric, 15 w) for 4 min to deliver about 50 erg/mm$^2$/sec (Hillary, A. M. et al, *Biochem. Genett,* 22:201–213 (1984)). Following this procedure, the infectivity of $tk^+$ IBRV is selectively destroyed, while $tk^-$ IBRV are resistant to this treatment.

As discussed above, the *E. coli* lacZ gene can be used as the foreign DNA sequence and can be fused to an IBRV gene promoter or foreign gene promoter such that the resulting hybrid gene is flanked on both the 5' and 3' sides by, for example, IBRV tk DNA, in $tk^-$ IBRV insertion mutants or to IBRV gIII DNA, in $gIII^-$ insertion mutants. The expression of *E. coli* lacZ in insertion mutants of this type can then be screened for by assaying recombinant IBRV plaques expressing β-galactosidase, which is detected by the blue color produced by action of the enzyme upon X-gal (Boehringer-Mannheim) (Chakarabarti, S. et al, *Mol. Cell. Biol.,* 5:3403–3409 (1985)). Alternatively, if the lacZ gene is not expressed, insertion mutants may be detected by molecular hybridization experiments with *E. coli* lacZ DNA probes as in one embodiment of the present invention.

As discussed above, the transposon Tn5 gene (neo$^R$) can also be used as the foreign DNA sequence. This transposon encodes an aminoglycoside 3'-phosphotransferase and is capable of conferring resistance to neomycin and to the drug, G418 (pNeo; Pharmacia P-L Biochemicals). To obtain expression of the transposon Tn5 gene, it is necessary that an IBRV gene promoter or foreign gene promoter be positioned 5' to the coding region of the transposon Tn5 gene (Franke, C. A. et al, *Mol. Cell. Biol.,* 5:1918–1924 (1985)).

The IBRV-based viral vectors of the present invention which express complete or partial genes for antigens or antigenic portions thereof as foreign genes can be screened for by standard immunological procedures. A convenient and rapid procedure for screening plaques formed by viruses expressing such foreign genes are well known (Holland, T. C. et al, *J. Virol.,* 46:649–652 (1983)). In addition, the IBRV-based viral vectors of the present invention which express foreign antigens can be screened for by co-expression of a marker gene, such as the *E. coli* lacZ gene (Chakarabarti, S. et al, *Mol. Cell. Biol.,* 5:3403–3409 (1985)).

In the process for producing an IBRV-based viral vector, wherein a foreign gene, such as PRV g92, is inserted into the IBRV tk gene to produce a $tk^-$ IBRV insertion mutant, "selection means" with drugs such as BrdUrd identify $tk^-$ IBRV insertion mutants. On the other hand, if a non-essential IBRV gene which encodes an antigen is the site of the foreign gene insertion, such as the IBRV gIII gene, "screening means" are employed using immunological techniques to identify $gIII^-$ IBRV insertion mutants. The method for screening for IBRV $gIII^-$ insertion mutants is not critical to the present invention. Screening can be performed, for example, by dot blot-molecular hybridization techniques utilizing radioactive single-stranded DNA probes. These probes comprise, for example, IBRV gIII gene sequences which would be predicted to be absent from the IBRV $gIII^-$ deletion mutants, IBRV gene sequences which would be predicted to be present in the IBRV $gIII^-$ deletion mutants, and foreign DNA sequences which would be predicted to be present in the IBRV $gIII^-$ insertion and deletion/insertion mutants. However, those skilled in the art would recognize that molecular hybridization screening can be performed with radioactive double-stranded DNA probes, or with labeled RNA probes, such as those obtained through the use of phage T7 RNA polymerase or SP6 polymerase (Bethesda Research Laboratories and Promega Biotec), or even with nonradioactive probes, such as biotinylated nucleotide probe systems (Enzo Biochem, Inc.).

Furthermore, screening for IBRV $gIII^-$ mutants can be performed by methods other than those requiring the use of DNA or RNA probes. For example, by using monoclonal antibodies specific for the IBRV gIII glycoprotein, plaques can be screened for viruses failing to express IBRV gIII by plaque immunological procedures. In addition, by the use of anti-IBRV polyclonal sera or monoclonal antibodies specific for another IBRV glycoprotein, e.g., gI, and/or anti-foreign antigen polyclonal sera or monoclonal antibodies specific for the foreign antigen, plaques can be screened for viruses expressing the other IBRV proteins or foreign antigens. In this manner, e.g., IBRV $gIII^-$ deletion and/or insertion mutants can be identified and isolated.

In the context of this invention, a temperature-resistant virus is virus which is nontemperature-sensitive. Thus, a temperature-resistant virus is capable of replicating, at a nonpermissive temperature, i.e., about 38.5° C. to 40° C., preferably 39.1° C., about as well as the parental virus or field isolates of IBRV replicate at a permissive temperature. By contrast, temperature-sensitive IBRV strains contain mutations in viral genes essential for replication, whereby functional gene products are produced at permissive temperatures, i.e., about 32° C. to 37.5° C., preferably 34.5° C., but not at nonpermissive temperatures. Therefore, in temperature-sensitive viruses, production of infectious virus particles is 4 to 7 logs lower at the nonpermissive temperatures compared to production at permissive temperatures. With temperature-resistant virus strains, production of infectious virus particles is about the same at nonpermissive temperatures as at permissive temperatures.

Temperature-resistant viruses are superior to temperature-sensitive viruses as modified live virus vaccines because (1) attenuation results from alterations in pathogenic viral genes rather than from crippling viral genes required for replication; and (2) temperature-resistant viruses can be safely administered intramuscularly, intranasally or intravenously and can replicate in the deep tissues of the body so as to elicit a more complete and prolonged immunological response. In contrast, temperature-sensitive viruses only replicate at low temperature sites, such as the upper respiratory tract and, thus, can only be administered intranasally.

The $tk^-$ IBRV mutants of the present invention can be employed as modified live virus vaccines against IBR disease when containing additional mutations which serve as virus markers or attenuate IBRV. Such additional mutations include IBRV gIII mutations and mutations in non-essential glycoprotein genes other than gIII. For example, an IBRV gene which is located in the $U_S$ region of the IBRV genome and which is homologous to the PRV gI gene and the HSV gE gene may be non-essential for virus replication and may be mutated without impairing the protective properties of the vaccine (Longnecker, R. et al, *Science,* 236:573–576 (1987); Petrovskis, E. A. et al, *Virol.,* 159:193–195 (1987)).

Alternatively, the $tk^-$ IBRV mutants of the present invention can be employed as killed virus vaccines against IBR disease. That is, inactivation of infectivity by ultraviolet light or formaldehyde treatment of the $tk^-$ IBRV mutants yields a vaccine capable, after intraperitoneal administration, of eliciting cytotoxic T cells and protective antibodies against virion proteins. Animals immunized with this vaccine would thus be protected against virulent virus infections.

Furthermore, nonionic detergent extracts (Nonidet P40 or Triton X-100) can be made from $tk^-$ IBRV-infected bovine cells to produce subunit IBRV vaccines. After purification of the glycoproteins, they can be employed as subunit vaccines. Similarly, nonionic detergent extracts can be made from the IBRV-based viral vector-infected bovine cells to produce so-called genetically pure foreign antigens, i.e., antigens which are free from other antigens of the pathogen from which the foreign antigen is derived. After purification of the foreign antigens, they can be employed as subunit vaccines or for preparing polyclonal or monoclonal antibodies useful in diagnostic assays (Hilleman, M. R. et al, In: *The Human Herpesvirus: An Interdisciplinary Perspective*, Eds. Nahmias, A. J. et al (Elsevier, New York), page 503 (1981); Eisenberg, R. J. et al, *J. Virol.,* 41:1099–1104 (1982); Long, D. et al, *Inf. Immun.,* 37:761–764 (1984); Dix, R. D. et al, *J. Med. Virol.,* 17:9–18 (1985)).

As another alternative, the $tk^-$ IBRV mutants of the present invention can be employed as a starting material to obtain the $gIII^-$ IBRV mutants described in U.S. patent application Ser. No. 116,197, filed Nov. 3, 1987 now U.S. Pat. No. 4,992,051.

A pharmaceutically effective amount of the above-described viruses of the present invention can be employed along with a pharmaceutically acceptable carrier or diluent as a vaccine against IBR disease in animals such as bovine, sheep, goats and swine.

Examples of pharmaceutically acceptable carriers or diluents useful in the present invention include any physiological buffered media, i.e., about pH 7.0 to 7.4, containing from about 2.5 to 15% (v/v) serum which does not contain antibodies to IBRV, i.e., is seronegative for IBRV. Agammaglobulin serum is preferred to serum which contains gammaglobulin. Examples of serum to be employed in the present invention include swine serum, calf serum, fetal calf serum, horse serum and lamb serum. Agammaglobulin swine serum from pigs seronegative for IBRV is preferred for vaccination of swine. Agammaglobulin fetal calf serum or agammaglobulin calf serum from calves seronegative for IBRV is preferred for vaccination of calves. Serum protein such as porcine albumin or bovine serum albumin in an amount of from about 0.5 to 3.0% (w/v) can be employed as a substitute for serum. However, it is desirable to avoid the use of foreign proteins in the carrier or diluent which will induce allergic responses in the animal being vaccinated.

The virus may be diluted in any of the conventional stabilizing solutions containing phosphate buffer, glutamate, casitone, and sucrose or sorbose, or containing phosphate buffer, lactose, dextran and glutamate.

It is preferred that the viruses of the present invention be stored at a titer of at least $10^5$ to $10^6$ p.f.u./ml at −70° C. to −90° C. or in a lyophilized state at 4° C. to −20° C. The lyophilized virus may be reconstituted for use with sterile distilled water or using an aqueous diluent containing preservatives such as gentamycin and amphotericin B or penicillin and streptomycin.

The useful dosage to be administered will vary depending upon the age, weight and species of the animal vaccinated and the mode of administration. As a modified-live virus vaccine, a suitable dosage can be, for example, about $10^{4.5}$ to $10^7$ p.f.u./animal, preferably about $10^{4.5}$ to $10^{5.5}$ p.f.u./animal. As a killed vaccine, a suitable dosage can be, for example, about $10^7$ p.f.u./animal or greater.

The vaccines of the present invention can be administered intramuscularly and subcutaneously. Intramuscularly is the preferred mode of administration. The vaccines of the present invention can also be administered intranasally.

The following examples are provided for illustrative purposes only and are in no way intended to limit the scope of the present invention.

In the following examples, all media and buffer solutions were made up in glass distilled water unless otherwise indicated.

EXAMPLE 1

Construction of a $tk^-$ IBRV Insertion Mutant

This example describes a method for the production of an IBRV insertion mutant in the IBRV tk gene such that the resulting IBRV mutant fails to produce any functional TK. In this example, the foreign DNA used for insertion was the lacZ gene of *E. coli* and this gene was inserted in an inverse orientation from the promoter sequence of the IBRV tk gene, so that the *E. coli* lacZ gene was not expressed. However, other foreign genes and/or noncoding DNA sequences could be employed herein to produce insertions either in the correct or the inverse orientations so that the foreign DNA is not expressed. In this example, the *E. coli* lacZ gene was inserted at the BglII restriction endonuclease cleavage site of the IBRV tk gene, that is, about 467 nucleotides downstream from the translational start signal of the IBRV tk gene. However, the insertion of the foreign DNA could be made at other locations in the coding region or the promoter region of the IBRV tk gene and if desired IBRV tk gene sequences could also have been deleted, so as to produce a mutant which fails to produce any functional TK without departing from the spirit and scope of this invention.

A. Construction of pLATKdlNdeI/βGalINV pLATKdlNdeI/βGalINV was obtained by inserting a 3.0 kb BamHI fragment derived from pMC1871 containing the *E. coli* lacZ (βGal) gene into the BglII site of pLATKdlNdeI. The insert was placed in an inverse position relative to the IBRV tk gene promoter to avoid incidental expression of the *E. coli* lacZ (βGal) gene (see FIG. 1).

More specifically, 1.0 μg of pLATKdlNdeI, obtained as described in U.S. Pat. No. 4,703,011, was digested with 5 units of BglII (New England Biolabs, Inc.) at 37° C. for 90 min in 50 μl of buffer comprising 100 mM NaCl, 10 mM Tris-HCl (pH 7.4), 10 mM $MgCl_2$, 10 mM 2-mercaptoethanol and 100 μg/ml of bovine serum albumin (hereinafter "BSA"). The reaction was stopped by adding CDTA to a final concentration of 20 mM and heating the mixture at 65° C. for 30 min. Sodium acetate was added to 0.15M and the DNA was precipitated with 2 volumes of ethanol. The DNA precipitate was collected by centrifugation, then redissolved in 45 μl of buffer comprising 50 mM Tris-HCl (pH 8.0) and 50 mM NaCl. The terminal ends of the BglII-cleaved pLATKdlNdeI were dephosphorylated by adding 5.0 μl (0.12 units) of bacterial alkaline phosphatase (International Biotechnologies, Inc.) and incubating at 65° C. for 1 hr. The enzyme was inactivated by adding Proteinase K at a concentration of 100 μg/ml and incubating at 37° C. for 1 hr followed by phenol extraction. Then, sodium acetate was added to 0.3M and the DNA precipitated by the addition of 2 volumes of ethanol. The DNA precipitate was collected by centrifugation and air dried.

The *E. coli* lacZ gene was obtained as a gift from Malcolm J. Casadaban as a 3.0 kb PstI fragment inserted into the PstI site of pBR322, which has been designated pMC1871 (Casadaban, M. J. et al, *Methods in Enzymology*, 100:293 (1983)). 1.0 μg of pMC1871 was digested with 5 units of BamHI (New England Biolabs, Inc.) at 37° C. for 90 min in 50 μl of buffer comprising 150 mM NaCl, 6.0 mM Tris-HCl (pH 7.9), 6.0 mM $MgCl_2$ and 100 μg/ml of BSA. The reaction was stopped by adding CDTA to a final concentration of 20 mM and heating the mixture at 65° C. for 30 min. The DNA was ethanol precipitated as described above, collected by centrifugation and air dried.

The BamHI-cleaved pMC1871 and the BglII-cleaved and dephosphorylated pLATKdlNdeI were redissolved and combined in 50 μl of buffer comprising 50 mM Tris-HCl (pH 7.8), 10 mM $MgCl_2$, 20 mM dithiothreitol, 1.0 mM ATP and 50 μg/ml of BSA. The DNA fragments were ligated together by adding 1000 units of T4 DNA ligase (New England Biolabs, Inc.) and incubating at 4° C. overnight. The reaction was stopped by adding EDTA to a final concentration of 20 mM and heating at 65° C. for 10 min.

*E. coli* K12 strain RR1 was transformed with the resulting hybrid plasmids and the hybrid plasmid DNA of recombinant clones was isolated by the rapid screening procedure described in U.S. Pat. No. 4,514,497. Restriction endonuclease mapping identified the desired 9.2 kb plasmid, designated pLATKdlNdeI/βGalINV (see FIG. 1).

B. Construction of $tk^-$ IBRV(βGalINV)

In order to obtain, by homologous recombination, a $tk^-$ IBRV insertion mutant, it was necessary to start with the intact DNA of a $tk^+$ IBRV and a hybrid plasmid containing an insertion in the coding or promoter region of the IBRV tk gene. The progeny virus obtained following this type of cross mainly comprise parental $tk^+$ IBRV. Thus, in order to enrich for the $tk^-$ IBRV recombinants in the harvests, selective media containing 5-iododeoxyuridine (hereinafter "IUdR") was employed, since IUdR inhibits $tk^+$ IBRV replication and favors the outgrowth of $tk^-$ IBRV. However, other analogs of thymidine, such as BrdUrd, bromovinyldeoxyuridine or arabinosylthymine could also have been used as selective drugs without departing from the spirit and scope of the present invention.

The hybrid plasmid chosen for the construction of the $tk^-$ IBRV insertion mutant was pLATKdlNdeI/βGalINV (see FIG. 1). However, other hybrid plasmids containing larger or smaller insertions of foreign DNA into the same or other regions of the IBRV tk gene could be employed to create "insertion" mutants, without departing from the spirit and scope of this invention (see FIG. 2).

More specifically, 10 μg of pLATKdlNdeI/βGalINV (see FIG. 1) was digested with 50 units of PstI (New England Biolabs, Inc.) in buffer comprising 100 mM NaCl, 10 mM Tris-HCl (pH 7.5), 10 mM $MgCl_2$ and 100 μg/ml of BSA at 37° C. for 1 hr. The enzyme was inactivated by adding Proteinase K to a final concentration of 100 μg/ml and incubating at 37° C. for 1 hr, followed by phenol extraction. The PstI-cleaved plasmid was dialyzed against 0.1×TE buffer. TE buffer comprises 10 mM Tris-HCl (pH 7.5), 1.0 mM EDTA. Then, the PstI-cleaved plasmid was adjusted to 10 μg/ml, and filter sterilized.

The $tk^+$ IBRV DNA chosen for the recombination step was IBRV(RTK-1B) (U.S. Pat. No. 4,703,011). Since IBRV(RTK-1B) was derived from IBRV(B8-D53), a vaccine strain attenuated through multiple mutations induced by mutagens, IBRV(RTK-1B) was the preferred virus to other $tk^+$IBRV field strains for the construction of the $tk^-$ IBRV insertion mutant. However, as described above, other $tk^+$ IBRV strains would be suitable without departing from the spirit and scope of this invention.

The construction of the recombinant $tk^-$ insertion mutant of IBRV(RTK-1B) was carried out as follows (see FIG. 2):

Rab-9 cells were seeded in 60 mm Petri dishes ($0.2\times10^6$ cells per dish) and incubated at 37° C. for 48 hr. Then, the following sterile solutions were added to a test tube in sequential order:

(1) 0.02 ml of a 50 μg/ml solution of IBRV(RTK-1B) DNA in TE buffer;

(2) 0.2 ml of a 10 μg/ml solution of PstI-cleaved pLATKdlNdeI/βGalINV in 0.1×TE buffer;

(3) 0.65 ml of water;

(4) 1.0 ml of a 20 μg/ml solution of salmon sperm DNA in 2×Hepes buffer solution comprising 16 g/l NaCl, 0.74 g/l KCl 0.25 g/l $Na_2HPO_4.2H_2O$, 2.0 g/l glucose, 10 g/l Hepes (pH 7.05) (hereinafter "2×Hepes buffer solution");

(5) 0.13 ml of 2.0M $CaCl_2$.

The resulting solution was mixed by inversion and kept at room temperature for 30 min while a DNA-calcium phosphate precipitate formed. Then, 0.5 ml of the suspension containing a calcium phosphate precipitate of DNA was added directly to 5.0 ml of growth media and plated on the Rab-9 cells in Petri dishes which had been seeded 48 hr earlier. The cells were incubated at 37° C. for 5 hr. Then the growth media was aspirated, and the monolayer rinsed with 5.0 ml of fresh growth media, followed by the addition of 1.0 ml of a solution of 1×Hepes buffer solution plus 15% (v/v) glycerol. After a 3-min incubation at room temperature, the solution was aspirated, the monolayer rinsed with growth media again, and fresh growth media was added. The culture was incubated at 34.5° C. for 3 days until extensive cytopathic effects occurred. Virus harvests were made as described in U.S. Pat. No. 4,703,011 and stored at −80° C. The virus harvests were then titrated in Rab-9 cells under a 0.5% (w/v) agarose overlay.

The virus harvests from the co-transfection were thawed, sonicated and diluted in growth media supplemented with 100 μg/ml of IUdR. In order to enrich for $tk^-$ IBRV insertion mutants, the virus harvests were diluted to give an input multiplicity of 0.1 p.f.u./cell and passaged in confluent monolayer cultures of $tk^-$ Rab(BU) cells in eight-ounce prescription bottles in growth media supplemented with 100 μg/ml of IUdR. After a 1 hr absorbtion at 37° C., the infected monolayer cultures were washed 3 times with a solution comprising 8.0 g NaCl, 0.4 g KCl, 0.1 g glucose and 0.02 g phenol red per liter of water (hereinafter "GKN"). Then, growth media containing 100 μg/ml of IUdR was added, incubation was continued at 34.5° C. for 48 hr, and virus harvests were made.

The harvest of the first selection step was titrated, and a second selection step was carried out as described above. The harvest of the second selection step was titrated in Rab-9 cells, candidate $tk^-$ IBRV insertion mutants were picked at random from plaques, and virus pools were prepared. In this manner, 96 $tk^-$ IBRV insertion mutant candidates were obtained.

C. Preparation of $^{32}$P-Labeled *E. coli* lacZ Gene Probe

To identify recombinant virus among the candidate clones, and to verify that insertions of foreign DNA existed in the IBRV tk gene, molecular hybridization experiments were carried out with a $^{32}$P-labeled probe derived from the foreign DNA, i.e., the *E. coli* lacZ gene in pMC1871.

More specifically, about 1.0 μg pMC1871DNA was added to 25 μl of buffer comprising 6.0 μmol PBS (pH 7.4), 1.8 nmol dATP, 1.8 nmol dGTP, 0.1 mCi (α-$^{32}$P)dTTP (400 Ci/mmole), and 0.1 mCi (α-$^{32}$P )dCTP (400 Ci/mmole) (Amersham Corporation). Then, 1.33 ng in 1.0 μl of DNase I (Worthington Biochemical Corporation) was added and the reaction mixture was allowed to stand at room temperature for 1 min. Next, the reaction mixture was incubated at 14° C. with 5.0 units in 1.0 μl of *E. coli* DNA polymerase I (Boehringer-Mannheim Biochemicals). When the specific activity became higher than $2\times10^8$ cpm/μg of DNA, i.e., about 3 hr, the reaction was terminated by adding 10 μl of 0.25M EDTA (pH 7.4) and heating at 68° C. for 10 min. Then, as carrier, 50 μl of a solution comprising 5.0 mg/ml sonicated salmon sperm DNA in TE buffer was added to the mixture and the nick-translated DNA was purified by Sephadex G50 (fine) column chromatography using 10 mM NaCl, 10 mM Tris-HCl (pH 7.5), 2.0 mM EDTA as the elution buffer.

The resulting $^{32}$P-labeled DNA was used as a probe in DNA-DNA hybridization experiments after boiling in a water bath for 20 min, and quickly cooling on ice to form single-stranded DNA (Rigby, P. W. J. et al, *J. Mol. Biol.*, 113:237–251 (1977)).

D. Identification of Recombinant $tk^-$ IBRV Insertion Mutants of IBRV(RTK-1B) by Molecular Hybridization Viral DNAs prepared from each of the 96 candidate IBRV recombinants described above were analyzed by the dot blot method (Brandsma, J. et al, *Proc. Natl. Acad. Sci. USA*, 77:6851–6855 (1980)) using the $^{32}$P-labeled pMC1871 probe so as to identify viruses that had an insertion of βGal nucleotide sequences from pMC1871 in the IBRV tk gene.

More specifically, 24-well multiwell tissue culture trays containing confluent monolayers of Rab-9 cells were infected with 0.05 ml of undiluted candidate virus and incubated at 34.5° C. for 8 hr. The virus inoculum was aspirated, the wells rinsed with 1.0 ml of GKN, and 0.2 ml of 0.5 N NaOH was added to each well to lyse the cells and release the DNA. After storage at room temperature overnight, 0.3 ml of 1.0 M Tris-HCl (pH 7.5) and 0.5 ml of buffer comprising 3.0 M NaCl and 0.3M sodium citrate (pH 7.0) (hereinafter "20×SSC") were added per well. For dot blot analysis, a nitrocellulose filter in a 96-well Schleicher and Schuell filtration apparatus was used. The filter was washed with water and with 1× SSC prior to the addition of the DNA samples. To bake the DNA samples to the filter, the nitrocellulose filter was dried, heated at 60° C. overnight in a vacuum desicattor, and then heated at 80° C. for 2 hr. The filter was placed in a plastic sealable pouch containing 50 ml of 3×SSC, 0.02% (w/v) Ficoll, 0.02% (w/v) BSA, 0.02% (w/v) polyvinylpyrrollidone, and 50 μg/ml of boiled and alkali-denatured salmon sperm DNA (hereinafter "modified Denhardt's solution"), and 10 μg/ml of poly(A) and incubated at 60° C. overnight with shaking. Alkaline salmon sperm DNA was added from a stock solution of about 5.0 mg/ml prepared by dissolving 50 mg of salmon sperm DNA in 10 ml of 0.2N NaOH, heating at 100° C. for 20 min to denature and shearing the DNA to about 0.4 kb segments, and then neutralizing with 0.2 ml of 10N HCl.

The modified Denhardt's solution was then replaced with 50 ml of hybridization buffer comprising 50% (v/v) formamide, 0.6M NaCl, 0.02M Tris-HCl (pH 8.0), 0.02M EDTA, 0.1% (w/v) sodium dodecylsulfate (hereinafter "SDS"), 50 μg/ml of alkali-denatured salmon sperm DNA, and 10 μg/ml of poly(A) (hereinafter "hybridization buffer"). Next, air bubbles were squeezed out of the bag which was then sealed using an Oster Touch-a-Matic Bag Sealer and incubated at 37° C. for 1 hr on a shaker.

Thereafter, about 1.0 ml, containing $10^7$ cpm and 50 ng, of single-stranded $^{32}$P-labeled pMC1871, obtained as described above, was added to the bag with a 3.0 ml syringe by piercing the side of the bag at a corner. Next, the bag was resealed and incubated at 37° C. for up to 48 hr on a shaker to allow for hybridization.

After hybridization had been accomplished, the bag was cut and the solution was decanted. The filter was then carefully removed and placed into a tray containing about 100 ml of hybridization buffer containing 50 μg/ml of denatured salmon sperm DNA for the first wash only, but no poly(A) in any wash. The filter was washed at 37° C. for 30 min five times with gentle shaking. Next, the filter was washed at 37° C. for 30 min with 0.3×SSC and then placed on filter paper to dry overnight at room temperature.

For autoradiography, the filter was replaced on a thin piece of cardboard covered with Saran-Wrap, and exposed to Fuji X-ray film with an intensifying screen at −70° C. for periods of 5 hr to 2 days.

Three out of the 96 candidate IBRV recombinants were found to hybridize to the pMC1871 probe, indicating that these clones had an insertion of the βGal sequence into the IBRV tk gene. Two clones were designated IBRV(βGalINV) clone 1 and clone 13 and saved for further analysis. IBRV(βGalINV) clone 1 has been deposited on Jan. 7, 1987 with the American Type Culture Collection at 12301 Parklawn Drive, Rockville, Md. 20852 under ATCC No. VR 2160.

E. Analyses of the Viral DNA

Viral DNA of high purity was prepared from IBRV(βGalINV) clone 1 and clone 13 as described in U.S. Pat. No. 4,703,011. Then, 0.5 μg of viral DNA from each of the candidate insertion mutants was cleaved with KpnI under conditions specified by New England Biolabs, and the fragments were separated by electrophoresis on 0.6% (w/v) agarose at 35 volts (constant voltage) at 4° C. for 16 hr. The electrophoresis buffer was 0.04M Trizma base (pH 8.1), 0.03M $NaH_2PO_4$, and 0.001M EDTA. DNAs from the parental $tk^+$ IBRV(RTK-1B), $tk^+$ IBRV(Los Angeles), $tk^-$ IBRV(B8-D53), $tk^-$ IBRV(NG)dltk, were also cleaved with KpnI and separated by electrophoresis. Marker fragments were obtained by HindIII digestion of phage lambda DNA and HaeIII digestion of phage ΦX174 RF DNA. The gels were stained with 0.5 μg/ml of ethidium bromide and photographed to reveal the DNA fragments.

Figure 2:
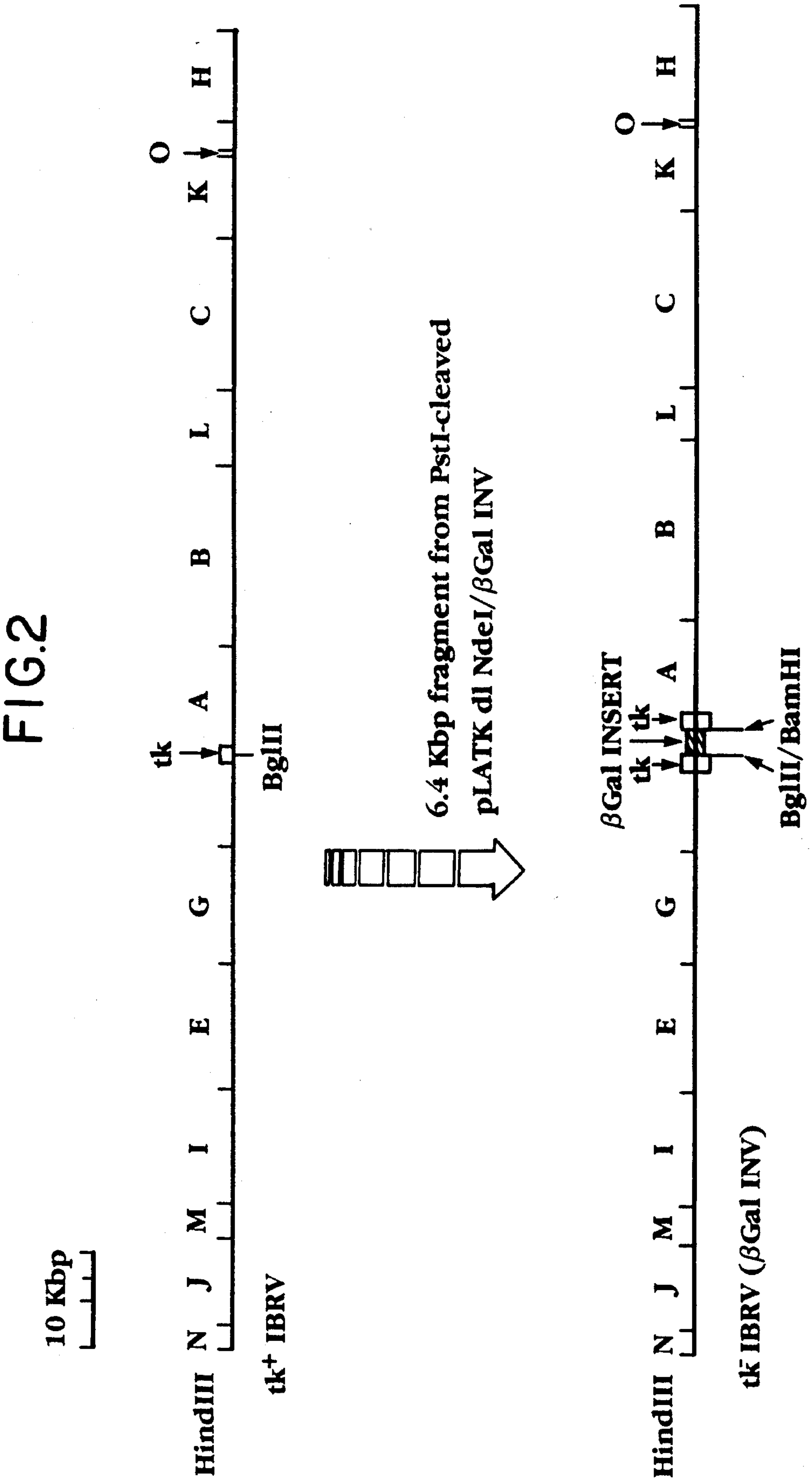
FIG. 2 schematically illustrates, by example, the HindIII restriction endonuclease map of the parental $tk^+$ IBRV strain, IBRV(RTK-1B) (U.S. Pat. No. 4,703,011), which was co-infected with the 6.4 kb PstI fragment from pLATKdlNdeI/βGalINV to give rise to the $tk^-$ IBRV insertion mutant, IBRV(βGalINV), by homologous recombination. The orientation of the *E. coli* lacZ gene in IBRV(βGalINV) is in the opposite direction from that of the promoter sequence of the IBRV tk gene. As a result, the *E. coli* lacZ gene is not expressed by IBRV(βGalINV).

The results demonstrated that the 6.7 kb KpnI fragment of IBRV(RTK-1B) (U.S. Pat. No. 4,703,011; FIG. 2, plasmid pLAK map units 1.6 to 8.3) which contains the IBRV tk gene, was absent from IBRV(βGalINV) and a new fragment of 9.7 kb appeared among the restriction fragments of IBRV(βGalINV). This is consistent with the insertion of 3.0 kb of the *E. coli* lacZ gene into the IBRV tk gene.

After the gel was stained with ethidium bromide and photographed, the separated DNA restriction fragments in the agarose gel were transferred to nitrocellulose filters (Schleicher and Schuell) for Southern blot molecular hybridization analyses in the following manner. The agarose gel was placed in a glass baking tray containing 1.0M KOH for 30 min at room temperature and, then, in a glass baking tray containing 1.0M Tris-HCl (pH 7.0) and 0.6M NaCl at room temperature for 60 min. The treated gel was then transferred to a blot apparatus (Bethesda Research Laboratories).

A nitrocellulose filter was prewetted in water for 10 min and then in 20×SSC for 5 min. Next, the filter was placed on the gel. Using 20× SSC as the transfer fluid, blotting was allowed to proceed for about 24 hr. The adherent gel was removed from the nitrocellulose filter, and the filter was rinsed with 6×SSC, dried at room temperature for several hours, and then in a vacuum desiccator at 60° C. overnight. This was followed by baking at 80° C. for 2 hr. The nitrocellulose filters were removed from the desiccator and placed in Dazey Seal-a-Meal cooking bags (Southern, E. J., *J. Mol. Biol.*, 98:503–513 (1975)).

The filter was first pretreated at 60° C. overnight with 50 ml of modified Denhardt's solution and 50 ml of hybridization buffer at 37° C. as described above.

The nitrocellulose filter was next hybridized to a $^{32}$P-labeled pMC1871 probe. The procedures for molecular hybridization of the probe to the nitrocellulose filters and the washing step were the same as described above and in U.S. Pat. No. 4,703,011.

The results demonstrated that the pMC1871 probe hybridizes specifically to a 9.7 kb KpnI fragment from IBRV(βGalINV) clone 1 and clone 13 but not to any of the fragments of tk$^+$ IBRV(RTK-1B), tk$^+$ IBRV(Los Angeles), tk$^-$ IBRV(B8-D53), or tk$^-$ IBRV(NG)dltk.

These experiments conclusively demonstrate that IBRV(βGalINV) clone 1 and clone 13 have a 3.0 kb insertion of the *E. coli* lacZ gene into the IBRV tk gene.

EXAMPLE 2

Construction of a tk$^-$ IBRV-Based Viral Vector Expressing the PRV g92 Gene Driven by the PRV g92 pPromoter This example describes a method for the production of an IBRV-based viral vector having a foreign gene inserted in the IBRV tk gene so that the IBRV-based viral vector fails to express any functional TK and in which expression of the foreign gene is driven by the native promoter of the foreign gene. In this example, the foreign DNA inserted into the IBRV tk gene was the PRV g92 gene including its 5' promoter signals and 3' polyadenylation signals. The PRV g92 gene was expressed following infection of susceptible host cells by the recombinant virus. Although not necessary, in this example, the 0.46 kb BglII to MluI nucleotide sequence of the IBRV tk gene was deleted from the IBRV tk gene. That is, the middle third of the coding sequence of the IBRV tk gene was deleted (see FIG. 3). The PRV g92 gene was inserted in place of the deleted IBRV nucleotide sequences. However, the nucleotide sequences could have been deleted from another part of the coding region of the IBRV tk gene and the foreign DNA insertion could have been made at another location in the IBRV tk gene so as to produce an IBRV-based viral vector with a deletion in the IBRV tk gene without departing from the spirit and scope of this invention.

A. Construction of pSP65/IBRVtk/PRVg92 pSP65/IBRVtk/PRVg92 was obtained by inserting a 3.5 kb MluI to NruI fragment derived from pBUK:Stu12/PstI containing the PRV g92 gene into the BglII to MluI site of pSP65(Exo36) (see FIG. 3).

More specifically, 1.0 μg of pBUK:Stu12/PstI, obtained as described in U.S. Pat. No. 4,711,850, was digested with 5 units of NruI (New England Biolabs) in 20 μl of buffer comprising 50 mM KCl, 50 mM NaCl, 50 mM Tris-HCl (pH 8.0), and 10 mM $MgCl_2$ at 37° C. for 90 min. This produced a blunt-ended DNA. The reaction was stopped by adding EDTA to a final concentration of 22 mM and heating the mixture at 65° C. for 10 min. One-tenth volume of 3.0M sodium acetate was added and the DNA was precipitated with 2.2 volumes of ethanol. The DNA precipitate was collected by centrifugation, redissolved in 50 μl of buffer comprising 50 mM NaCl, 10 mM Tris-HCl (pH 7.5), 7.0 mM $MgCl_2$, 6.0 mM 2-mercaptoethanol and 100 μg/ml of BSA and digested with 5 units of MluI (New England Biolabs) at 37° C. for 90 min. The reaction was stopped by adding 5.0 μl of 0.25M EDTA and heating at 65° C. for 10 min.

1.0 μg of pSP65(Exo36), obtained as described in U.S. Pat. No. 4,703,011, was digested with 5 units of BglII (New England Biolabs) in 20 μl of buffer comprising 100 mM NaCl, 10 mM Tris-HCl (pH 7.4), 10 mM $MgCl_2$, 10 mM 2-mercaptoethanol, and 100 μg/ml of BSA at 37° C. for 90 min. The reaction was stopped by adding EDTA to a final concentration of 20 mM and heating the mixture at 65° C. for 10 min. One-tenth volume of 3.0M sodium acetate was added and the DNA precipitated with 2.2 volumes of ethanol. The DNA precipitate was collected by centrifugation. To convert the termini of the fragment to blunt ends, the DNA precipitate was then treated with 10 units of Mung bean nuclease (International Biotechnologies, Inc.) in 100 μl of buffer comprising 30 mM sodium acetate (pH 5.0), 50 mM NaCl, and 0.1 mM zinc acetate at 37° C. for 10 min. To terminate the reaction, 2.0 μl of 20% (w/v) SDS, 10 μl of 0.5M Tris-HCl (pH 9.5), and 10 μl of 8.0M LiCl were added. The mixture was extracted with an equal volume of phenol:chloroform (1:1) (v/v) and the DNA was precipitated by adding 2 volumes of ethanol. The DNA precipitate was collected by centrifugation and digested with 5 units of MluI in 50 μl of buffer comprising 50 mM NaCl, 10 mM Tris-HCl (pH 7.5), 7.0 mM $MgCl_2$, 6.0M 2-mercaptoethanol, and 100 μg/ml of BSA at 37° C. for 90 min. The reaction was stopped by adding 5.0 μl of 0.25M EDTA and heating at 65° C. for 10 min.

The resulting pBUK:Stu12/PstI, which had been digested first with NruI, thereby producing blunt ends, and then with MluI, and pSP65(Exo36), which had been digested with BglII, blunt-ended and then digested with MluI, were mixed, and extracted once with an equal volume of phenol:chloroform (1:1) (v/v). The DNAs were precipitated from the aqueous phase by adding 0.1 volume of 3.0M sodium acetate and 2.2 volumes of ethanol and ligated with 1,000 units of T4 DNA ligase (New England Biolabs) in 40 μl of buffer comprising 50 mM Tris-HCl (pH 7.8), 10 mM $MgCl_2$, 20 mM dithiothreitol, 1.0 mM ATP, and 50 μg/ml of BSA at 4° C. for 18 hr. The reaction was stopped by adding 0.16 ml of TE buffer.

*E. coli* K12 strain RR1 was transformed with the resulting hybrid plasmids and the hybrid plasmid DNA of recombinant clones was isolated by the rapid screening procedure as described in U.S. Pat. No. 4,514,197. Restriction endonuclease mapping identified the desired 8.0 kb plasmid, designated pSP65/IBRVtk/PRVg92 (see FIG. 3).

B. Construction of tk$^-$ IBRVdltk(PRVg92)

In order to obtain, by homologous recombination, a tk$^-$ deletion/insertion mutant of IBRV which expresses the PRV g92 gene, it was necessary to start with the intact DNA of a tk$^+$ IBRV and a hybrid plasmid containing an insertion of the PRV g92 gene in the coding or promoter region of the IBRV tk gene. The progeny virus obtained following this type of cross mainly comprise parental tk$^+$ IBRV. Thus, in order to enrich for the tk$^-$ IBRV recombinants in the harvests, selective media containing BrdUrd was employed since BrdUrd inhibits $tk^+$ IBRV replication and favors the outgrowth of $tk^-$ IBRV. However, other analogs of thymidine, such as IUdR, bromovinyldeoxyuridine or arabinosylthymine could also have been used as selective drugs without departing from the spirit and scope of the present invention.

Figure 3:
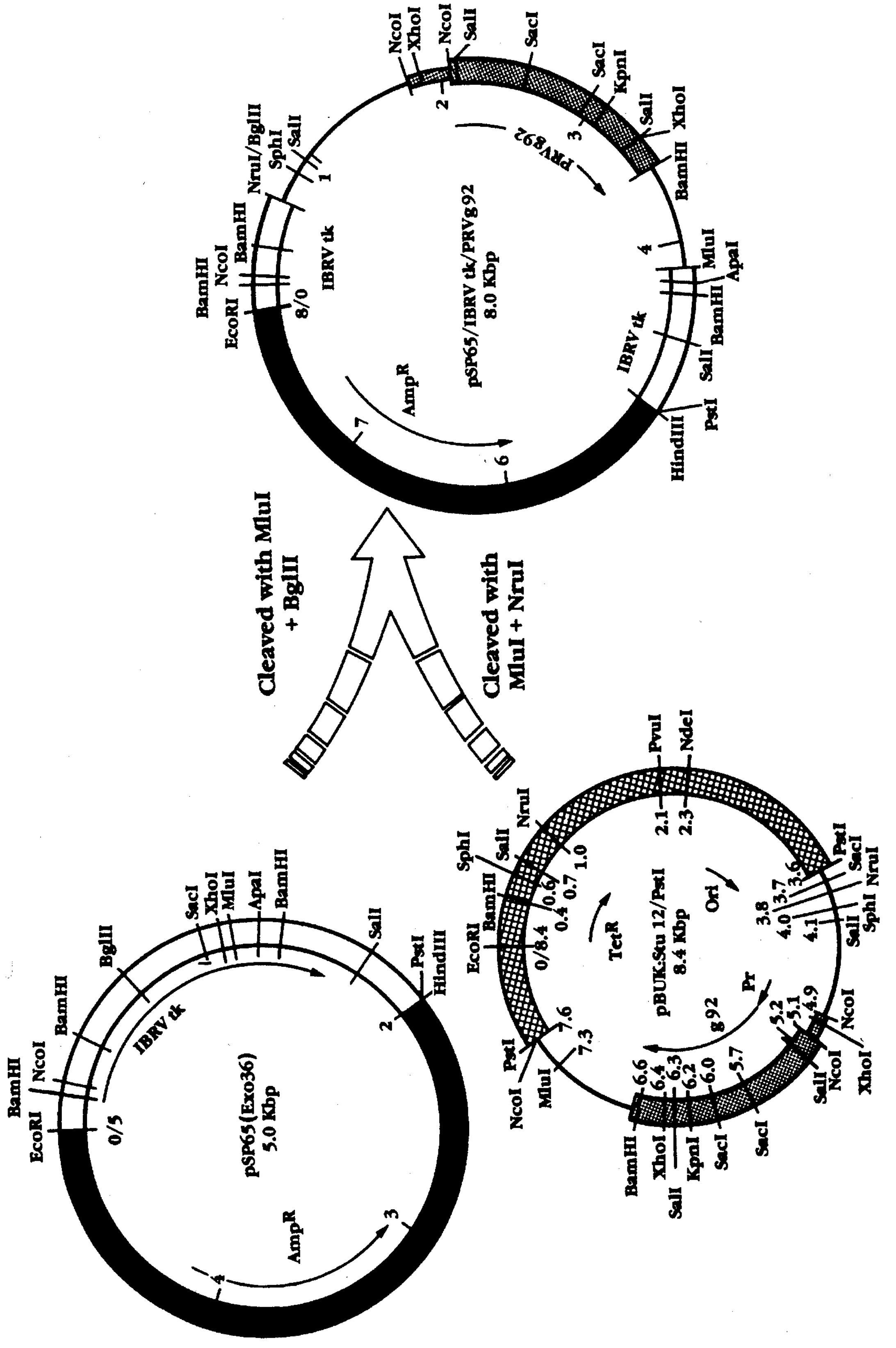
FIG. 3 schematically illustrates, by example, the restriction endonuclease maps of the plasmids used to construct pSP65/IBRVtk/PRVg92, which contains the PRV g92 gene inserted in the IBRV tk gene in place of the BglII to MluI nucleotide sequence of the IBRV tk gene. pSP65(Exo36) was constructed by cloning the IBRV tk gene plus flanking sequences in pSP65 (U.S. Pat. No. 4,703,011). pBUK:Stu12/PstI was constructed by cloning the 4.0 kb PstI fragment of $tk^+$ PRV(BUK-5) DNA, which contains the PRV g92 gene plus its 5' and 3' flanking sequences, at the PstI site of pBR322 (U.S. Pat. No. 4,711,850). pSP65/IBRVtk/PRVg92 was constructed by cleaving pBUK:Stu12/PstI with MluI plus NruI, and cleaving pSP65(Exo36) with MluI plus BglII. The MluI plus BglII-cleaved fragments were treated with Mung bean nuclease to produce blunt ends, and the fragments produced by the two restriction nuclease digestions were then mixed and treated with phage T4 ligase. The black bars represent pSP65 DNA sequences, the white bars represent IBRV DNA sequences, the stippled bars represent the PRV g92 gene with the smaller stippled bars representing the PRV g92 promoter, the hatched bar represents pBR322 DNA sequences and the solid lines represent PRV DNA flanking sequences 5' and 3' to the PRV g92 gene.

The hybrid plasmid chosen for the construction of this $tk^-$ IBRV deletion/insertion mutant was pSP65/IBRVtk/PRVg92 (see FIG. 3). More specifically, 10 μg of pSP65/IBRVtk/PRVg92 was digested with 50 units of EcoRI in 20 μl of buffer comprising 100 mM Tris-HCl (pH 7.5), 50 mM NaCl, 5.0 mM $MgCl_2$, and 100 μg/ml of BSA at 37° C. for 90 min. The DNA was precipitated with 2 volumes of ethanol and digested with 50 units of PstI in 50 μl of buffer comprising 100 mM NaCl, 10 mM Tris-HCl (pH 7.5), 10 mM $MgCl_2$, and 100 μg/ml of BSA at 37° C. for 90 min. The enzyme was inactivated by adding proteinase K to a final concentration of 100 μg/ml and incubating at 37° C. for 1 hr, followed by phenol extraction. The digested plasmid DNA was extensively dialyzed against 0.1×TE, adjusted to 10 μg/ml, and filter sterilized.

The $tk^+$ IBRV DNA chosen for the recombination step was IBRV(Los Angeles) (ATCC No. VR 188). However, as described above, other $tk^+$ IBRV strains would be suitable without departing from the spirit and scope of this invention.

Figure 4:
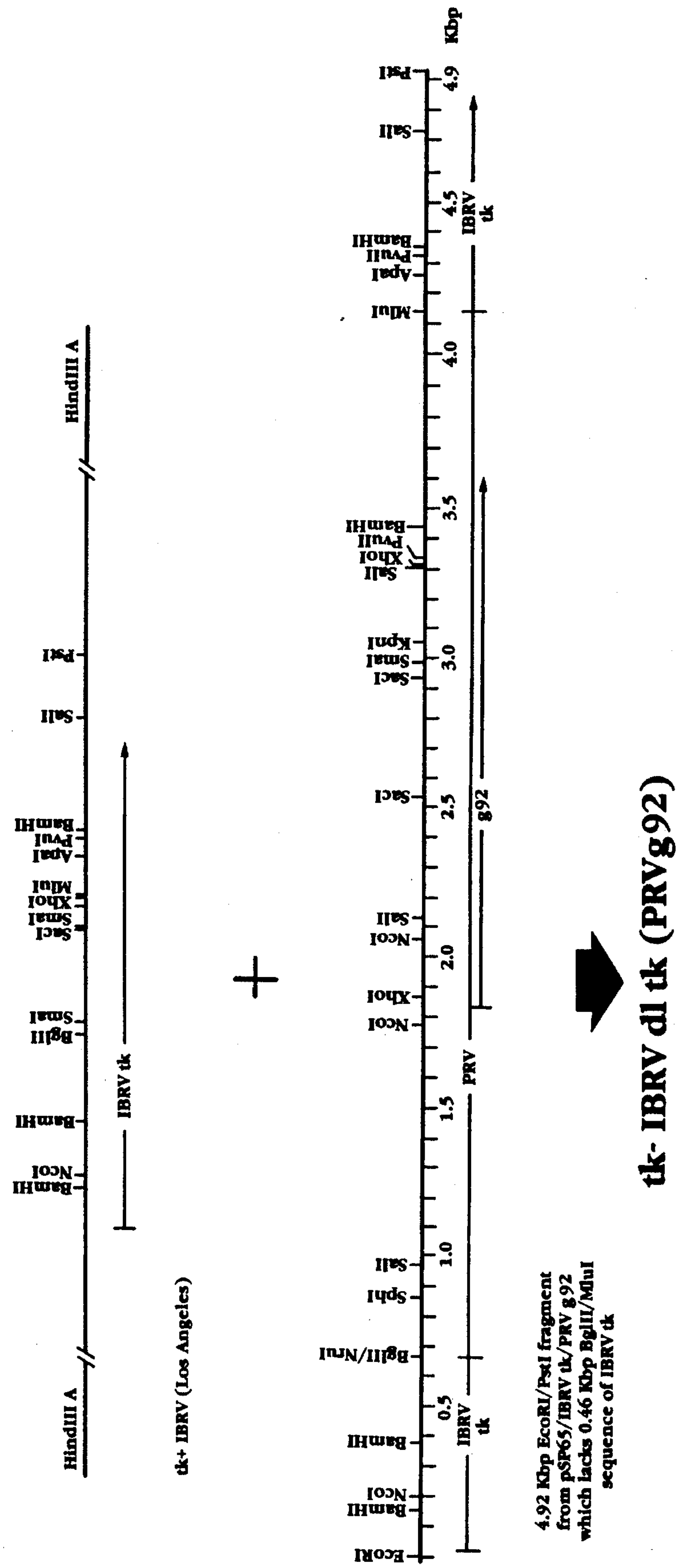
FIG. 4 schematically illustrates, by example, the HindIIIA restriction fragment of the parental $tk^+$ IBRV strain, IBRV-(Los Angeles) (U.S. Pat. No. 4,703,011) which was co-infected with the 4.92 kb EcoRI to PstI fragment from pSP65/IBRVtk/PRVg92, which lack the 0.46 kb BglII to MluI sequence of the coding region of the IBRV tk gene and contains, instead, a PRV DNA insert capable of expressing the PRV g92 gene, to give rise to the $tk^-$ IBRV mutant, IBRVdltk(PRVg92), by homologous recombination. This IBRV mutant expresses the PRV g92 gene from the PRV g92 promoter.

The construction of the recombinant $tk^-$ IBRV mutant of IBRV(Los Angeles) which expresses the PRV g92 gene was carried out in the same manner as described in Example 1 above for the recombinant $tk^-$ insertion mutant of IBRV(RTK-1B) (see FIG. 4).

The virus harvests from the co-transfection were thawed, sonicated and diluted in growth media supplemented with 50 μg/ml of BrdUrd. In order to enrich for $tk^-$ IBRV deletion/insertion mutants, the harvested virus was diluted to give an input multiplicity of 0.1 p.f.u./cell and passaged in confluent monolayer cultures of $tk^-$ Rab(BU) cells in six-ounce prescription bottles in growth media supplemented with 50 μg/ml of BrdUrd. After absorbtion at 37° C. for 1 hr, the infected monolayer cultures were washed 3 times with GKN. Then, growth media containing 50 μg/ml of BrdUrd was added, incubation was continued at 34.5° C. for 48 hr, and virus harvests were made.

The harvest of the first selection step was titrated, and a second selection step was carried out as described above. The harvest of the second selection step was titrated in Rab-9 cells, candidate $tk^-$ IBRV deletion/insertion mutants were picked at random from plaques, and virus pools were prepared. In this manner, 96 $tk^-$ IBRV deletion/insertion mutant candidates were obtained.

C. Preparation of $^{32}P$-labeled pSal Probe

To identify recombinant virus among the candidate clones, and to verify that insertions of foreign DNA existed in the IBRV tk gene, molecular hybridizations were carried with a $^{32}P$-labeled probe derived from the foreign DNA, i.e., the PRV g92 gene in pSal. pSal was obtained from pBUK-:Stu12/PstI by subcloning the 1.1 kb SalI fragment of pBUK:Stu12/PstI into the SalI site of pBR322 as described in U.S. Pat. No. 4,711,850. The $^{32}P$-labeled pSal probe was also prepared as described in U.S. Pat. No. 4,711,850.

D. Identification of Recombinant $tk^-$ IBRV Deletion/Insertion Mutants of IBRV(Los Angeles) by Molecular Hybridization Viral DNAs from each of the 96 candidate IBRV recombinants described above were analyzed by the dot-blot method as described above using the $^{32}P$-labeled pSal probe, which contains coding sequences from the PRV g92 gene, so as to identify viruses that had an insertion of the 3.5 kb NruI to MluI fragment of the PRV g92 gene from pSP65/IBRVtk/PRVg92 in the IBRV tk gene.

Autoradiography was also carried out as described above.

Two out of the 96 candidate IBRV recombinants were found to hybridize to the pSal probe, indicating that these clones had an insertion of the PRV g92 gene into the IBRV tk gene. These two clones were designated IBRVdltk-(PRVg92) clones 6-2 and 7-30, and were saved for further analyses. IBRVdltk(PRVg92) clone 6-2 has been deposited with the American Type Culture Collection Under ATCC No. VR 2182.

E. Analysis of Viral DNA

Viral DNA of high purity was prepared from IBRVdltk-(PRVg92) clone 6-2, as described in U.S. Pat. No. 4,703,011. Then, 0.5 μg of viral DNA was cleaved with PstI, KpnI, HindIII, and BamHI under the conditions specified by New England Biolabs, and the fragments were separated by electrophoresis on a 0.6% (w/v) agarose gel, as discussed above. DNAs from the IBRV(Los Angeles) were also cleaved with PstI, KpnI, HindIII, and BamHI and separated by electrophoresis. Marker fragments were obtained by HindIII digestion of phage lambda DNA and HaeIII digestion of phage ΦX174 RF DNA. The gel was stained with ethidium bromide and photographed as described above to reveal the DNA fragments. The results are shown in FIG. 5A.

Figure 5A:
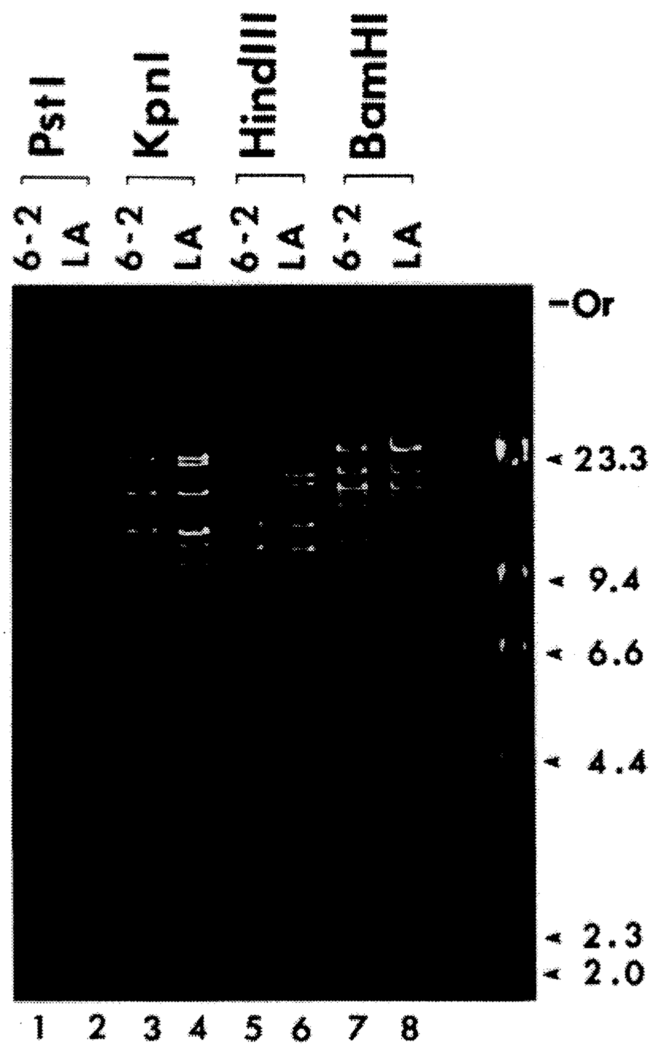
FIG. 5A shows ethidium bromide-stained agarose gel fragments of PstI-, KpnI-, HindIII-, and BamHI-digested DNA from the parental $tk^+$ IBRV(Los Angeles) strain (LA) and from the recombinant IBRVdltk(PRVg92) clone 6-2, which contains the PRV g92 gene inserted in the IBRV tk gene in place of the BglII to MluI sequences of the IBRV tk gene. HindIII-cleaved lambda phage DNA fragments ranging from 2.0 kb to 23.3 kb were utilized as molecular weight markers and are shown at the right of the BamHI fragments.

FIG. 5A demonstrates that the 6.7 kb KpnI fragment of IBRV(Los Angles), which contains the IBRV tk gene, was absent from IBRVdltk(PRVg92) clone 6-2 and that two new fragments of about 5.9 kb and 4.2 kb appeared among the restriction fragments of IBRVdltk(PRVg92) clone 6-2. This was consistent with the insertion of the 3.5 kb NruI to MluI fragment of the PRV g92 gene into the IBRV tk gene at the BglII and MluI sites. FIG. 5A also demonstrates that the HindIII-A fragment of IBRVdltk(PRVg92) clone 6-2 was larger than that of the wild-type IBRV(Los Angeles) strain, as predicted.

After the gel was stained with ethidium bromide and photographed, the separated DNA restriction fragments in the agarose gel were transferred to nitrocellulose filters (Schleicher and Schuell) for Southern blot molecular hybridization analyses as described above using the $^{32}P$-labeled pSal probe. The results are shown in FIG. 5B.

Figure 5B:
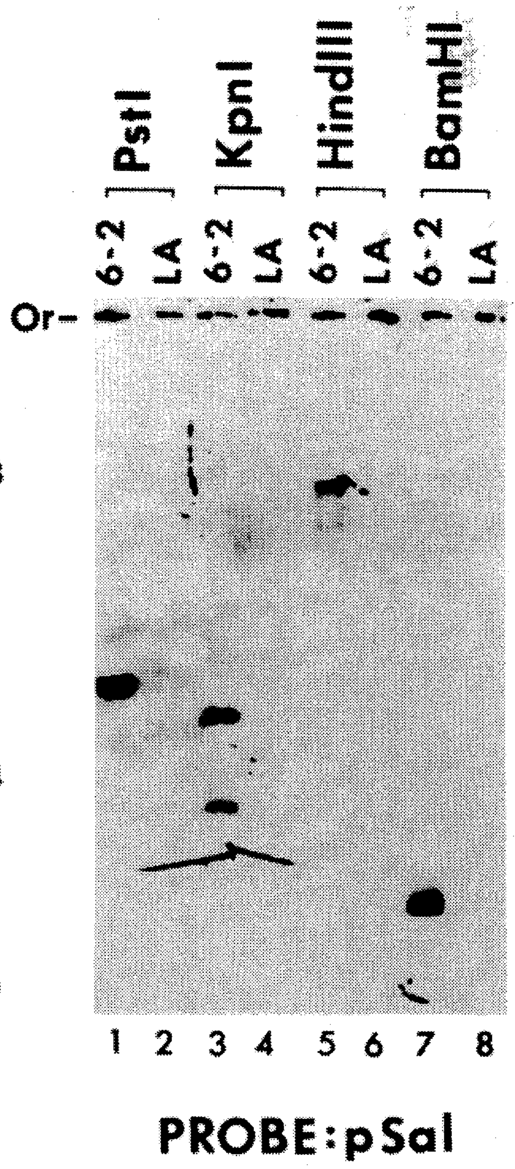
FIG. 5B shows autoradiographs demonstrating molecular hybridization of the 32P-labeled pSal probe to the DNA fragments of IBRVdltk(PRVg92) clone 6-2, but not to DNA fragments of the parental IBRV(Los Angeles) strain. The pSal probe was derived by cloning a 1.1 kb Sal fragment from the PRV g92 gene into the SalI site of pBR322 (U.S. Pat. No. 4,711,850).

FIG. 5B demonstrates that none of the IBRV(Los Angeles) restriction fragments hybridized with the pSal probe because the pSal probe contains only PRV g92 nucleotide sequences. FIG. 5B also demonstrates that cleavage of IBRVdltk(PRVg92) clone 6-2 with BamHI, HindIII, and PstI yields 3.0 kb, 24 kb, and 6.5 kb fragments, respectively, which hybridize with the pSal probe, and cleavage with KpnI yields two fragments, 5.9 kb and 4.2 kb, which hybridize with the pSal probe. These results demonstrate the IBRVdltk(PRVg92) clone 6-2 is a homologous recombinant between IBRV(Los Angeles) and pSP65/IBRVtk/PRVg92.

EXAMPLE 3

Construction of a $gIII^-$ IBRV-Based Viral Vector Expressing the PRV tk Gene Driven by the IBRV gIII Promoter This example describes a method for the production of an IBRV-based viral vector having a foreign gene inserted in the IBRV gIII gene so that the IBRV-based viral vector fails to produce any antigenic IBRV gIII polypeptides, and in which the expression of the foreign gene is driven by the IBRV gIII gene promoter. In this example, the foreign gene expressed in the IBRV-based viral vector is the PRV tk gene and PRV nucleotide sequences provide the translational stop and polyadenylation signals for the PRV tk gene. In addition to the foreign gene insertion, the IBRV-based viral vector of this example is "marked" by deletion of the IBRV tk gene sequences, the insertion of the 40 bp "NG" oligonucleotide sequence into the IBRV tk gene, and by the deletion of IBRV gIII gene sequences. IBRV-based viral vectors expressing the PRV tk gene may have restored virulence, so that the PRV tk gene insertion mutants of IBRV are not suitable as vaccines.

In this example, the foreign gene sequence inserted in the IBRV-based viral vector is derived from PRV. However, other viral, eucaryotic, or procaryotic genes may be used instead of the PRV gene without departing from the spirit and scope of this invention.

A. Construction of pLAHKdlApaI/PRVtk pLAHKdlApaI/PRVtk was obtained by inserting a 1.6 kb BamHI to KpnI fragment derived from pSP64/PRVtk containing the coding region of the PRV tk gene and PRV translational stop and polyadenylation signals into the BamHI site of pLAHKdlApaI (see FIG. 6).

Figure 6:
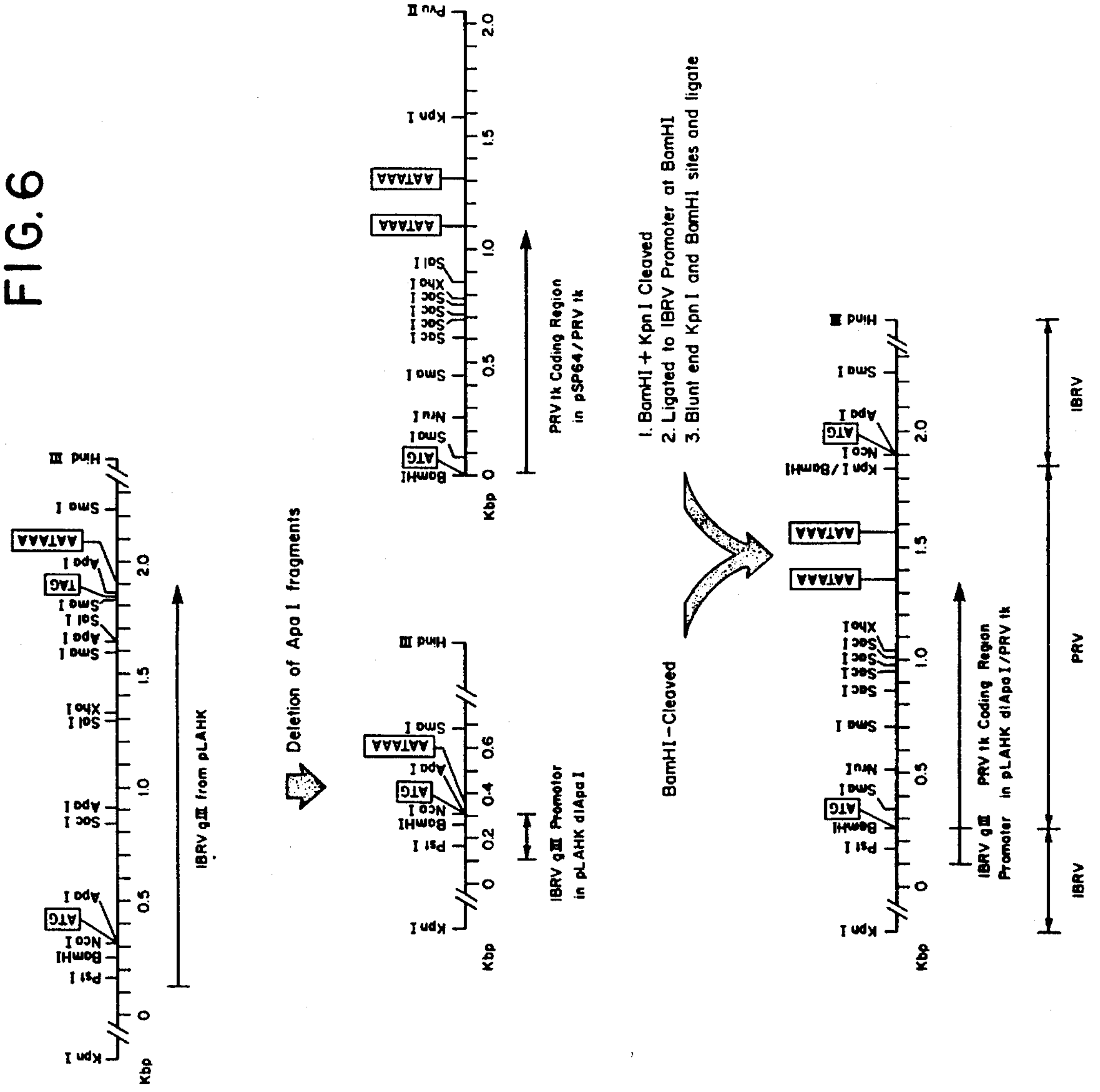
FIG. 6 schematically illustrates, by example, the derivation of pLAHKdlApaI/PRVtk. Specifically.

More specifically, 1.0 μg of pLAHKdlApaI, obtained as described in U.S. patent application Ser. No. 116,197, filed Nov. 3, 1987, now U.S. Pat. No. 4,992,051 was digested with 10 units of BamHI in 20 μl of buffer comprising 150 mM NaCl, 6.0 mM Tris-HCl (pH 7.9), 6.0 mM MgCl, and 100 μg/ml of BSA at 37° C. for 2 hr. The terminal ends of the BamHI-cleaved pLAHKdlApaI were dephosphorylated by adding 5.0 μl of buffer comprising 0.5M Tris-HCl (pH 8.0), and 0.5M NaCl, and 1.0 μl (1.0 unit) of bacterial alkaline phosphatase (International Biotechnologies, Inc.) and incubating at 65° C. for 1 hr. The enzyme was inactivated by adding Proteinase K at a final concentration of 100 μg/ml and incubating at 37° C. for 30 min. The reaction mixture was treated with an equal volume of phenol:chloroform (1:1) (v/v), and the BamHI-cleaved and -dephosphorylated pLAHKdlApaI was precipitated from the aqueous phase with 2 volumes of ethanol.

pSP64(PRVtk), which contains the coding region of the PRV tk gene ligated to the SP6 promoter in pSP64 (Promega Biotech) was prepared by cloning the coding region of the PRV tk gene and sequences 3' to the PRV tk gene i.e, the 2.2 kb BamHI to PvuII fragment shown in FIG. 6, into the unique BamHI and SmaI sites of the polyclonal cassette of pSP64 (Promega Biotech).

5.0 μg of pSP64(PRVtk) was digested with 50 units of KpnI in 20 μl of buffer comprising 6.0 mM NaCl, 6.0 mM Tris-HCl (pH 7.5), 6.0 mM MgCl, 1.0 mM dithiothreitol, and 100 μg/ml of BSA at 37° C. for 2 hr, and then digested with 50 units of BamHI in 100 μl of buffer comprising 150 mM NaCl, 6.0 mM Tris-HCl (pH 7.9), 6.0 mM $MgCl_2$, and 100 μg/ml of BSA at 37° C. for 2 hr. The reaction mixture was treated with an equal volume of phenol:chloroform (1:1) (v/v), and the DNA was precipitated with 2 volumes of ethanol.

The BamHI-cleaved and -dephosphorylated pLAHKdlApaI and the KpnI and BamHI-cleaved pSP64(PRVtk) were redissolved and combined in 40 μl of buffer comprising 50 mM Tris-HCl (pH 7.8), 10 mM MgCl, 20 mM dithiothreitol, 1.0 mM ATP, and 50 μg/ml of BSA. The DNA fragments were ligated together by adding 400 units of T4 ligase and incubated at 4° C. for 16 hr. The ligation mixture was treated with an equal volume of phenol:chloroform (1:1) (v/v), and the DNA was precipitated with 2 volumes of ethanol. The ligated DNA was redigested with 10 units of KpnI as described above and precipitated with 2 volumes of ethanol. To convert 3' overhanging KpnI and 5' overhanging BamHI ends to blunt ends, the DNA was next incubated in 20 μl of buffer comprising 50 mM Tris-acetate (pH 8.5), 50 mM potassium acetate, 5.0 mM magnesium acetate, 2.0 mM dithiothreitol, 0.1 mM each dNTP, and 1.0 unit of T4 DNA polymerase (Bethesda Research Laboratories) at 37° C. for 10 min. The DNA was precipitated by adding 10 μl of 7.5M ammonium acetate and 60 μl of ethanol, and ligated, as described above.

*E. coli* K12 strain RR1 was transformed with the resulting hybrid plasmids and the hybrid plasmid DNA of recombinant clones was isolated by the rapid screening procedure described in U.S. Pat. No. 4,514,497. Restriction endonuclease mapping identified the desired 10.3 kb plasmid, designated pLAHKdlApaI/PRVtk (see FIG. 6).

B. Construction of $gIII^-$ IBRV(NG)dltkdlgIII(PRVtk)

In order to obtain, by homologous recombination, a $gIII^-$ IBRV deletion/insertion mutant in which the PRV tk gene replaces the coding region of the IBRV gIII gene so that the PRV tk gene is expressed under the control of the IBRV gIII gene promoter, the intact DNA of infectious IBRV(NG)dltkdlgIII, in which a part of the IBRV tk gene and the entire coding region of the IBRV gIII gene are deleted (U.S. Pat. No. 4,703,011), was mixed with a hybrid plasmid containing an insertion of the PRV tk gene adjacent to an IBRV gIII gene promoter. The progeny virus obtained following this type of cross mainly comprised parental IBRV(NG)dltkdlgIII. Thus, in order to enrich for the IBRV recombinants, the progeny virus was passaged in $tk^-$ Rab(BU) cells in HATG media (U.S. Pat. No. 4,703,011; U.S. Pat. No. 4,514,497).

The hybrid plasmid chosen for the construction of this $gIII^-$ IBRV deletion/insertion mutant was pLAHKdlApaI/PRVtk (see FIG. 6). More specifically, 10 μg of pLAHKdlApaI/PRVtk was digested with 50 units of HindIII in 50 μl of buffer comprising 50 mM NaCl, 50 mM Tris-HCl (pH 8.0), 10 mM MgCl, and 100 μg/ml of BSA at 37° C. for 90 min. The reaction mixture was extracted with phenol:chloroform (1:1) (v/v) and dialyzed extensively against 0.1×TE buffer, adjusted to 10 μg/ml, and filter sterilized.

BK cells (Engel, S. et al, *Virus Res.*, 6:57–73 (1986/1987)) were seeded in 60 mm Petri dishes ($2\times10^5$ cells per 5.0 ml of growth media per dish) and incubated at 37° C. for 48 hr. Then, the following sterile solutions were added to a test tube in sequential order:

(1) 0.02 ml of a 50 μg/ml solution of IBRV(NG)dltkdlgIII DNA in TE buffer;

(2) 0.2 ml of a 10 μg/ml solution of pLAHKdlApaI/PRVtk cleaved with HindIII in 0.1×TE buffer;

(3) 0.65 ml of water;

(4) 1.0 ml of a 20 μg/ml solution of salmon sperm DNA in 2×Hepes buffer solution; and (5) 0.13 ml of 2.0M $CaCl_2$.

The resulting solution was mixed by inversion and kept at room temperature for 30 min while a DNA-calcium phosphate precipitate formed. Then, 0.5 ml of the suspension containing a calcium phosphate precipitate of DNA was added directly to 5.0 ml of growth media and plated on the BK cells in Petri dishes which had been seeded 48 hr earlier. The cells were incubated at 37° C. for 5 hr. Then, the growth media was aspirated, and the monolayer rinsed with 5.0 ml of fresh growth media, followed by the addition of 1.0 ml of a solution of 1.0×Hepes buffer solution plus 15% (v/v) glycerol. After a 3-min incubation at room temperature, the solution was aspirated, the monolayer was rinsed with growth media again, and fresh growth media was added. The culture was incubated at 37° C. for 3 days until extensive cytopathic effects occurred. Virus harvests were made as described in U.S. Pat. Nos. 4,514,497 and 4,703,011, and stored at −80° C. The virus harvests were then titrated in BK cells under a 0.5% (w/v) agarose overlay.

The virus harvests from the co-transfection, were thawed, sonicated and diluted in growth media. In order to enrich for $tk^+$ IBRV insertion mutants, $tk^-$ Rab(BU) cells were inoculated in four-ounce bottles at $2\times10^6$ cells per 10 ml growth media per bottle and incubated at 37° C. for 24 hr. The growth media was removed, the cell monolayer infected with 10 p.f.u. of the virus at 37° C. for 1 hr, and then 10 ml of HATG media was added. Incubation was continued at 37° C. for another 48 hr and viruses were harvested and titrated in BK cells and diluted to about 100 p.f.u./ml.

Next, BK cells were seeded in 60 mm Petri dishes at $2\times10^5$ cells per 5.0 ml growth media per dish and incubated at 37° C. for 48 hr. They were then infected with 20 p.f.u. of the HATG-selected virus for 1 hr, overlayed with 0.5% (w/v) agarose in growth media, and incubated at 37° C. for 3 days. Plaques were visualized by adding a second 0.5% (w/v) agarose overlay containing 0.01% (w/v) Neutral Red and incubating at 37° C. overnight. Viruses were isolated from individual plaques by stabbing with sterilized toothpicks and then infecting BK cells, which had been seeded in the wells of 96-well tissue culture clusters (Costar) at $2\times10^4$ cells per 0.2 ml growth media per well and incubating at 37° C. for 48 hr. In this manner, 192 clones of HATG-selected viruses were isolated from individual plaques (2×96-well tissue culture clusters). The 96-well tissue culture clusters were incubated at 37° C. for 3 days and stored at −80° C., and served as master plates.

C. Preparation of $^{32}P$-labeled pSP64/PRVtk Probe

To identify recombinant virus among the candidate clones, and to verify that insertions of foreign DNA existed in the IBRV gIII gene, molecular hybridizations were carried out with a $^{32}P$-labeled probe derived from the foreign DNA, i.e., the PRV tk gene in pSP64/PRVtk. As described above, pSP64/PRVtk was derived by cloning the coding region of the PRV tk gene and sequences 3' to the PRV tk gene (i.e., the 2.2 kb BamHI to PvuII fragment shown in FIG. 6) into the unique BamHI and SmaI sites of the polyclonal cassette of pSP64 (Promega Biotech). It should be noted that the ends of SmaI and PvuII may be ligated together because they are blunt-ended. The $^{32}P$ nick-translated pSP64/PRVtk probe was prepared in the same manner as described above for the *E. coli* lacZ probe.

D. Identification of Recombinant $gIII^-$ IBRV Deletion/Insertion Mutants of IBRV(NG)dltkdlgIII by Molecular Hybridization Viral DNAs prepared from each of the 192 clones of HATG-selected viruses described above were analyzed by the dot-blot method as described below using the $^{32}P$-labeled pSP64/PRVtk probe, which contains coding sequences for the PRV tk gene, so as to identify viruses that had an insertion of the 1.6 kb fragment of the PRV tk gene from pLAHKdlApaI/PRVtk in the IBRV gIII gene.

BK cells were seeded in 2×96-well tissue culture clusters as described above, incubated at 37° C. for 48 hr, and each well was infected with 50 μl of growth media from the well in the same location of the master plates described above. The duplicate plates were incubated at 37° C. for 48 hr. The growth media was removed from each well by aspiration, and 50 μl of 0.5 N NaOH was added to lyse the cells and release the DNA. After incubation at room temperature overnight, 75 μl of 1.0M Tris-HCl (pH 7.5), and 125 μl of 20×SSC were added to each well. Thereafter, dot-blot analysis was carried out as described above using the $^{32}P$-labeled pSP64/PRVtk probe.

Autoradiography was also carried out as described above.

Twenty-three out of the 192 candidate IBRV recombinants were found to hybridize with the pSP64/PRVtk probe. One of these clones was designated as IBRV(NG)dltkdlgIII(PRVtk) clone 14 and was saved for further analyses.

E. Analysis of Viral DNA

Figure 7A:
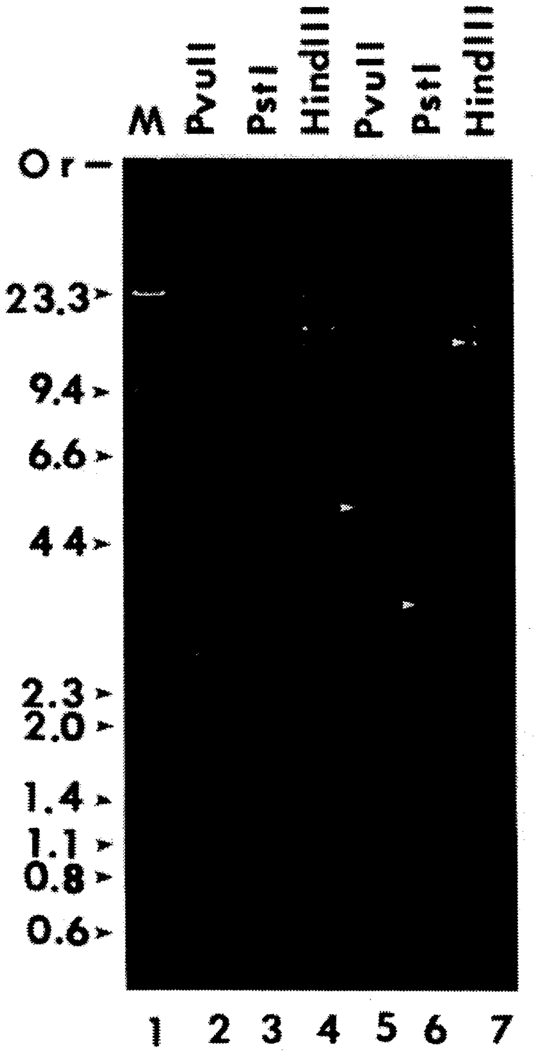
FIG. 7A shows ethidium bromide-stained agarose gel fragments of PvuII-, PstI- and HindIII-digested DNA from the parental $tk^-$ IBRV(NG)dltkdlgIII strain (lanes 2 to 4) and from the recombinant IBRV(NG)dltkdlgIII(PRVtk) (lanes 5 to 7), which contains the BamHI to KpnI fragment of the coding region of the PRV tk gene ligated to the BamHI site of the promoter region of the IBRV gIII gene (see FIG. 6). Lane 1 shows the size in kb of marker fragments from HindIII-digested lambda phage DNA and HaeIII-digested phage ΦX174 DNA. The arrows point to the fragments which hybridize with the pSP64/PRVtk probe shown in FIG. 7B.

Viral DNA of high purity was prepared from the IBRV recombinant IBRV(NG)dltkdlgIII(PRVtk) clone 14 as described in U.S. Pat. No. 4,703,011. Then, each of three 1.0 μg samples of viral DNA were cleaved, respectively, with PvuII, PstI, or HindIII, and the fragments were separated by electrophoresis on a 0.6% (w/v) agarose gel, as described above. DNA from the parental virus, $tk^-$ IBRV(NG)dltkdlgIII, was also treated in the same manner. The gel was stained with ethidium bromide and photographed as described above. The results are shown in FIG. 7A.

It has been determined that the 10.5 kb HindIII fragment, the 1.8 kb PstI fragment, and the 3.3 kb PvuII fragment of IBRV(NG)dltkdlgIII contain the promoter region of the IBRV gIII gene (U.S. patent application Ser. No. 116,197, filed Nov. 3, 1987 now U.S. Pat. No. 4,992,051). FIG. 7A demonstrates the 10.5 kb HindIII and 3.3 kb PvuII fragments are present in the parental IBRV(NG)dltkdlgIII DNA, but absent from the $gIII^-$ deletion/insertion mutant IBRV(NG)dltkdlgIII(PRVtk).

After the gel was stained with ethidium bromide and photographed, the separated DNA fragments in the agarose gel were transferred to nitrocellulose filters for Southern blot molecular hybridization as described above with the $^{32}P$-labeled pSP64/PRVtk probe. The results are shown in FIG. 7B.

Figure 7B:
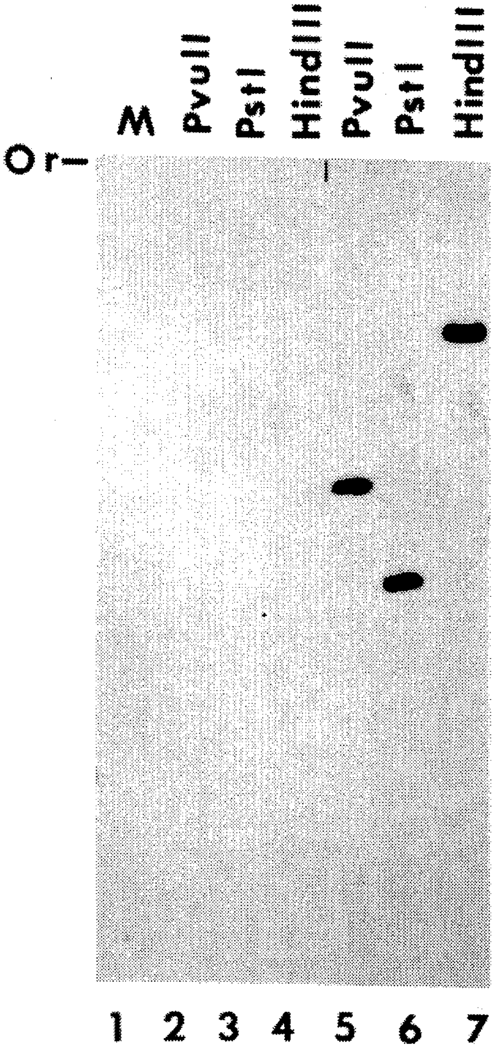
FIG. 7B shows autoradiographs demonstrating molecular hybridization of the $^{32}P$-labeled pSP64/PRVtk probe to DNA fragments of the $tk^+$ mutant IBRV(NG)dltkdlgIII(PRVtk), but not to DNA fragments of the parental $tk^-$ IBRV(NG)dltkdlgIII strain.

FIG. 7B demonstrates that the $^{32}P$-labeled pSP64/PRVtk probe does not hybridize to any of the parental virus DNA fragments, but hybridizes to the 12.1 kb HindIII, 3.4 kb PstI, and 5.2 kb PvuII fragments of the $gIII^-$ deletion/insertion mutant IBRV(NG)dltkdlgIII(PRVtk). These are the results expected from the insertion of a 1.6 kb BamHI to KpnI fragment of PRV DNA at the BamHI cleavage site of the IBRV gIII promoter (see FIG. 6). These results demonstrate that the $gIII^-$ deletion/insertion mutant IBRV(NG)dltkdlgIII(PRVtk) clone 14 is a homologous recombinant between IBRV(NG)dltkdlgIII and pLAHKdlApaI/PRVtk, and that, in the recombinant virus, the PRV tk coding region is placed 3' to the IBRV gIII gene promoter.

EXAMPLE 4

Construction of a $tk^-$ $gIII^-$ IBRV-Based Viral Vector Expressing the PRV g92 Gene Driven by the IBRV gIII Promoter This example also describes a method for the production of an IBRV-based viral vectors having a foreign gene inserted in the IBRV gIII gene so that the IBRV-based vital vector fails to produce any antigenic IBRV gIII polypeptides, and in which the expression of the foreign gene is driven by the IBRV gIII gene promoter. In this example, the foreign gene expressed in the IBRV-based vital vector is the PRV g92 gene and PRV nucleotide sequences provide the translational stop and polyadenylation signals for PRV g92 gene. In addition to the foreign gene insertion, the IBRV-based viral vector of this example is "marked" by the insertion of the 40 bp "NG" oligonucleotide sequence into the IBRV tk gene, and by the deletion of IBRV gIII gene sequences. The IBRV-based viral vector of this example is also attenuated by deletion of the IBRV tk gene, so that, like the $tk^-$ mutants IBRV(B8-D53) (ATCC No. 2066) and IBRV(NG)dltk (ATCC No. 2112), this IBRV-based viral vector expressing the PRV g92 gene may safely be employed as a vaccine (U.S. Pat. No. 4,703,011).

In this example, the foreign gene sequence inserted in the IBRV-based viral vector is derived from PRV. However, as discussed above, other viral, eucaryotic, or procaryotic genes may be used instead of the PRV genes without departing from the spirit and scope of this invention.

A. Construction of pLAHKdlApaI/pRVg92 pLAHdlApaI/PRVg92 was obtained by inserting a 2.4 kb NcoI fragment derived from pBUK:Stu12/PstI containing the coding region of the PRV g92 gene and PRV translational stop and polyadenylation signals into the NcoI site of pLAHKdlApaI.

More specifically, 1.0 μg of pLAHKdlApaI, obtained as described in U.S. patent application Ser. No. 116,197, filed Nov. 3, 1987, was digested with 10 units of NcoI in 20 μl of buffer comprising 150 mM NaCl, 6.0 mM Tris-HCl (pH 7.9), 6.0 mM MgCl, and 100 μg/ml of BSA at 37° C. for 2 hr. The terminal ends of the NcoI-cleaved pLAHKdlApaI were dephosphorylated by adding 5.0 μl of buffer comprising 0.5M Tris-HCl (pH 8.0) and 1.0 μl (1.0 unit) of bacterial alkaline phosphatase and incubating at 65° C. for 1 hr. The enzyme was inactivated by adding Proteinase K at a final concentration of 100 μg/ml and incubating at 37° C. for 30 min. The reaction mixture was treated with an equal volume of phenol:chloroform (1:1) (v/v), and the NcoI-cleaved and dephosphorylated pLAHKdlApaI precipitated from the aqueous phase with 2 volumes of ethanol.

pBUK:Stu12/PstI, which contains the PRV g92 gene (see FIG. 3 and FIG. 8), was obtained as described in U.S. Pat. No. 4,711,850.

5.0 μg of pBUK:Stu12/PstI was digested with 50 units of NcoI in 50 μl of buffer comprising 150 mM NaCl, 6.0 mM Tris-HCl (pH 7.9), 6.0 mM MgCl, and 100 μg/ml of BSA at 37° C. for 2 hr, treated with an equal volume of phenol:chloroform (1:1) (v/v), and precipitated with 2 volumes of ethanol.

The NcoI-cleaved and -dephosphorylated pLAHKdlApaI and the NcoI-cleaved pBUK:Stu12/PstI were redissolved in 40 μl of buffer comprising 50 mM Tris-HCl (pH 7.8), 10 mM $MgCl_2$, 20 mM dithiothreitol, 1.0 mM ATP, and 50 μg/ml of BSA. The DNA fragments were ligated by adding 400 units of T4 ligase and incubating at 4° C. for 16 hr. The reaction was stopped by adding 0.16 ml of TE buffer.

*E. coli* K12 strain RR1 was transformed with the resulting hybrid plasmids and the hybrid plasmid DNA of recombinant clones was isolated by the rapid screening procedure described in U.S. Pat. No. 4,514,497. Restriction endonuclease mapping identified the desired 11.1 kb plasmid, designated pLAHKdlApaI/PRVg92 (see FIG. 8).

B. Construction of $tk^-$ $gIII^-$ IBRV(NG)dltkdlgIII(PRVg92)

In order to obtain, by homologous recombination, a $tk^-$ $gIII^-$ IBRV deletion/insertion mutant in which the PRV g92 gene replaces a coding region of the IBRV gIII gene so that the PRV g92 gene is expressed under the control of the IBRV gIII gene promoter, the intact DNA of infectious IBRV(NG)dltkdlgIII, in which part of the IBRV tk gene and the entire coding region of the IBRV gIII gene were deleted (U.S. Pat. No. 4,703,011 and U.S. patent application Ser. No. 116,197, filed Nov. 3, 1987 now U.S. Pat. No. 4,992,051), was mixed with a hybrid plasmid containing an insertion of the PRV g92 gene adjacent to an IBRV gIII gene promoter. The progeny virus obtained by this type of cross mainly comprised parental IBRV(NG)dltkdlgIII. Thus, in order to screen for IBRV recombinants, the progeny virus was hybridized to the pSal probe.

Figure 8:
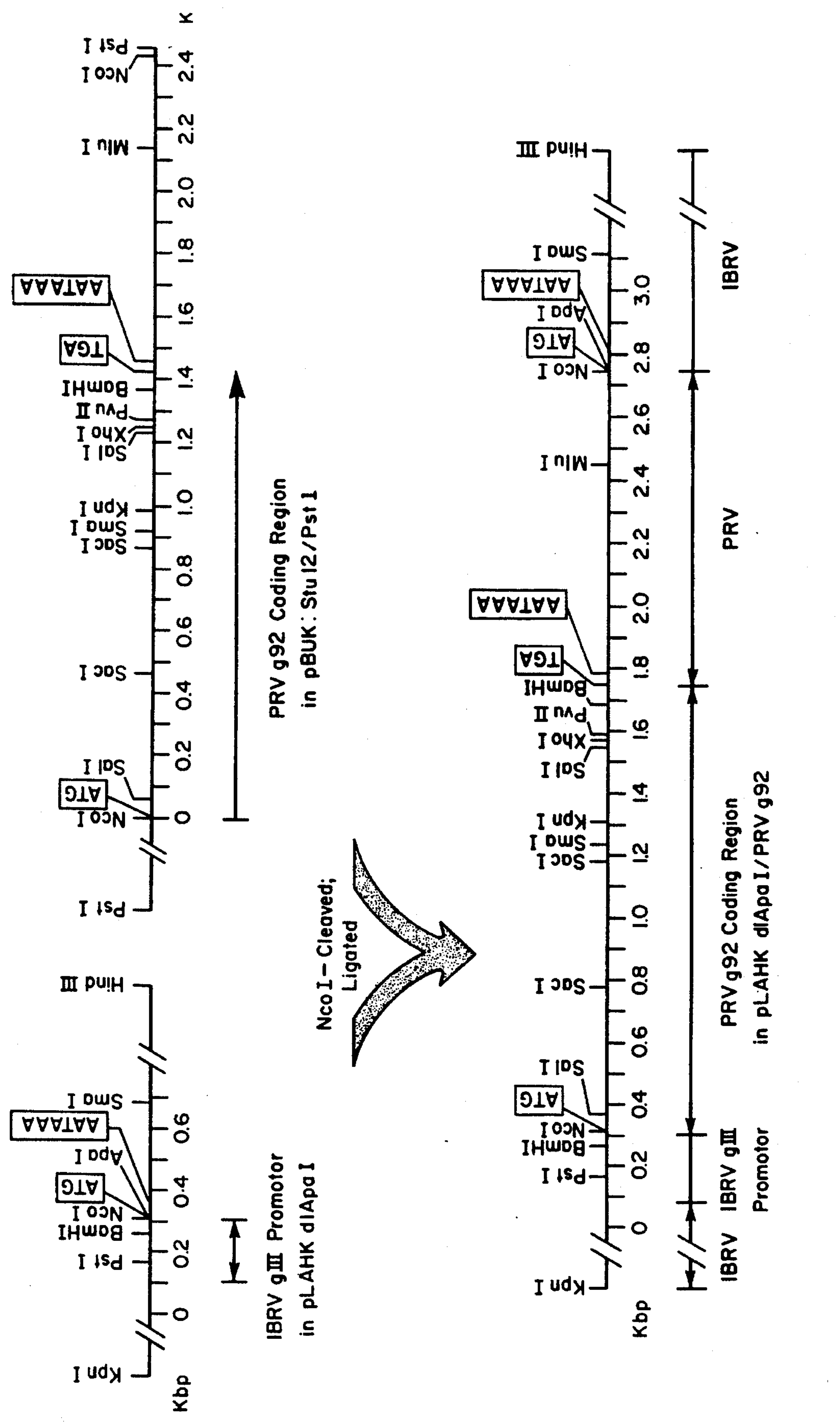
FIG. 8 schematically illustrates, by example, the restriction endonuclease maps of the IBRV gIII promoter in pLAHKdlApaI (see FIG. 6) and of the coding region of the PRV g92 gene in pBUK:Stu12/PstI (see FIG. 3). In order to insert the coding region of the PRV g92 gene and its 3' flanking sequences adjacent to the IBRV gIII promoter, pLAHKdlApaI and pBUK:Stu12/PstI were cleaved with NcoI and the resulting DNA fragments were religated to produce pLAHKdlApaI/PRVg92. Homologous recombination between pLAHKdlApaI/PRVg92 and infectious DNA from IBRV(NG)dltkdlgIII (U.S. Pat. No. 4,711,850 and U.S. patent application Ser. No. 116,197, filed Nov. 3, 1987 now U.S. Pat. No. 4,992,051) gave rise to the mutant IBRV(NG)dltkdlgIII(PRVg92) which expresses the PRV g92 gene from the IBRV gIII promoter.

The hybrid plasmid chosen for the construction of this $tk^-$ $gIII^-$ IBRV deletion/insertion mutant was pLAHKdlApaI/PRVg92 (see FIG. 8). More specifically, 10 μg of pLAHKdlApaI/PRVg92 was digested with 50 units of KpnI in 20 μl of buffer comprising 6.0 mM NaCl, 6.0 mM Tris-HCl (pH 7.5), 6.0 mM $MgCl_2$, and 100 μg/ml of BSA at 37° C. for 90 min, and then with 50 units of HindIII in 100 μl of buffer comprising 50 mM NaCl, 50 mM Tris-HCl (pH 8.0), 10 mM $MgCl_2$, and 100 μg/ml of BSA at 37° C. for 90 min. The reaction mixture was extracted with phenol:chloroform (1:1) (v/v) and dialyzed extensively against 0.1×TE buffer, adjusted to 10 μg/ml, and filter sterilized.

The construction of the recombinant insertion IBRV mutant of IBRV(NG)dltkdlgIII which expresses the PRV g92 gene was carried out as described using the KpnI plus HindIII-cleaved pLAHKdlApaI/PRVg92 in place of the HindIII-cleaved pLAHKdlApaI/PRVtk of Example 3 except that there was no enrichment step in HATG media.

C. Preparation of $^{32}P$-labeled pSal Probe

To identify recombinant virus among 192 candidate clones, and to verify that insertions of foreign DNA existed in the IBRV gIII gene, molecular hybridizations were carried with a $^{32}P$-labeled probe derived from the foreign DNA, i.e., the PRV g92 gene in pSal. As discussed above, pSal was obtained from pBUK:Stu12/PstI by subcloning the 1.1 kb SalI fragment of pBUK:Stu12/PstI into the SalI site of pBR322 as described in U.S. Pat. No. 4,711,850. The $^{32}P$-labeled pSal probe was also prepared as described in U.S. Pat. No. 4,711,850.

D. Identification of Recombinant $gIII^-$ IBRV by Molecular Hybridization

Viral DNAs prepared from each of the resulting 192 clones were analyzed by the dot-blot method as described below using the $^{32}P$-labeled pSal probe, which contains coding sequences from the PRV g92 gene, so as to identify viruses that had an insertion of the 2.4 kb fragment of the PRV g92 gene from pLAHKdlApaI/PRVg92 in the IBRV gIII gene.

BK cells were seeded in two of 96-well tissue culture clusters at $2\times10^4$ cells per 0.2 ml growth media per well and incubated at 37° C. for 48 hr, and each well was infected with 0.2 ml of the diluted virus suspension. Infected tissue culture clusters were incubated at 37° C. for 3 days and stored at −80° C. and served as master plates. A set of the duplicate of the master plates was prepared by infecting freshly prepared BK cells in each well of tissue culture clusters with 50 μl of growth media from the master plates. The duplicate plates were incubated at 37° C. for 48 hr. The growth media was removed from each well by aspiration, 50 μl of 0.5N NaOH was added to lyse the cells and release the DNA. After incubation at room temperature overnight, 75 μl of 1.0M Tris-HCl (pH 7.5) and 125 μl of 20×SSC buffer were added to each well. Thereafter, dot-blot analysis was carried out as discussed above using $^{32}P$-labeled pSal probe.

Autoradiography was also carried out as described above.

Three out of the 192 infected wells found to hybridize with the pSal probe. Since each well was originally infected with 20 clones of viruses, this indicates that 3 homologous recombinants were present among 3,840 candidate clones. Individual clones of viruses were isolated from the wells which contained homologous recombinants, and dot-blot analyses was carried out again in the same manner as described above. Two of the isolated homologous recombinants were designated IBRV(NG)dltkdlgIII(PRVg92) clone 7 and clone 9 and were saved for further analysis. IBRV(NG)dltkdlgIII(PRVg92) clone 9 has been deposited with the American Type Culture Collection under ATCC No. VR 2192.

E. Analysis of Viral DNA

Viral DNA of high purity was prepared from IBRV(NG)dltkdlgIII(PRVg92) clone 7 and clone 9 as described in U.S. Pat. No. 4,703,011. Then, each of three 1.0 μg samples of viral DNA were cleaved, respectively, with HindIII, KpnI, or PstI, and DNA fragments were separated by electrophoresis on a 0 6% (w/v) agarose gel as described above. DNAs from parental virus, IBRV(NG)dltkdlgIII, and from pLAHKdlApaI/PRVg92, were also treated in the same manner. The gel was stained with ethidium bromide and photographed as described above. The results are shown in FIG. 9A.

Figure 9B:
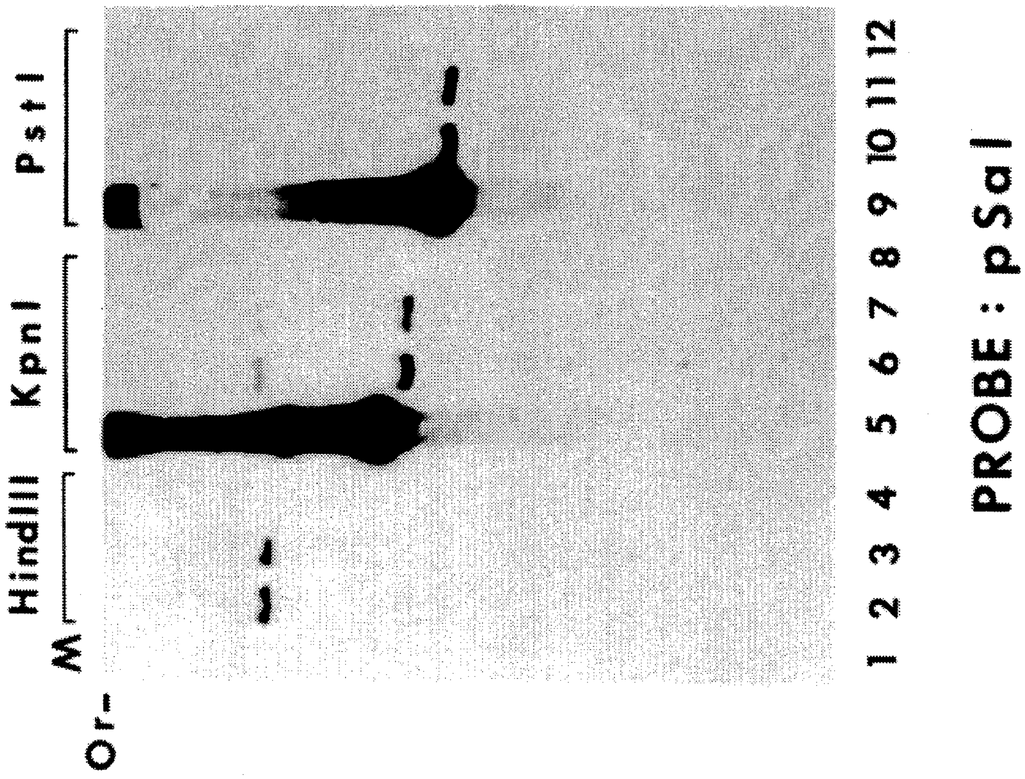
FIG. 9B shows autoradiographs demonstrating molecular hybridization of the $^{32}P$-labeled pSal probe to DNA fragments from IBRV(NG)dltkdlgIII(PRVg92) clones 7 and 9, and to pLAHKdlApaI/PRVg92, all of which contain PRV DNA inserts, but not to DNA fragments from the parental $tk^-$ IBRV(NG)dltkdlgIII strain.
Figure 9A:
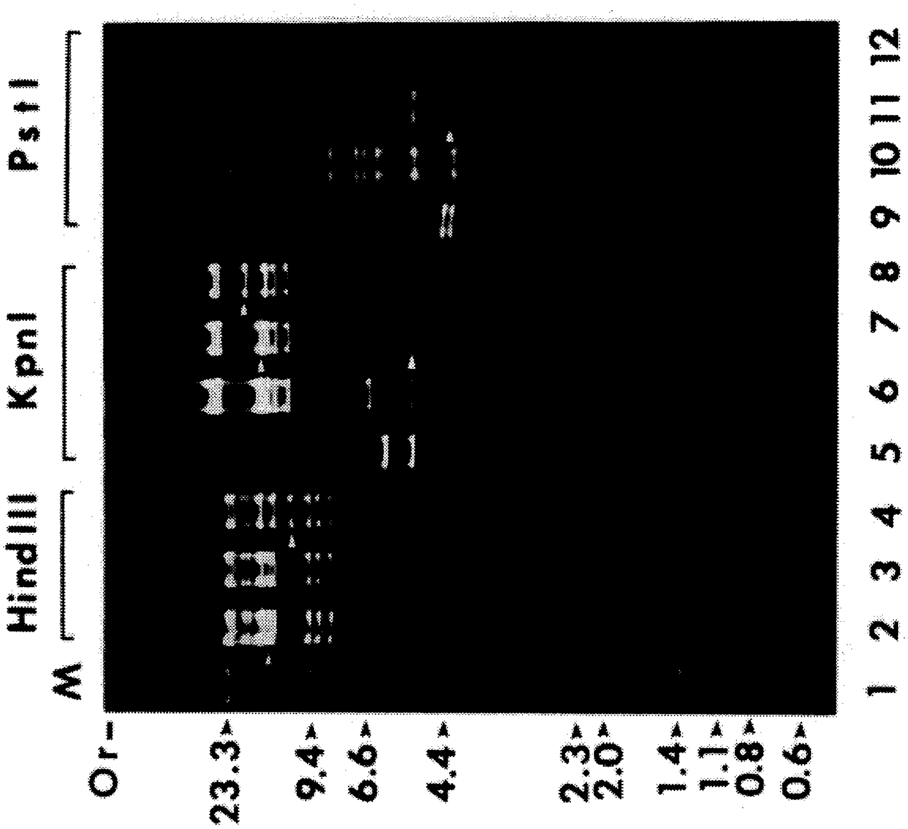
FIG. 9A shows ethidium bromide-stained agarose gel fragments of HindIII-, KpnI- and PstI-digested DNA from the parental $tk^-$ IBRV(NG)dltkdlgIII strain (lanes 4, 8 and 12) and from the recombinants IBRV(NG)dltkdlgIII(PRVg92) clone 7 (lanes 3, 7 and 11) and IBRV(NG)dltkdlgIII(PRVg92) clone 9 (lanes 2, 6 and 10), which express the PRV g92 gene. Lanes 5 and 9, respectively, show KpnI and PstI fragments obtained by restriction endonuclease digestion of pLAHKdlApaI/PRVg92. Lane 1 shows the size in kb of marker fragments from HindIII-digested phage lambda DNA and HaeIII-digested phage ΦX174 DNA. The arrows point to DNA fragments which differ in size in the parental and recombinant viruses.

FIG. 9A demonstrates that the HindIII restriction endonuclease profiles of the recombinants and the parental DNA were similar except that the 10.5 kb fragment observed in the parental virus DNA was absent from the recombinant DNAs and a new 12.9 kb fragment was present in the recombinant virus DNAs, but not in the parental virus DNA.

After the gel was stained with ethidium bromide and photographed, the separated DNA fragments in the agarose gel were transferred to nitrocellulose membranes for Southern blot molecular hybridization as described above with the $^{32}$P-labeled pSal probe. The results are shown in FIG. 9B.

FIG. 9B demonstrates that the pSal probe hybridizes with the 12.9 kb HindIII fragment of the recombinant DNAs, but does not hybridize with any of the HindIII fragments of the parental virus DNA. The 10.5 kb HindIII fragment of IBRV(NG)dltkdlgIII contains the promoter region of the gIII gene (U.S. patent application Ser. No. 116,197, filed Nov. 3, 1987 now U.S. Pat. No. 4,992,051). These results demonstrate that the 2.4 kb DNA fragment from pLAHKdlApa/PRVg92, which contains the coding region of the PRVg92 gene, was incorporated by homologous recombination into the IBRV genome proximal to the IBRV gIII gene promoter. Further restriction endonuclease analyses with KpnI and PstI confirmed this conclusion (see FIG. 9A). The parental IBRV and the recombinant viruses differed in their KpnI restriction endonuclease profiles in that a 17 kb fragment was present in the parental virus but absent from the recombinant viruses, and that 14 kb and 5.3 kb fragments were present in the recombinant virus but absent from those of the parental virus. The 14 kb and 5.3 kb fragments of the recombinant viruses hybridized with the pSal probe, but the 17 kb fragment of the parental virus did not (see FIG. 9B). It should be noted that a 5.3 kb fragment is also present in the KpnI digest of pLAHKdlApaI/PRVg92 (see FIG. 9B, lane 5). Digestion with PstI yielded 4.3 kb fragments from the recombinant viruses and from pLAHKdlApaI/PRVg92 which also hybridized with the pSal probe.

Thus, the above results confirmed that IBRV(NG)dltkdlgIII(PRVg92) clone 7 and clone 9 contain the IBRV gIII gene promoter sequence, but that the IBRV gIII coding region was replaced with the coding region of the PRV g92 gene.

EXAMPLE 5

Phenotypic Properties of IBRV Insertion Mutants

A. Autoradiographic Analyses of the TK Enzyme Phenotype of Wild-type IBRV(Los Angeles) and of the Recombinant Strains It has previously been shown that the removal and/or functional inactivation of the thymidine kinase gene contributes to the attenuated properties of bovine and porcine herpesviruses (U.S. Pat. No. 4,569,840; U.S. Pat. No. 4,514,498; U.S. Pat. No. 4,609,548; U.S. Pat. No. 4,703,011; and U.S. Pat. No. 4,711,850). Thus, it was important to demonstrate that the recombinant IBRV mutants described herein, which contain inserts of foreign DNA, lack the ability to induce a functional TK enzyme activity.

In order to analyze the phenotypes of the wild-type IBRV(Los Angeles) and of the various recombinant IBRV strains described herein, autoradiographic experiments were performed on virus-infected cells. These experiments consisted of conventional autoradiographic analyses on glass slides and thymidine plaque autoradiographic analyses (U.S. Pat. No. 4,514,497; U.S. Pat. No. 4,703,011). Specifically, the conventional autoradiography analyses on glass slides were carried out as follows:

$tk^-$ Rab(BU) cells were seeded (50,000 cells/well) into an 8-well Lab-Tek™ (Miles Laboratories, Inc.) slide and incubated at 37° C. for 1–2 days until confluent. The cells were infected at about 10 p.f.u./cell with $tk^+$ IBRV(RTK-1B), with the $tk^-$ deletion mutant, IBRV(NG)dltk (ATCC No. VR 2112), which was derived from $tk^+$ IBRV(RTK-1B) (U.S. Pat. No. 4,703,011), or with the recombinant virus IBRV(βGalINV) (ATCC No. VR 2160) (see FIG. 2). After absorption at 37° C. for 1 hr, fresh growth media was added. At 3 hr postinfection, the growth media was changed to fresh growth media containing 5.0 μCi of 3H-dThd/ml and 0.1 μg/ml of cold dThd. At 20 hr postinfection, the growth media was aspirated and the cells were rinsed successively with 1×GKN and methanol, and then fixed in methanol at room temperature for 1 min. The wells and gasket were removed from the slide and the cells were washed at 4° C. for 5 min each with 5.0% (w/v) trichloroacetic acid (twice), 70% (v/v) ethanol (thrice), and 100% ethanol (twice). After drying in air, the slides were stained in 2.0% (w/v) acetic-orcein for 2 min, then destained in ethanol. The slides were dipped in autoradiographic photographic emulsion (Kodak-NTB2) at 40° C. and dried in a horizontal position for 1 hr. Then, the slides were placed in a darkened box with drierite and left at room temperature for 20 hr. The slides were developed in Kodak Dektol for 2 min at 16° C., rinsed in water for 10 sec, fixed in Kodak fixer for 5 min, and rinsed in water (twice), each for 2.5 min.

In all cells infected with IBRV(RTK-1B), i.e., a $tk^+$ IBRV, the nuclei were heavily labeled due to the phosphorylation of $^3$H-dThd by the IBRV TK enzyme, and the subsequent incorporation of the 3H-dTTP into acid insoluble nuclear DNA. As expected, $tk^-$ IBRV(NG)dltk and IBRV(βGalINV) produced pronounced cytopathic effects in the infected cells due to virus growth, but the nuclei of the cells infected with these viruses were not labeled because of the absence of a functional TK enzyme with which to phosphorylate the $^3$H-dThd. Thus, these experiments demonstrate that, like IBRV(NG)dltk, IBRV(βGalINV) was a $tk^-$ IBRV strain.

Thymidine plaque autoradiographic analyses were next carried out in $tk^-$ Rab(BU) cells as described in Kit, S. et al, *Am. J. Vet. Res.*, 48:780–793 (1987); and U.S. Pat. No. 4,514,497, to ascertain the TK phenotypes of IBRVdltk-(PRVg92) clone 6-2, IBRV(NG)dltkdlgIII(PRVg92) clone 9, and IBRV(NG)dltkdlgIII(PRVtk) clone 14. These experiments again showed that mock-infected $tk^-$ Rab(BU) cells did not have virus plaques and did not incorporate $^{14}$C-thymidine into cellular DNA. However, Rab(BU) monolayers infected with the wild-type $tk^+$ IBRV(Los Angeles), or with recombinant viruses IBRV(NG)dltkdlgIII (ATCC No. VR 2181), IBRVdltk(PRVg92) clone 6-2 (ATCC No. VR 2182), IBRV(NG)dltkdlgIII(PRVtk) clone 14, and IBRV(NG)dltkdlgIII(PRVg92) clone 9 (ATCC No. VR 2192), had many plaques. Plaques made by the wild-type IBRV(Los Angeles) were labeled with $^{14}$C-thymidine because this wild-type IBRV expressed an IBRV-encoded TK activity. Plaques made by IBRV(NG)dltkdlgIII were not labeled, nor were plaques made by recombinant IBRVdltk-(PRVg92) clone 6-2 or IBRV(NG)dltkdlgIII(PRVg92) clone 9, because IBRV(NG)dltkdlgIII, IBRVdltk(PRVg92) clone 6-2 and IBRV(NG)dltkdlgIII(PRVg92) clone 9 had deletions in the IBRV tk gene and they were not capable of inducing a functional TK activity. In contrast, plaques made by IBRV(NG)dltkdlgIII(PRVtk) clone 14 were heavily labeled with 14C-thymidine. Although IBRV(NG)dltkdlgIII(PRVtk) clone 14 has a deletion of the IBRV tk gene, it has an insertion of the coding region of the PRV tk gene adjacent to the IBRV gIII promoter. Hence, the PRV tk gene was expressed under the control of the IBRV gIII gene promoter, PRV TK enzyme was made, and the infected cells incorporated $^{14}$C-thymidine into DNA. The results therefore show that the insertion mutant, IBRV(NG)dltkdlgIII(PRVtk) clone 14 had a $tk^+$ phenotype and that insertion mutants IBRVdltk(PRVg92) clone 6-2 and IBRV(NG)dltkdlgIII(PRVg92) clone 9 had $tk^-$ phenotypes.

B. Detection of PRV g92 Following Infection of Rab-9 Cells With Recombinants IBRVdltk(PRVg92) and IBRVdtkdlgIII(PRVg92)

To verify that PRV g92 was expressed in cells infected with the recombinants IBRVdltk(PRVg92) clone 6-2 and clone 7-30 and with IBRVdltkdlgIII(PRVg92) clone 9, the following experiments were carried out.

Rab-9 cells were seeded in four-ounce prescription bottles at $2\times10^5$ cells per 10 ml APMEM supplemented with 10% (v/v) fetal calf serum per bottle and incubated at 37° C. for 2 days. In the first experiment, the cells were then infected with PRV(BUK-5) and IBRV(Los Angeles) as positive and negative controls, respectively, or with IBRVdltk(PRVg92) clones 6-2 and 7-30 at about 5.0 p.f.u./cell for 1 hr, washed with APMEM supplemented with 2.0% (v/v) fetal calf serum, and incubated in the same growth media at 34.5° C. for 3 hr. The cells were then washed with glucose-free Eagle's minimal essential media (hereinafter "MEM"), and 4.0 ml of a solution comprising glucose-free MEM containing 2.0% (v/v) dialyzed fetal calf serum and 100 μCi of D-(2,6-$^3$H)mannose (54 Ci/mmole, Amersham) was added. The cultures were further incubated at 34.5° C. for 20 hr, the growth media was removed by aspiration, 400 μl of extraction buffer comprising 1.0 (v/v) NP40, 0.0625M Tris-HCl (pH 7.0), and 0.9% (w/v) NaCl was added, the cells were quickly frozen at −80° C., thawed at 37° C., and the extract was transferred to a 1.5 ml plastic Eppendorf tube and sonicated for 45 sec.

70 μl of labeled extract from virus-infected cells was mixed with 30 μl of anti-PRV sera No. 18705 (Kit, S. et al, *Am. J. Vet. Res.*, 48:780–793 (1987)), incubated at 4° C. for 18 hr, and 150 μl of Pansorbin (formalin-fixed *Staphylococcus aureus* cells) (Calbiochem) was added. After 45 min of incubation at 4° C., the mixture was centrifuged at 10,000×g at 4° C. for 10 min. The supernatant was discarded and the pellet was washed 3 times with 300 μl of 0.05% (w/v) Tween 20 in PBS by repeated centrifugation. After the final wash, the pellet was suspended in 100 μl of buffer D comprising 0.3% (w/v) SDS, 0.7M 2-mercaptoethanol, 0.06M Tris-HCl (pH 6.8), 10% (v/v) glycerol, and 0.05% (w/v) bromophenol blue, heated in a boiling water bath for 10 min, and centrifuged at 10,000×g for 10 min. An aliquot of the supernatant was subjected to SDS-polyacrylamide gel electrophoresis (3.0% (w/v) stacking gel and 7.5% (w/v) running gel) at 40 V for 16 hr as described in U.S. Pat. No. 4,711,850. The gel was fixed in a 10% (v/v) acetic acid, 40% (v/v) methanol solution, stained with Commasie blue (0.2% (w/v) in the fixing solution), and soaked in Autoflour (autoradiographic image enhancer, National Diagnostic) for 1 hr, dried over a gel dryer (Model SE540, Hoeffer Scientific Instruments), and exposed to Fuji X-ray film at −80° C. for 4 days. The results are shown in FIG. 10.

Figure 10:
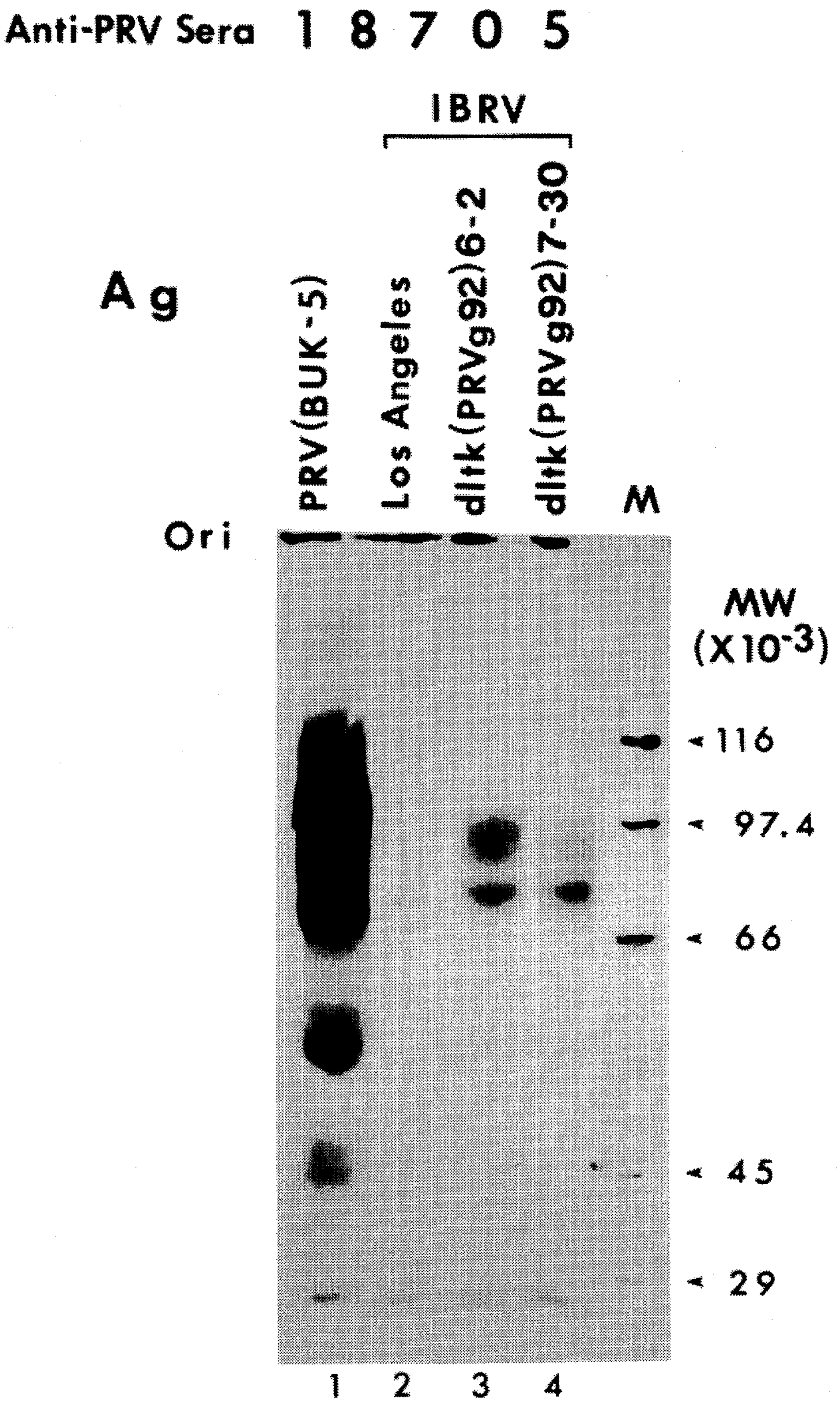
FIG. 10 illustrates immunoprecipitation experiments using anti-PRV sera 18705 (Kit, S. et al, *Am. J. Vet. Res,* 48:780–793 (1987)) to detect the PRV g92 antigen in detergent extracts of $^3H$-mannose-labeled cells infected with PRV(BUK-5) (U.S. Pat. Nos. 4,514,497 and 4,609,545), with IBRV(Los Angeles) and with recombinant IBRV viruses, IBRVdltk(PRVg92) clone 6-2 and clone 7-30.

FIG. 10 demonstrates that the anti-PRV sera No. 18705 immunoprecipitated mannose-labeled glycoproteins with molecular weights of about 115–122 kD, 92–97 kD, 72–78 kD, and 55–62 kD from extracts of PRV(BUK-5)-infected cells (Kit, S. et al, *Am. J. Vet. Res.*, 48:780–793 (1987)). The labeled 92–97 kD and 72–78 kD bands consist of PRV g92 and a PRV g92 precursor protein, respectively. FIG. 10 also demonstrates that anti-PRV sera No. 18705 does not immunoprecipitate any labeled glycoprotein from the wild-type IBRV(Los Angeles)-infected cells. However, this anti-PRV sera does immunoprecipitate labeled glycoproteins of 92–98 kD and 72–78 kD from extracts of recombinant IBRVdltk-(PRVg92) clones-6-2- and 7–30-infected cells. Additional control experiments demonstrated that labeled glycoproteins from mock-infected cells were not immunoprecipitated by anti-PRV sera No. 18705 nor by polyclonal anti-IBRV sera. Likewise, polyclonal anti-IBRV sera did not immunoprecipitate labeled glycoproteins from PRV-infected cells but, as expected, did precipitate IBRV-specific glycoproteins with molecular weights of about 180 kD, 150 kD, 130 kD, 97 kD, 74–77 kD, and 55 kD from extracts of cells infected with IBRV(Los Angeles) and IBRVdltk(PRVg92) clone 6-2 (Marshall, R. L. et al, *J. Virol.*, 57:745–753 (1986)). These results demonstrate that both the PRV g92 gene, which had been inserted into the IBRV tk gene of IBRV(Los Angeles), and IBRV-specific glycoprotein genes were expressed in the recombinant IBRV insertion mutant, IBRVdltk(PRVg92).

Figure 11:
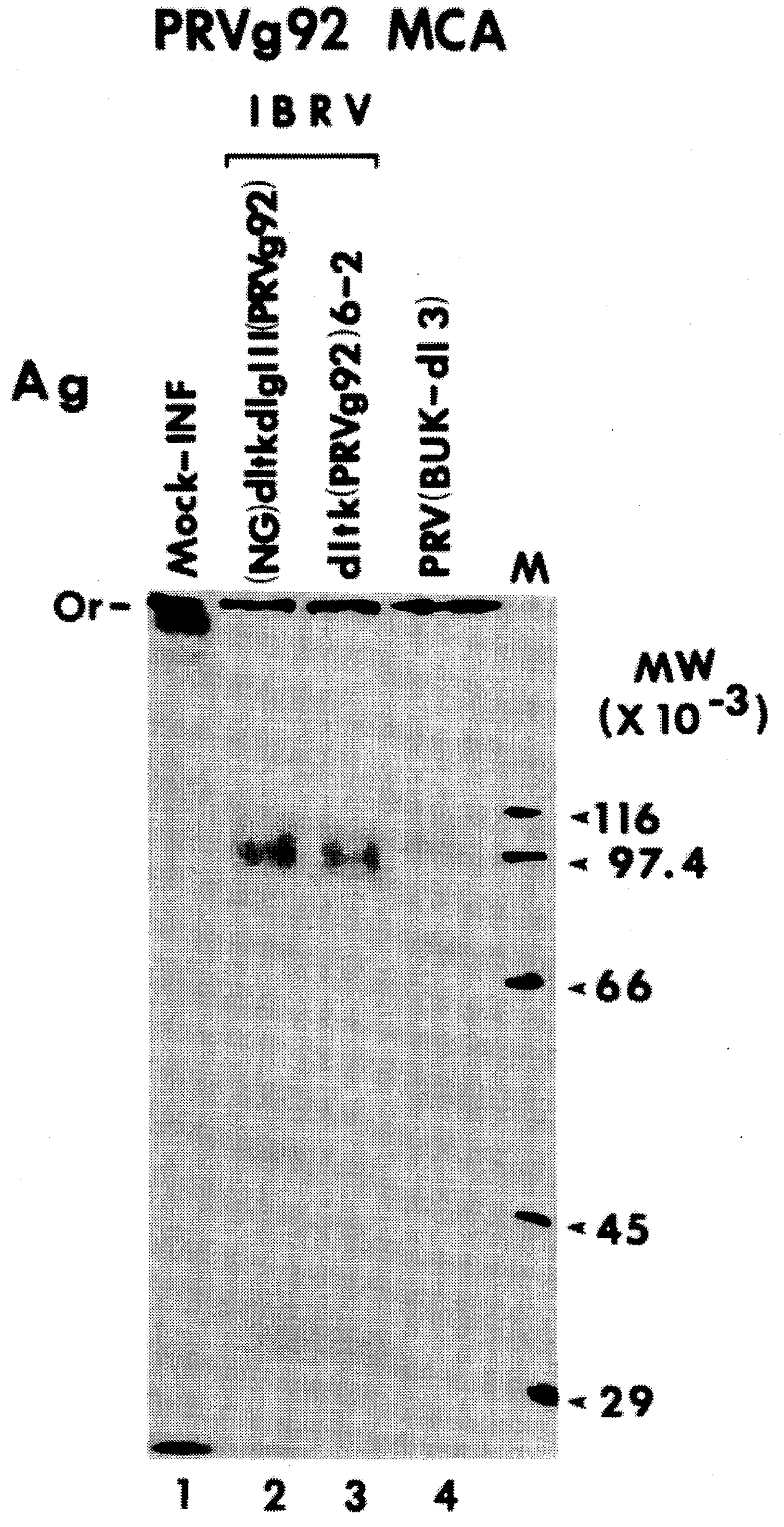
FIG. 11 illustrates immunoprecipitation experiments using anti-PRV g92 monoclonal antibodies ("MCA") to detect the PRV g92 antigen in detergent extracts of $^3H$-mannose-labeled cells infected with PRV(BUK-d13) (U.S. Pat. Nos. 4,514,497 and 4,609,545), and with recombinant IBRV viruses, IBRVdltk(PRVg92) clone 6-2 and IBRV(NG)dltkdlgIII(PRVg92) clone 9.

In the second experiment, the results of which are shown in FIG. 11, $^3$H-mannose-labeled extracts from mock-infected cells, from cells infected with IBRVdltk(PRVg92) clone 6-2, IBRV(NG)dltkdlgIII(PRVg92) clone 9, and from the $g92^+$ PRV(BUK-dl 3) strain (Kit, S. et al, *Am. J. Vet. Res.*, 46:1359–1367 (1985) and U.S. Pat. No. 4,514,497) were immunoprecipitated with anti-PRV g92 monoclonal antibodies (Kit, S. et al, *Am. J. Vet. Res.*, 48:780–793 (1987)). As shown in FIG. 11, the 92–97 kD PRV g92 was precipitated from the extracts from each of the virus-infected cells, but not from extracts of the mock-infected cells. Hence, these results conclusively demonstrate that the insertion mutants, IBRV(NG)dltk(PRVg92) clone 6-2 and IBRV(NG)dltkdlgIII(PRVg92) clone 9, were expressing the PRV g92 gene under the control of the IBRV gIII gene promoter.

C. Temperature Resistance of IBRV(Los Angeles) and IBRVdltk(PRVg92) Clone 6-2

Replicate, subconfluent monolayer cultures of BK cells were infected with the wild-type IBRV(Los Angeles) or with IBRVdltk(PRVg92) clone 6-2 at an input multiplicity of about 0.01 p.f.u./cell, and incubated in a $CO_2$ incubator at 34.5° C. and 39.1° C. Virus harvests were prepared at 3 hr and at 48 hr after infection and plaque-titrated at 34.5° C. and 39.1° C. in BK cells as described in U.S. Pat. No. 4,703,011. The results are shown in the Table below.

TABLE

REPLICATION FOR 48 HR AT 34.5° C. OR 39.1° C. OF WILD-TYPE AND MUTANT IBRV STRAINS

| Virus | Temperature of virus growth | Virus yield (p.f.u.) when plaque titrated at: | |
|---|---|---|---|
| | | 34.5° C. | 39.1° C. |
| IBRV(Los Angeles) | 34.5° C. | $7.7 \times 10^7$ | $1.1 \times 10^8$ |
| | 39.1° C. | $3.9 \times 10^7$ | $5.6 \times 10^7$ |
| IBRVdltk(PRVg92) | 34.5° C. | $7.0 \times 10^7$ | $6.0 \times 10^7$ |
| clone 6-2 | 39.1° C. | $4.8 \times 10^7$ | $3.5 \times 10^7$ |

Approximately $10^3$ p.f.u./ml of virus was obtained when harvests were prepared at 3 hr after infection. This represents the virus present immediately after the absorption and penetration of the input virus. The above Table demonstrates that at 48 hr after infection of BK cells at 34.5° C. with IBRV(Los Angeles) and IBRVdltk(PRVg92) clone 6-2, respectively, the virus yields had increased to $7.7 \times 10^7$ and $7.0 \times 10^7$ p.f.u./ml (titrations at 34.5° C.). The 48 hr yields of the IBRV(Los Angeles) and IBRVdltk(PRVg92) clone 6-2 grown at 39.1° C., respectively, were about $3.9 \times 10^7$ and $4.8 \times 10^7$ p.f.u./ml (titrations at 34.5° C.), respectively. Within experimental error, the yields were similar for titrations performed at 39.1° C. and 34.5° C. Thus, it is clear that the recombinant virus, tk⁻ IBRVdltk(PRVg92) clone 6-2 can grow about as well over the temperature range of 34.5° C. to 39.1° C. as the wild-type IBRV(Los Angeles) strain. That is, neither virus exhibits temperature-sensitive properties. In this regard, recombinant tk⁻ IBRVdltk(PRVg92) clone 6-2 also resembles the tk⁻ IBRV strains previously described, that is, IBRV(B8-D53), IBRV(NG)dltk, and IBRVdltkdlgIII, in their temperature-resistant properties (U.S. Pat. No. 4,569,840; U.S. Pat. No. 4,703,011; and U.S. patent application Ser. No. 116,197, filed Nov. 3, 1987 now U.S. Pat. No. 4,992,051).

While this invention has been described in detail with reference to specific embodiments thereof, it will be apparent to one skilled in the art that various changes and modifications can be made therein without departing from the spirit and scope thereof.

We claim:

1. An infectious bovine rhinotracheitis virus which fails to produce any functional thymidine kinase as a result of an insertion in the thymidine kinase gene.

2. The infectious bovine rhinotracheitis virus as claimed in claim 1, wherein said insertion is about 8 to 5000 bp in size.

3. The infectious bovine rhinotracheitis virus as claimed in claim 1, wherein said insertion is a foreign gene which is inserted in a manner such that it is not expressed by said virus.

4. The infectious bovine rhinotracheitis virus as claimed in claim 1, wherein said virus is also temperature-resistant.

5. The infectious bovine rhinotracheitis virus as claimed in claim 1, wherein said virus has the identifying characteristics of IBRV(βGalINV) (ATCC No. VR 2160).

6. The infectious bovine rhinotracheitis virus as claimed in claim 1, wherein said virus is lyopholized.

7. An infectious bovine rhinotracheitis virus which fails to produce any functional thymidine kinase as a result of an insertion in the IBRV tk gene produced by the process comprising:

(1) constructing a hybrid plasmid comprising a cloning vector and a DNA fragment of IBRV containing substantially all of the IBRV tk gene and flanking sequences thereof;

(2) inserting a foreign DNA sequence within the IBRV tk gene of the resulting hybrid plasmid of step (1);

(3) co-transfecting, in tk⁺ IBRV host cells, the hybrid plasmid of step (2) with infectious DNA from a tk⁺ IBRV; and (4) selecting or screening, in tk⁻ IBRV host cells, for tk⁻ IBRV from the virus produced in step (3) so as to produce an infectious bovine rhinotracheitis virus mutant which fails to produce any functional thymidine kinase as a result of an insertion in the IBRV tk gene.

8. The infectious bovine rhinotracheitis virus as claimed in claim 7, wherein said insertion is about 8 to 5000 bp in size.

9. The infectious bovine rhinotracheitis virus as claimed in claim 7, wherein said insertion is a foreign gene which is inserted in a manner such that it is not expressed by said virus.

10. The infectious bovine rhinotracheitis virus as claimed in claim 7, wherein the infectious DNA of step (3) is derived from a temperature-resistant infectious bovine rhinotracheitis virus such that the resulting mutant of step (4) is also temperature-resistant.

11. The infectious bovine rhinotracheitis virus as claimed in claim 7, additionally comprising step (5):

(5) propagating the resulting infectious bovine rhinotracheitis virus mutant of step (4) at a non-permissive temperature for a temperature-sensitive virus so as to select for and produce a temperature-resistant infectious bovine rhinotracheitis virus mutant which fails to produce any functional thymidine kinase as a result of an insertion in the IBRV tk gene.

12. The infectious bovine rhinotracheitis virus as claimed in claim 7, wherein said cloning vector is selected from the group consisting of pBR322, pMB9, pBR325, pKH47, pUC18, pUC19, pBR328, pHC79, phage Charon 28, pKB11, pKSV-10, pPROK-1, pYEJ001, pKC30, pKT280, pEUK-C1, pEUK-C2, pWE15, pMAM, pMAM-neo, pCH110, pdBPV-MMTneo, pMAR420 and oligo(dG)-tailed pBR322.

13. The infectious bovine rhinotracheitis virus as claimed in claim 7, wherein the resulting hybrid plasmid of step (1); is pLATKdlNdeI.

14. The infectious bovine rhinotracheitis virus as claimed in claim 7, wherein the resulting hybrid plasmid of step (2) is pLATKdlNdeI/βGalINV.

15. The infectious bovine rhinotracheitis virus as claimed in claim 7, wherein said tk⁺ IBRV host cells are selected from the group consisting of Rab-9 cells; primary rabbit kidney cells; secondary rabbit kidney cells; rabbit cornea (SIRC) cells; rabbit kidney (LLC-RK1) cells; embryo bovine trachea (EBTR) cells; bovine turbinate (BT) cells; Madin-Darby bovine kidney (MDBK) cells; and Georgia bovine kidney cells.

16. The infectious bovine rhinotracheitis virus as claimed in claim 7, wherein the infectious DNA of step (3) is derived from a tk⁺ IBRV selected from the group consisting of the Los Angeles strain, the Cooper strain, IPV strain K22, strain M03, strain M06, strain BFN-IH, strain BFN-IIN, strain BFN-IID, strains Gi 1 to 5, strain Bi, strain B4, strain BRV, strain LAE, strain V3 415, strain V3 416, strain V3 18, strain V3 93, strain BFA Wabu, strain P8–2, strain P10, strain P34, Alberta (Canada) isolates No. 1 to No. 122 and IBRV(RTK-1B).

17. The infectious bovine rhinotracheitis virus as claimed in claim 7, wherein said virus is lyopholized.

18. The infectious bovine rhinotracheitis virus as claimed in claim 12, wherein said cloning vector is pBR322.

19. The infectious bovine rhinotracheitis virus as claimed in claim 15, wherein said tk⁺ IBRV host cells are Rab-9 cells.

20. A vaccine for infectious bovine rhinotracheitis virus comprising:

(1) a pharmaceutically effective amount of an infectious bovine rhinotracheitis virus which fails to produce any functional thymidine kinase as a result of an insertion in the IBRV tk gene; and (2) a pharmaceutically acceptable carrier or diluent.

21. The vaccine for infectious bovine rhinotracheitis virus as claimed in claim 20, wherein said insertion is about 8 to 5000 bp in size.

22. The vaccine for infectious bovine rhinotracheitis virus as claimed in claim 20, wherein said insertion is a foreign gene which is inserted in a manner such that it is not expressed by said virus.

23. The vaccine for infectious bovine rhinotracheitis virus as claimed in claim 20, wherein said virus is also temperature-resistant.

24. The vaccine for infectious bovine rhinotracheitis virus as claimed in claim 20, wherein said virus has the identifying characteristics of IBRV(βGalINV) (ATCC No. VR 2160).

25. The vaccine for infectious bovine rhinotracheitis virus as claimed in claim 20, wherein said virus is lyopholized.

26. The vaccine for infectious bovine rhinotracheitis virus as claimed in claim 20, wherein said pharmaceutically acceptable carrier or diluent is physiologically buffered medium containing 2.5 to 15% (v/v) serum which does not contain antibodies to infectious bovine rhinotracheitis virus.

27. The vaccine for infectious bovine rhinotracheitis virus as claimed in claim 20, wherein said pharmaceutically effective amount is $10^{4.5}$ to $10^7$ p.f.u.

28. The vaccine for infectious bovine rhinotracheitis virus as claimed in claim 26, wherein said serum is selected from the group consisting of swine serum, calf serum, fetal calf serum, horse serum and lamb serum.

29. The vaccine for infectious bovine rhinotracheitis virus as claimed in claim 27, wherein said pharmaceutically effective amount is $10^{4.5}$ to $10^{5.5}$ p.f.u.

30. A vaccine for infectious bovine rhinotracheitis virus comprising:

(1) a pharmaceutically effective amount of an infectious bovine rhinotracheitis virus which fails to produce any functional thymidine kinase as a result of an insertion in the IBRV tk gene produced by the process comprising:

(a) constructing a hybrid plasmid comprising a cloning vector and a DNA fragment of IBRV containing substantially all of the IBRV tk gene and flanking sequences thereof;

(b) inserting a foreign DNA sequence within the IBRV tk gene of the resulting hybrid plasmid of step (a);

(c) co-transfecting, in $tk^+$ IBRV host cells, the hybrid plasmid of step (b) with infectious DNA from a $tk^+$ IBRV;

(d) selecting or screening, in $tk^-$ IBRV host cells, for $tk^-$ IBRV from the virus produced in step (c) so as to produce an infectious bovine rhinotracheitis virus mutant which fails to produce any functional thymidine kinase as a result of an insertion in the IBRV tk gene; and (2) a pharmaceutically acceptable carrier or diluent.

31. The vaccine for infectious bovine rhinotracheitis virus as claimed in claim 30, wherein said insertion is about 8 to 5000 bp in size.

32. The vaccine for infectious bovine rhinotracheitis virus as claimed in claim 30, wherein said insertion is a foreign gene which is inserted in a manner such that it is not expressed by said virus.

33. The vaccine for infectious bovine rhinotracheitis virus as claimed in claim 30, wherein the infectious DNA of step (c) is derived from a temperature-resistant infectious bovine rhinotracheitis virus such that the resulting mutant of step (d) is also temperature-resistant.

34. The vaccine for infectious bovine rhinotrachetis virus as claimed in claim 30, additionally comprising step (e):

(e) propagating the resulting infectious bovine rhinotracheitis virus of mutant step (d) at a non-permissive temperature for a temperature-sensitive virus so as to select for and produce a temperature-resistant infectious bovine rhinotracheitis virus mutant which fails to produce any functional thymidine kinase as a result of an insertion in the IBRV tk gene.

35. The vaccine for infectious bovine rhinotracheitis virus as claimed in claim 30, wherein said cloning vector is selected from the group consisting of pBR322, pMB9, pBR325, pKH47, pUC18, pUC19, pBR328, pHC79, phage Charon 28, pKB11, pKSV- 10, pPROK- 1, pYEJ001, pKC30, pKT280, pEUK-C1, pEUK-C2, pWE15, pMAM, pMAM-neo, pCH110, pdBPV-MMTneo, pMAR420 and oligo(dG)-tailed pBR322.

36. The vaccine for infectious bovine rhinotracheitis virus as claimed in claim 30, wherein the resulting hybrid plasmid of step (a) is pLATKdlNdeI.

37. The vaccine for infectious bovine rhinotracheitis virus as claimed in claim 30, wherein the resulting hybrid plasmid of step (b) is pLATKdlNdeI/βGalINV.

38. The vaccine for infectious bovine rhinotracheitis virus as claimed in claim 30, wherein said $tk^+$ IBRV host cells are selected from the group consisting of Rab-9 cells; primary rabbit kidney cells; secondary rabbit kidney cells; rabbit cornea (SIRC) cells; rabbit kidney (LLC-RK1) cells; embryo bovine trachea (EBTR) cells; bovine turbinate (BT) cells; Madin-Darby bovine kidney (MDBK) cells; and Georgia bovine kidney cells.

39. The vaccine for infectious bovine rhinotracheitis virus as claimed in claim 30, wherein the infectious DNA of step (c) is derived from a $tk^+$ IBRV selected from the group consisting of the Los Angeles strain, the Cooper strain, IPV strain K22, strain M03, strain M06, strain BFN-IH, strain BFN-IIN, strain BFN-IID, strains Gi 1 to 5, strain Bi, strain B4 strain BRV, strain LAE, strain V3 415, strain V3 416, strain V3 18, strain V3 93, strain BFA Wabu, strain P8-2, strain P10, strain P34, Alberta (Canada) isolates No. 1 to No. 122 and IBRV(RTK-1B).

40. The vaccine for infectious bovine rhinotracheitis virus as claimed in claim 30, wherein said virus is lyopholized.

41. The vaccine for infectious bovine rhinotracheitis virus as claimed in claim 30, wherein said pharmaceutically acceptable carrier or diluent is physiologically buffered medium containing 2.5 to 15% (v/v) serum which does not contain antibodies to infectious bovine rhinotracheitis virus.

42. The vaccine for infectious bovine rhinotracheitis virus as claimed in claim 30, wherein said pharmaceutically effective amount is $10^{4.5}$ to $10^7$ p.f.u.

43. The vaccine for infectious bovine rhinotracheitis virus as claimed in claim 35, wherein said cloning vector is pBR322.

44. The vaccine for infectious bovine rhinotracheitis virus as claimed in claim 38, wherein said $tk^+$ IBRV host cells are Rab-9 cells.

45. The vaccine for infectious bovine rhinotracheitis virus as claimed in claim 41, wherein said serum is selected from the group consisting of swine serum, calf serum, fetal calf serum, horse serum and lamb serum.

46. The vaccine for infectious bovine rhinotracheitis virus as claimed in claim 42, wherein said pharmaceutically effective amount is $10^{4.5}$ to $10^{5.5}$ p.f.u.

* * * * *